(12) United States Patent
Kaji et al.

(10) Patent No.: US 10,725,435 B2
(45) Date of Patent: Jul. 28, 2020

(54) MOTION CAPTURE APPARATUS

(71) Applicant: LEOMO, Inc., Newport Beach, CA (US)

(72) Inventors: Kunihiko Kaji, Tokyo (JP); Toshiya Ando, Tokyo (JP); Nobuyuki Matsushita, Tokyo (JP); Takuya Nishimura, Tokyo (JP); Shinichi Fukuma, Tokyo (JP)

(73) Assignee: LEOMO, Inc., Newport Beach, CA (US)

( * ) Notice: Subject to any disclaimer, the term of this patent is extended or adjusted under 35 U.S.C. 154(b) by 0 days.

(21) Appl. No.: 16/212,696

(22) Filed: Dec. 7, 2018

(65) Prior Publication Data

US 2019/0107812 A1 Apr. 11, 2019

Related U.S. Application Data

(63) Continuation of application No. 15/508,491, filed as application No. PCT/JP2015/075214 on Sep. 4, 2015, now abandoned.

(30) Foreign Application Priority Data

Sep. 4, 2014 (JP) .................. 2014-180645

(51) Int. Cl.
*G04G 21/02* (2010.01)
*A61B 5/11* (2006.01)
(Continued)

(52) U.S. Cl.
CPC .............. *G04G 21/025* (2013.01); *A61B 5/11* (2013.01); *A61B 5/112* (2013.01); *A61B 5/1112* (2013.01);
(Continued)

(58) Field of Classification Search
CPC ......... G01S 19/01; G01S 19/02; G04G 17/08; G04G 21/025; G04G 21/04; G06F 1/163;
(Continued)

(56) References Cited

U.S. PATENT DOCUMENTS 8,460,001 B1 * 6/2013 Chuang .............. G09B 19/0038
434/247
8,961,439 B2 * 2/2015 Yang .................... A61B 5/1038
600/595

(Continued)

*Primary Examiner* — Catherine T. Rastovski
(74) *Attorney, Agent, or Firm* — Yokoi & Co., U.S.A.; Toshiyuki Yokoi

(57) ABSTRACT

To allow combining devices having different functions according to an application, and improve convenience for a user. There are provided a wearing type terminal 1 provided with an external case 10 having a display unit 131 on the upper surface side and belt members 4a and 4b which can be connected to the both sides of the external case 10 respectively; and a docking type device 2 which is detachably engaged with the bottom portion of the external case 10 of the wearing type terminal 1, and is electrically connected to the wearing type terminal 1 via a dock side connection terminal 21. The wearing type terminal 1 and the docking type device 2 are provided with a function which carries out transmission and receiving of data to be displayed on the display unit 131 via the dock side connection terminal 21.

5 Claims, 24 Drawing Sheets

(51) Int. Cl.
   *G06F 1/16*      (2006.01)
   *G04G 21/04*     (2013.01)
   *G01S 19/01*     (2010.01)
   *G04G 17/08*     (2006.01)
   *G06F 3/0354*    (2013.01)
   *G06F 3/041*     (2006.01)
   *G06F 3/0488*    (2013.01)

(52) U.S. Cl.
   CPC ............ *A61B 5/1116* (2013.01); *A61B 5/1118* (2013.01); *A61B 5/1122* (2013.01); *G01S 19/01* (2013.01); *G04G 17/08* (2013.01); *G04G 21/04* (2013.01); *G06F 1/16* (2013.01); *G06F 1/163* (2013.01); *G06F 1/1686* (2013.01); *G06F 1/1698* (2013.01); *G06F 3/03547* (2013.01); *G06F 3/041* (2013.01); *G06F 3/0488* (2013.01); *A61B 2562/0219* (2013.01)

(58) Field of Classification Search
   CPC .. G06F 1/1686; G06F 1/1698; G06F 3/03547; G06F 3/041; G06F 3/0488; A61B 5/11; A61B 5/1112; A61B 5/1116; A61B 5/1118; A61B 5/112; A61B 5/1122; A61B 2562/0219
   See application file for complete search history.

(56)  References Cited

U.S. PATENT DOCUMENTS

| | | | |
|---|---|---|---|
| 9,067,097 B2* | 6/2015 | Lane | G06K 9/00342 |
| 9,282,893 B2* | 3/2016 | Longinotti-Buitoni | A61B 5/6804 |
| 9,595,130 B2* | 3/2017 | Wells | G06T 15/20 |
| 9,652,031 B1* | 5/2017 | Savastinuk | G06F 3/012 |
| 2007/0279852 A1 | 12/2007 | Daniel et al. | |
| 2008/0200310 A1 | 8/2008 | Tagliabue | |
| 2013/0324368 A1* | 12/2013 | Aragones | A61B 5/74 482/8 |
| 2014/0228989 A1 | 8/2014 | Tagliabue | |
| 2015/0345952 A1* | 12/2015 | Chang | G01C 22/002 701/541 |
| 2016/0303425 A1 | 10/2016 | Tagliabue | |

* cited by examiner

MOTION CAPTURE APPARATUS

TECHNICAL FIELD

The present invention relates to a so-called wearable type information terminal device having a watch function, a GPS function, a communication function and the like, and a motion capture system and a motion capture method making use of the information terminal device.

BACKGROUND ART

In recent years, along with the advent of the miniaturization, weight saving and multifunction of the information terminal device, various wearable information processing terminals have been proposed, i.e., so-called wearable terminals which can be worn on the body of a user (for example, refer to Patent Document 1). The technique disclosed in Patent Document 1 relates to a wrist watch type information processing terminal which can be worn on an arm of a user. Display and functions of great current consumption (organic EL, GPS, conversation and the like) are functionally divided into a main body and a dock, and a dock function can be added or modified and charged. As a result, a wrist watch type information terminal can be realized to be thin, small-sized, light-weighted, and waterproofed in a minimum size.

Also, Patent Document 2 discloses another example of the above wearable terminal which can be worn on an arm, and can recognize, store and communicate time, position, motion and other information through built-in sensors. The terminal makes it possible to perform connection and cooperation with a cellular phone, a PC, a health apparatus and the like through short-range communication.

Furthermore, since a wearable terminal is lightweight and provided with a clock function, a GPS function, a communication capability with various sensors such as a heart rate sensor, a system has been developed which can record and monitor body motions when the wearable terminal is worn during running, walking, sport training and exercising such as a bicycle (for example, refer to Patent Document 3).

In accordance with the system disclosed in this Patent Document 3, it is possible to perform realtime feedback to a user during athletic activity by attaching a device for measuring motion parameters on a shoe sole of the user, comparing baseline data with the motion parameters obtained by monitoring the user during the athletic activity, and in accordance with whether or not the result of comparison is within an allowable range.

PRIOR ART DOCUMENTS

Patent Documents

[Patent Document 1] Japanese Patent Published Application No. 2001-103536
[Patent Document 2] Japanese Patent Published Application No. 2002-269508
[Patent Document 3] Japanese Patent Published Application No. 2013-215590

SUMMARY OF THE INVENTION

Problems to be Solved by the Invention

However, in accordance with the techniques disclosed in Patent Documents 1 and 2 as described above, since all the functions tend to be incorporated within a single information terminal device so that there is a certain limitation in reducing size and weight, there is also a certain limitation in improving portability, and a user may hardly handle all the functions. Because of this, while a user desires a terminal in which is installed a function which is used by the user himself, the way of using the terminal differs among users so that it is difficult to provide a terminal meeting needs of users.

Furthermore, in accordance with the system disclosed in Patent Document 3 as described above, since only the measurement result of the sensor attached on a shoe sole is compared with baseline data, while differences from an ideal form can be analyzed, it is impossible to find the cause of the differences and analyze the influence among parameters for removing the cause. For example, in the case of a driving form of a bicycle, the rotation of a pedal ideally paces with the timing of exerting leg strength of an exercising person on pedals. However, since the skeleton of a pedaling foot and the operation of muscle are substantially complicated, it is difficult to analyze the cause of the collapse of the form only by measuring the parameters of a shoe sole.

On the other hand, it can be conceived to increase the number of sensors worn on an exercising person and incorporating a sensor also in a competition tool such as a bicycle. However, the increased number of sensors become obstacles to exercises and give stress to the exercising person. Also, if a sensor is needed in a competition tool, since there are competition games such as triathlon featuring a plurality of events, i.e., swimming, bicycle and running, it is required to mount measurement equipment and change the settings each time the event is switched so that it is lacking in the practical utility.

In order to solve the problem as described above, it is an object of the present invention to provide a wearable terminal which can be worn on the body of a user such that necessary functions can be combined in accordance with the use to meet needs of the wearable terminal and that portability and operability can be improved. Also, it is an object of the present invention to provide a system which can be used to appropriately correct the collapse of an exercise form of an exercising person by analyzing the influence among parameters of the exercise form throughout a plurality of events while reducing the stress given to the exercising person as much as possible by avoiding increase in the number of sensors and work for replacing the sensors when performing monitoring the exercising person.

Means for Solving Problem

In order to accomplish the object as described above, the present invention is characterized by a wearing type terminal which can be connected to a belt member at both sides of an external case having a display unit on an upper side; and a docking type device which can be detachably connected to a bottom portion of the external case of the wearing type terminal, and electrically connected to the wearing type terminal through a first connection terminal; wherein the wearing type terminal and the docking type device have a function to transmit and receive data to be displayed on the display unit through the first connection terminal.

In accordance with the present invention as described above, it is possible to integrate, in the wearing type terminal, information display functions such as a clock function, a positional information display function and basic functions such as operation interfaces through a display unit such as a touch panel and buttons. On the other hand, the docking type device is implemented with other functions such as a short-range communication ability. Since the docking type device can be electrically connected to the wearing type terminal through the connection terminal, it is possible to suitably add a necessary function to the wearing type terminal by selecting the docking type device and connecting the selected docking type device through the connection terminal. As a result, in accordance with the present invention, since devices having various functions can be combined, and necessary functions can be suitably selected and used by attaching and detaching the devices in accordance with the use, it is possible to improve the portability as the wearable terminal.

In the invention as described above, it is preferred that the wearing type terminal is provided with a first antenna for use in first wireless communication, wherein the docking type device is provided with a second antenna for use in second wireless communication, wherein the second antenna is arranged in order to overlap the bottom portion of the external case of the docking type device in a plan view, and wherein the first antenna is arranged on the outer edges of the external case in order not to interfere with the second antenna. In this case, the first antenna and the second antenna for use in wireless communication installed in the wearing type terminal and the docking type device are arranged in order not to interfere with each other, and therefore the radio waves of the antennas are prevented from interfering with each other. As a result, it is possible to prevent the signal reception performance from being degraded.

In the invention as described above, it is preferred that the display unit is curved or bent in the direction connecting opposite sides to which the belt member is connected. In this case, since the screen of the display unit is curved or bent, when the wearing type terminal is of a type which is worn on an arm, it is possible to fit the wearing type terminal around the curved surface of the arm of a user, while securing the display area, and expand the view angle of the display unit, when viewing the screen of the display unit after wearing the information terminal device on the arm, to make it possible to immediately confirm the display content on the display unit.

In the invention as described above, there is further provided a power supply device detachably connected to a bottom portion of the docking type device and electrically connected to the docking type device through a second connection terminal to supply electric power through the first connection terminal and the second connection terminal. In this case, since the power supply device is detachably connected to the bottom portion of the docking type device to supply electric power through the first connection terminal and the second connection terminal, electric power is supplied to the wearing type terminal and the docking type device by connecting the power supply device with the docking type device while the docking type device is connected with the wearing type terminal. Meanwhile, when electric power is supplied to the wearing type terminal and the docking type device, the electric power is supplied first to the wearing type terminal and then to the docking type device.

In the invention as described above, it is preferred that the power supply device is provided with a data communication unit to transmit and receive data with the wearing type terminal or the docking type device through the first connection terminal and the second connection terminal and wherein the data communication unit is capable of transmitting and receiving data with an external device through an external terminal provided on the outside of the power supply device. In this case, since the power supply device is provided with the data communication unit to transmit and receive data with the wearing type terminal or the docking type device through the first connection terminal and the second connection terminal, it is possible to record various data from an external terminal such as a personal computer to the wearing type terminal and the docking type device through the power supply device.

Also, another invention is a motion capture system which detects body motions of a wearer, comprising: body motion sensors which are worn on parts of the body of the wearer to detect three-dimensional displacement and acceleration of each of the parts; sole sensors attached to soles of the wearer to detect pressures exerted on the soles; a body motion recording unit configured to accumulate detection results of the body motion sensors and the sole sensors as body motion data; a body motion calculation unit configured to calculate body motions of the wearer as body motion reproduction data on the basis of the detection results of the body motion sensors accumulated in the body motion recording unit and the relative positional relationship among the body motion sensors; a correction unit configured to correct the body motion reproduction data calculated by the body motion calculation unit on the basis of the detection result of the sole sensors; an analysis unit configured to analyze the body motions of the wearer on the basis of the body motion reproduction data corrected by the correction unit; and an output device configured to display or output the analysis result of the analysis unit.

A further invention is a motion capture method of detecting body motions of a wearer comprising:

(1) a detecting step of detecting three-dimensional displacements and accelerations of parts of the body of the wearer with body motion sensors which are worn on the parts, and detecting pressures exerted on soles of the wearer with sole sensors attached to the soles;

(2) a body motion recording step of accumulating detection results of the body motion sensors and the sole sensors as body motion data in a body motion recording unit;

(3) a body motion reproduction data generating step of calculating body motions of the wearer with a body motion calculation unit as body motion reproduction data on the basis of the detection results of the body motion sensors accumulated in the body motion recording unit and the relative positional relationship among the body motion sensors;

(4) a body motion reproduction data correcting step of correcting the body motion reproduction data, which is calculated by the body motion calculation unit, with a correction unit on the basis of the detection result of the sole sensors;

(5) an analyzing step of analyzing the body motions of the wearer with an analysis unit on the basis of the body motion reproduction data corrected by the body motion reproduction data correcting step; and an outputting step of displaying or outputting the analysis result of the analysis unit with an output device.

In this case, the "body motion sensor" is a sensor which detects the three-dimensional displacement and acceleration of each part and may be a sensor which incorporates a three-axis acceleration meter for measuring the acceleration of an object, a three-axis gyroscope for measuring the angular speed of the object, a three-axis magnetic sensor for measuring the magnitude and direction of a magnetic field, so that motions about nine axes can be detected.

In accordance with the present invention as discussed above, it is possible to let a wearer recognize body motions of the wearer herself, and advise improvement of the body motions of the wearer, by attaching the body motion sensors and the sole sensors to the body of the wearer, calculating the body motions of the wearer as body motion reproduction data on the basis of the detection results of the sensors, analyzing the body motion reproduction data, and displaying the analysis results on the display device. At this time, since the correction unit corrects the body motion reproduction data calculated by the body motion calculation unit on the basis of the detection results of the sole sensors, even when a deviation occurs in the relative position of the body motion reproduction data to the ground due to noise and error occurring in the detection results of the body motion sensors such as nine-axis sensors, it is possible to appropriately build, display and output the body motion reproduction data by making use of the timing detected by the sole sensors when the sole comes in contact with a floor to correct the value of each body sensor (for example, zero correction).

In the invention as described above, it is preferred to further provide a data collection unit configured to acquire detection results of the body motion sensors and the sole sensors; and a data transfer unit configured to convert the detection results acquired by the data collection unit to data in an integrated format and transmit the data to the body motion recording unit. In this case, since detection results can collectively be transferred to another terminal by grouping a number of body motion sensors, collecting data for each group, and converting the data in an integrated format, even in the case where a number of body motion sensors and the sole sensors are worn, it is possible to handle such many sensors and a large amount of data by making use of the data collection unit and the data transfer unit as the hub and temporarily collecting and integrating data in the data transfer unit even if the number of connections with communication devices and the data transfer amount are limited.

In the invention as described above, it is preferred that the body motion recording unit is the information terminal device as described above. In this case, it is possible to make the device for accumulating body motion data in the form of a wearable watch type device having excellent portability, and easily collect body motion data while performing exercise and sports.

In order to accomplish the object as described above, the present invention provide a motion capture system which detects body motions of a wearer comprising:

a plurality of body motion sensors which are worn on left and right parts of the body of the wearer to detect three-dimensional displacement and acceleration of each of the parts;

a body motion recording unit configured to accumulate detection results of the body motion sensors as body motion data;

a body motion calculation unit configured to calculate body motions of the wearer as body motion reproduction data on the basis of the detection results of the body motion sensors and the relative positional relationship among the body motion sensors;

a cycle extracting unit configured to extract cyclic variation from body motions on the basis of the body motion reproduction data accumulated on the body motion recording unit;

a correction unit configured to correct the body motion reproduction data calculated by the body motion calculation unit on the basis of the cyclic variation extracted by the cycle extracting unit;

an analysis unit configured to analyze the body motions of the wearer on the basis of the body motion reproduction data corrected by the correction unit; and an output device configured to display or output the analysis result of the analysis unit.

Also, the present invention provides a motion capture method of detecting body motions of a wearer comprising:
(1) a detecting step of detecting three-dimensional displacements and accelerations of parts of the body of the wearer with a plurality of body motion sensors which are worn on the parts;
(2) a body motion recording step of accumulating detection results of the body motion sensors as body motion data in a body motion recording unit;
(3) a body motion reproduction data generating step of calculating body motions of the wearer with a body motion calculation unit as body motion reproduction data on the basis of the detection results of the body motion sensors accumulated in the body motion recording unit and the relative positional relationship among the body motion sensors, and extracting cyclic variation from body motions on the basis of the body motion reproduction data accumulated on the body motion recording unit with a cycle extracting unit;
(4) a body motion reproduction data correcting step of correcting the body motion reproduction data, which is calculated by the body motion calculation unit, with a correction unit on the basis of the cyclic variation extracted by the cycle extracting unit;
(5) an analyzing step of analyzing the body motions of the wearer with an analysis unit on the basis of the body motion reproduction data corrected by the body motion reproduction data correcting step; and
(6) an outputting step of displaying or outputting the analysis result of the analysis unit with an output device.

Furthermore, the present invention provides a motion capture program for detecting body motions of a wearer, causing a computer to perform:
(1) a detecting step of detecting three-dimensional displacements and accelerations of parts of the body of the wearer with a plurality of body motion sensors which are worn on the parts;
(2) a body motion recording step of accumulating detection results of the body motion sensors as body motion data in a body motion recording unit;
(3) a body motion reproduction data generating step of calculating body motions of the wearer with a body motion calculation unit as body motion reproduction data on the basis of the detection results of the body motion sensors accumulated in the body motion recording unit and the relative positional relationship among the body motion sensors, and extracting cyclic variation from body motions on the basis of the body motion reproduction data accumulated on the body motion recording unit with a cycle extracting unit;
(4) a body motion reproduction data correcting step of correcting the body motion reproduction data, which is calculated by the body motion calculation unit, with a correction unit on the basis of the cyclic variation extracted by the cycle extracting unit;
(5) an analyzing step of analyzing the body motions of the wearer with an analysis unit on the basis of the body motion reproduction data corrected by the body motion reproduction data correcting step; and
(6) an outputting step of displaying or outputting the analysis result of the analysis unit with an output device.

In accordance with the invention as described above, the body motion reproduction data is calculated on the basis of the detection results of the body motion sensors and the variation in the relative positional relationship among the body motion sensors, and cyclic variation is extracted on the basis of the body motion reproduction data accumulated on the body motion recording unit.

In accordance with the present invention as discussed above, it is possible to let a wearer recognize body motions of the wearer herself, and advise improvement of the body motions of the wearer, by attaching a plurality of body motion sensors to the body of the wearer, calculating the body motions of the wearer as body motion reproduction data on the basis of the detection results of the sensors, analyzing the body motion reproduction data, and displaying the analysis results on the display device. At this time, since the correction unit corrects the body motion reproduction data calculated by the body motion calculation unit on the basis of the cyclic variation extracted by the cycle extracting unit, even when a deviation occurs in the relative position of the body motion reproduction data to the ground due to noise and error occurring in the detection results of the body motion sensors such as nine-axis sensors, it is possible to appropriately build, display and output the body motion reproduction data by making use of the timing of the cyclic variation extracted by the cycle extracting unit to correct the value of each body sensor (for example, zero correction).

Effects of the Invention

As has been discussed above, in accordance with the present invention, it is possible to provide a function as a biological monitor in addition to a watch function, a GPS function and a communication function, combine necessary functions in an information processing terminal, which can be worn on the body of a user, in accordance with the use, meet needs of a wearable terminal, thin (miniaturize) the respective devices, and improve portability and operability.

Furthermore, in accordance with the present invention, it is possible to appropriately correct the collapse of an exercise form of an exercising person by analyzing the influence among parameters of the exercise form throughout a plurality of events while reducing the stress given to the exercising person as much as possible by avoiding increase in the number of sensors and work for replacing the sensors when performing monitoring the exercising person.

BRIEF DESCRIPTION OF THE DRAWINGS

FIG. 24A is a perspective view for showing the overall configuration of an information terminal device (implemented with a large display) in accordance with the embodiment, and FIG. 24B is an explanatory view for showing the usage thereof.

FIG. 27A is a schematic view for showing motion capture during running, and FIG. 27B is a schematic view for showing motion capture during a bicycle race.

MODE FOR CARRYING OUT THE INVENTION

First Embodiment

Figure 1:
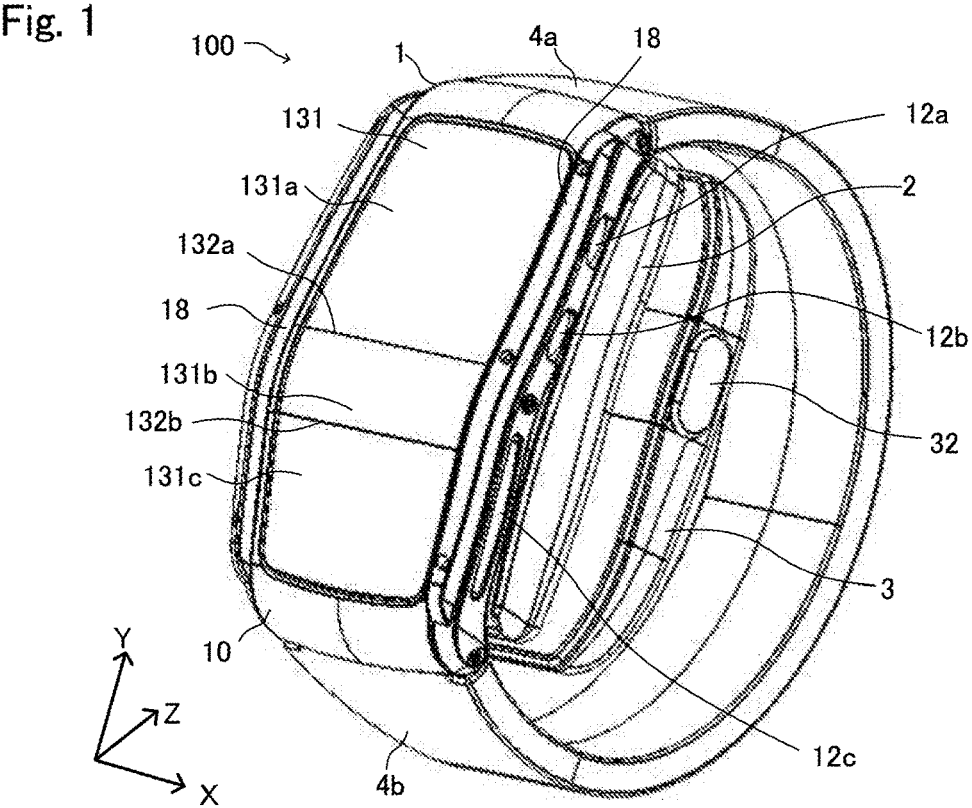
FIG. 1 is a perspective view showing the overall configuration of an information terminal device in accordance with a first embodiment.
Figure 2:
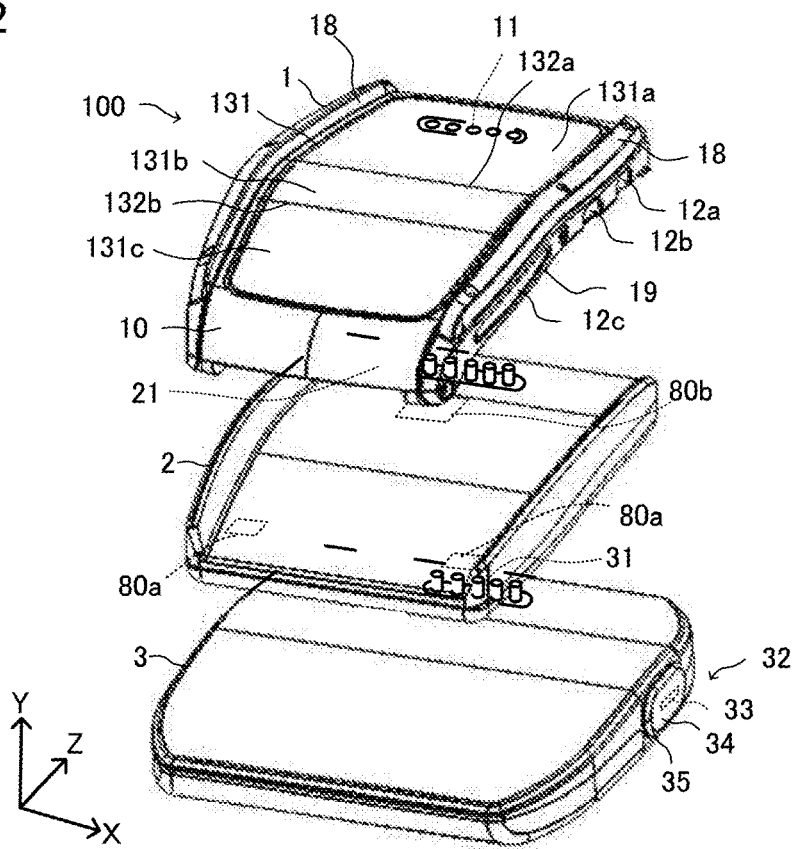
FIG. 2 is an exploded perspective view for showing the configuration of the information terminal device in accordance with the first embodiment.
Figure 3:
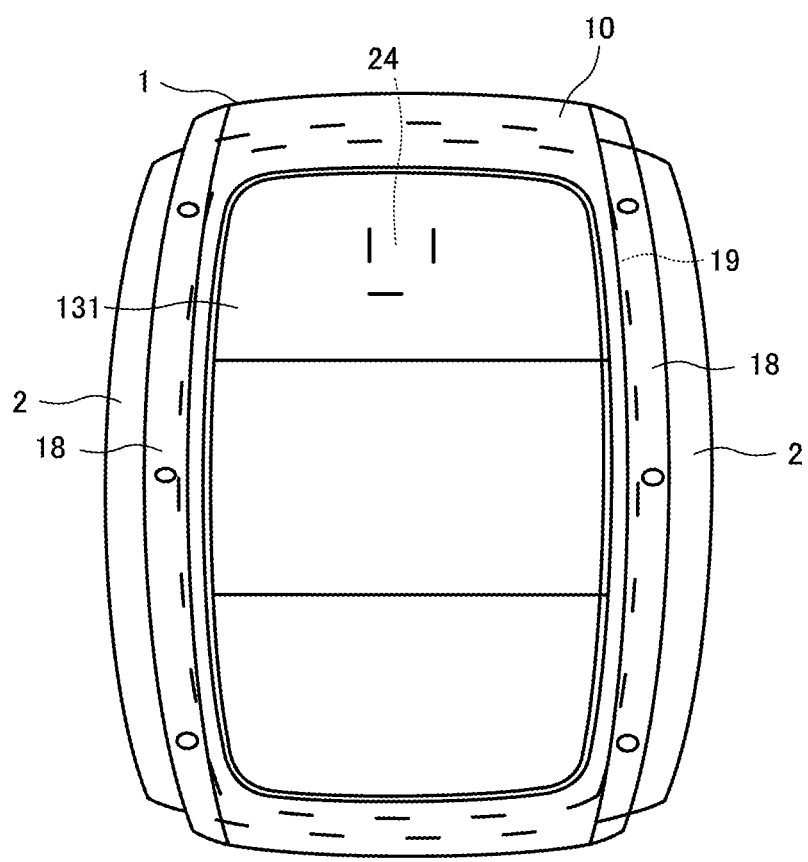
FIG. 3 is a top view showing the positional relationship between a GPS antenna and a wireless antenna in accordance with the first embodiment.

In what follows, with reference to the accompanying drawings, embodiments of an information terminal device in accordance with the present invention will be explained in detail. FIG. 1 is a perspective view showing the overall configuration of an information terminal device 100 in accordance with a first embodiment. FIG. 2 is an exploded perspective view for showing the configuration of the information terminal device 100 in accordance with the first embodiment. Also, FIG. 3 is a top view showing the positional relationship between a GPS antenna and a wireless antenna in accordance with the first embodiment. Meanwhile, in the following description of the information terminal device 100, the surface which comes in contact with an arm is referred to as a bottom surface, and the surface opposite to the bottom surface is referred to as an upper surface.

The information terminal device 100 in accordance with the present embodiment is a wrist watch type wearable terminal which can be worn by a user with a belt, as illustrated in FIG. 1 and FIG. 2, and consists of a wearing type terminal 1 which can be worn on the arm of the user, a docking type device 2 and a power supply device 3 which is detachably connected with the docking type device 2. Incidentally, the wearing type terminal 1 and the docking type device 2 are also detachably attached to each other and can be separated and joined if necessary. Also, there are many types of the wearing type terminal 1 and docking type device 2 which have different additional functions and designs in accordance with using purposes respectively, and can be arbitrarily selected and freely combined for the purposes.

Incidentally, the wearing type terminal 1 and the docking type device 2 can be attached and detached through a release mechanism for fixing with a magnet or a lock mechanism. Specifically, as illustrated in FIG. 1, magnets 80a and 80b are provided in predetermined positions on the upper surface of the docking type device 2. These magnets 80a and 80b form a magnet type release mechanism with members which are made of a material attracted by the magnets and located in positions corresponding to the magnets 80a and 80b on the bottom surface of the wearing type terminal 1.

The wearing type terminal 1 is provided with an external case 10 having a display unit 131 on the upper surface side, and belt members 4a and 4b which can be connected to the both sides of the external case 10 respectively. The belt members 4a and 4b are members for wearing the wearing type terminal 1 on an arm, can be formed of one of various detachable belts such as a metallic belt, a rubber belt, a leather belt and a nylon belt. On the other hand, the wearing type terminal 1 can be mounted on a bicycle, an automobile or the like apparatus with the belt members 4a and 4b or another attachment to extend the functionality.

The external case 10 is a case member for mounting a PCB, in which information processing functionality is implemented, in the form of a frame having openings on the upper surface side and the bottom surface side respectively. Then, the display unit 131 is located in the opening on the upper surface side of the external case 10, and a back lid 19 is located in the opening on the bottom surface side. In the case of the present embodiment, a center portion and the back lid on the bottom surface side of the external case 10 are made of a nonconductive material such as a plastic material, opposite end portions are made of a metallic material such as a stainless steel, and the upper surface side is made of a synthetic resin such as polyurethane.

The display unit 131 of the external case 10 is a display for displaying a message, an input string or the like to a user, and provided with a touch panel integrally formed on the upper surface side thereof. This touch panel detects a position touched of the display, for example, in units of dots forming the display by a detection system of a pressure-sensitive type, an optical type, an electrostatic type, an electromagnetic induction type or the like type to output a signal indicative of the detected position (hereinafter referred to as "touch position"). The touch position is represented by an XY coordinate system which is set as a coordinate system of the detection plane of the touch panel. A user can perform various input operations by a touch operation on the display with a touch pen PN, a finger or the like.

This touch panel, which is waterproofing, can detect a touched position of the display and outputs the detection signal as a touch position even on the surface of the water by a special electrostatic capacitance detection system. The touch position is represented by an XY coordinate system which is set as a coordinate system of the detection plane of the touch panel. A user can perform various input operations by a touch operation on the display even under water. Incidentally, the watch body can be operated also with mechanical buttons which are provided on the watch body.

This display unit 131 is formed in a generally rectangular shape with a long side in the direction connecting opposite sides to which the belt members 4a and 4b are connected (the Y-axis direction in FIG. 1), and bent in the direction connecting opposite sides to which the belt members 4a and 4b are connected. Specifically, as illustrated in FIG. 1 and FIG. 2, the display unit 131 has two creases 132a and 132b in parallel with the X-axis direction perpendicular to the Y-axis direction. The liquid crystal display device of the display unit 131 consists of three display screens 131a to 131c arranged to bend at different angles at the creases 132a and 132b as mountain fold lines.

Also, the wearing type terminal 1 is provided with a GPS antenna 18a and a wireless antenna 18b which are arranged on the outer edges of the external case 10 respectively. The GPS antenna 18a is an antenna (first antenna) for wireless communication made of a conductive material such as a stainless steel for acquiring satellite information such as satellite orbit information, GPS time information, positional information and the like which are included in a navigation message of a satellite signal in a 1.5 GHz band extracted through a SAW filter which is not shown in the figure. The wireless antenna 18b is an antenna (first antenna) for BTLE (Bluetooth (registered trademark) Low Energy) and ANT+, which are very low power consumption short range communication standards, and used for communicating with various sensors and other small devices worn on a body. This wireless antenna 18b is made also of a conductive material such as a stainless steel. Meanwhile, while the present embodiment shows the GPS antenna 18a and the wireless antenna 18b arranged in the left and right sides as in the illustrated fashion, the present invention is not limited thereto, but the left and right arrangement can be changed if necessary.

Also, in the case of the present embodiment, the wearing type terminal 1 is equipped with operation buttons 12a to 12c for manually manipulating on the side surface of the external case 10, i.e., three buttons 12a to 12c on one side of the external case 10.

Furthermore, in the case of the present embodiment, the wearing type terminal 1 is waterproofing, and has the function to acquire and display speed information and positional information by processing radio waves (wireless signals) from a GPS satellite. Still further, an acceleration sensor or the like can be incorporated in the wearing type terminal 1 to provide the functionality as an activity meter on the basis of the measurement of acceleration of body motions.

On the other hand, the docking type device 2 is an information terminal device which is detachably coupled with the wearing type terminal 1, and has the same size as the external case 10 of the wearing type terminal 1 in the form of a thin plate as an almost rectangular box. In the case of the present embodiment, the docking type device 2 is made of a synthetic resin such as a cured plastic and provided with an information terminal device such as a CPU inside thereof. Then, in the case of the present embodiment, this docking type device 2 is formed with a dock side connection terminal (first connection terminal) 21 on the upper surface thereof, and detachably joined with the back lid 19 which is the bottom portion of the external case of the wearing type terminal 1 through the dock side connection terminal 21.

Specifically, the back lid 19 which is the bottom portion of the wearing type terminal 1 is provided with a terminal side connection terminal 11 in a position corresponding to the dock side connection terminal 21 so that the docking type device 2 and the wearing type terminal 1 can electrically be connected to each other by connecting the dock side connection terminal 21 with the terminal side connection terminal 11. The wearing type terminal 1 and the docking type device 2 are configured to supply electric power from the docking type device 2 to the wearing type terminal 1 through the dock side connection terminal 21, and transmit and receive data therebetween for displaying the data on the display unit 131.

Also, this docking type device 2 is equipped with a battery, has an RFID communication capability for contactlessly reading and writing data through wireless radio waves, and is capable of wirelessly communicating with an external reader writer with a wireless communication antenna (second antenna) 24 provided on the docking type device 2. This wireless antenna 24 is an antenna for contactless wireless communication (NFC (Near Field Communication)) to transmit and receive data by the use of weak radio waves radiated from the external reader writer.

Then, in the case of the present embodiment, this wireless antenna 24, the GPS antenna 18a and the wireless antenna 18b of the wearing type terminal 1 are arranged in order not to overlap each other in a plan view as illustrated in FIG. 3.

Specifically, as illustrated in FIG. 3, this wireless antenna 24 is arranged in order to overlap the bottom portion of the external case 10 of the docking type device 2. The GPS antenna 18a and the wireless antenna 18b installed in the wearing type terminal 1 are located on the opposite sides of the external case 10 and arranged in order not to interfere with the wireless antenna 24.

The power supply device 3 is a device detachably connected with the bottom portion of the docking type device 2 for supplying electric power to the wearing type terminal 1 and the docking type device 2, and made of a synthetic resin such as a cured plastic in the form of a thin plate as an almost rectangular box. In the case of the present embodiment, the power supply device 3 may be an indoor installation type device to be installed in user's home or the like, or a portable device to be installed in an automobile or a bicycle. In the case where the power supply device 3 is an indoor installation type device, electric power is supplied through a wall outlet and a power cable. On the other hand, in the case where the power supply device 3 is a portable device, a battery may be provided which can accumulate power supply through an external AC adapter. Meanwhile, this battery may incorporate a transformer, a rectifier, a regulating circuit for converting an alternating current to a direct current.

Also, in the case of the present embodiment, the power supply device 3 is provided with a USB terminal 33 to be electrically connected to an external device such as a personal computer. The USB terminal 33 is provided on outside side of the power supply device 3, can be connected to an external device through a USB cable, and installed in a connector 32 which is located at one side of the power supply device 3 for protecting the USB terminal 33.

As illustrated in FIG. 1 and FIG. 2, the connector 32 consists of a cylindrical member 35 which is located in the side of the external case 10 and in which the USB terminal 33 is installed, and a lid member 34 fitted to the USB terminal 33 in order to cover the USB terminal 33 and the peripheral clearance around the USB terminal 33. The USB terminal 33 is waterproofed by the cylindrical member 35 and the lid member 34 as described above. Incidentally, the USB terminal 33 may consist of one of various types of connectors such as type A, type B, mini, micro USB connectors. Also, the external connection terminal is not limited to the USB terminal, but may be a power terminal, a LAN terminal, a telephone terminal, or any other modular connector.

The power supply device 3 of the present embodiment is detachably connected to the bottom portion of the docking type device 2 and has the function to supply electric power from the AC adapter through the USB terminal 33 or electric power accumulated in the battery to the docking type device 2 and the wearing type terminal 1. Specifically, a power supply device side connection terminal (second connection terminal) 31 is projected from the upper surface of the power supply device 3 in a position corresponding to the dock side connection terminal 21 of the docking type device 2 in order that the dock side connection terminal 21 and the power supply device side connection terminal 31 are connected when the power supply device 3 is mounted on the bottom portion of the docking type device 2. The power supply device 3 is thereby electrically connected to the docking type device 2 through the power supply device side connection terminal 31 to supply electric power to the docking type device 2. Also, since the dock side connection terminal 21 is electrically connected to the terminal side connection terminal 11 which is arranged on the bottom surface of the wearing type terminal 1, the power supply device 3 can supply electric power also to the wearing type terminal 1 through the dock side connection terminal 21 and the power supply device side connection terminal 31.

Figure 5A:
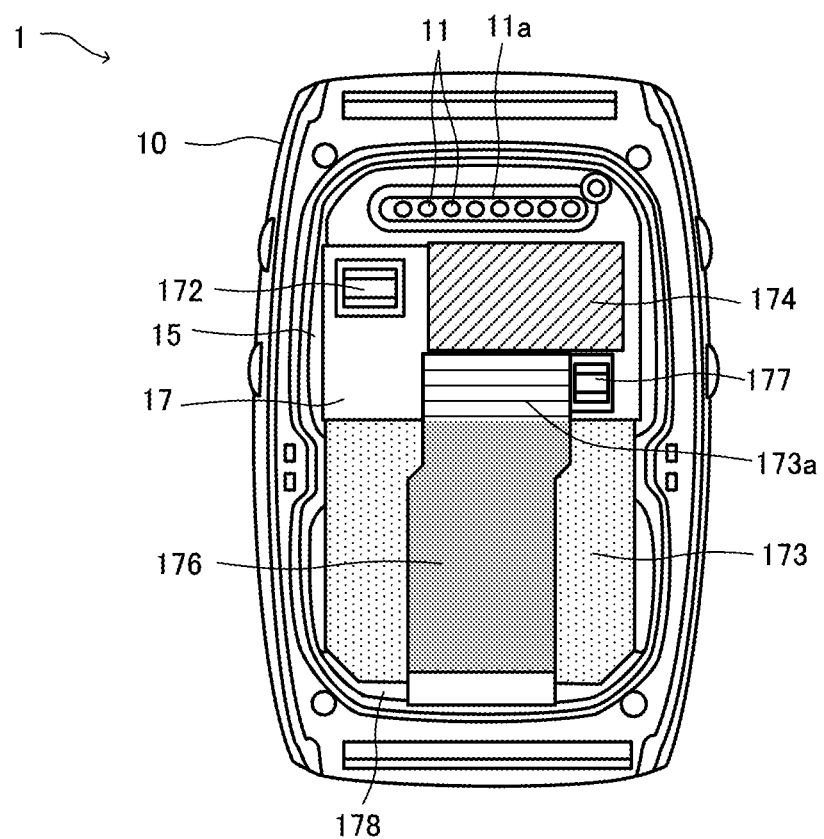
FIG. 5A is an explanatory view for showing the internal structure of the wearing type terminal as seen from the back side in accordance with the first embodiment.
Figure 5B:
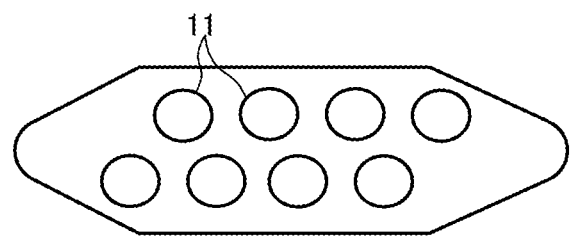
FIG. 5B is an explanatory view for showing a modified example of a pin arrangement of a terminal side connection terminal.

Incidentally, the pin layout of the terminal side connection terminal 11 is not only a linear arrangement as illustrated in FIG. 5A but also is an alternative pin arrangement as illustrated in FIG. 5B.

Also, the power supply device 3 is provided with a function as a data communication unit for transmitting and receiving data from/to the wearing type terminal 1 and the docking type device 2 through the dock side connection terminal 21 and the power supply device side connection terminal 31, such that data is transmitted and received from/to the dock side connection terminal 21 and the power supply device side connection terminal 31 by transmitting and receiving data from/to an external device through an external terminal which is provided on the outside of the power supply device 3 and connectable with the USB terminal 33.

Incidentally, the configuration of the power supply device 3 can be modified in accordance to the use. For example, in the case where the power supply device 3 is installed on a table or the like, an installation base is provided on the bottom surface thereof. Also, in the case where the power supply device 3 is installed on a bicycle, an attachment member is attached for housing or fixing the power supply device 3 to a handlebar.

(Internal Configuration of Wearing Type Terminal 1)

Figure 4A:
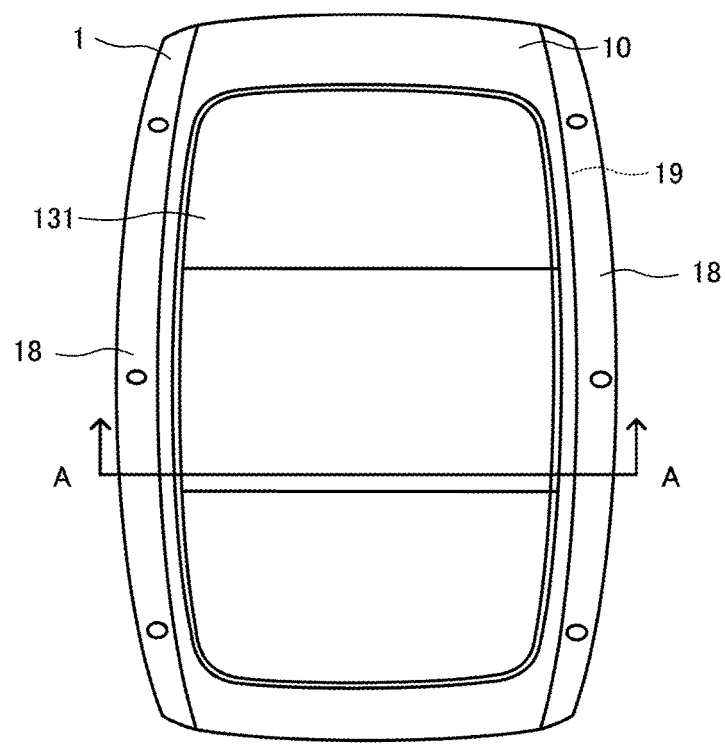
FIG. 4A is a top view of the wearing type terminal as seen from the above in accordance with the first embodiment.
Figure 4B:
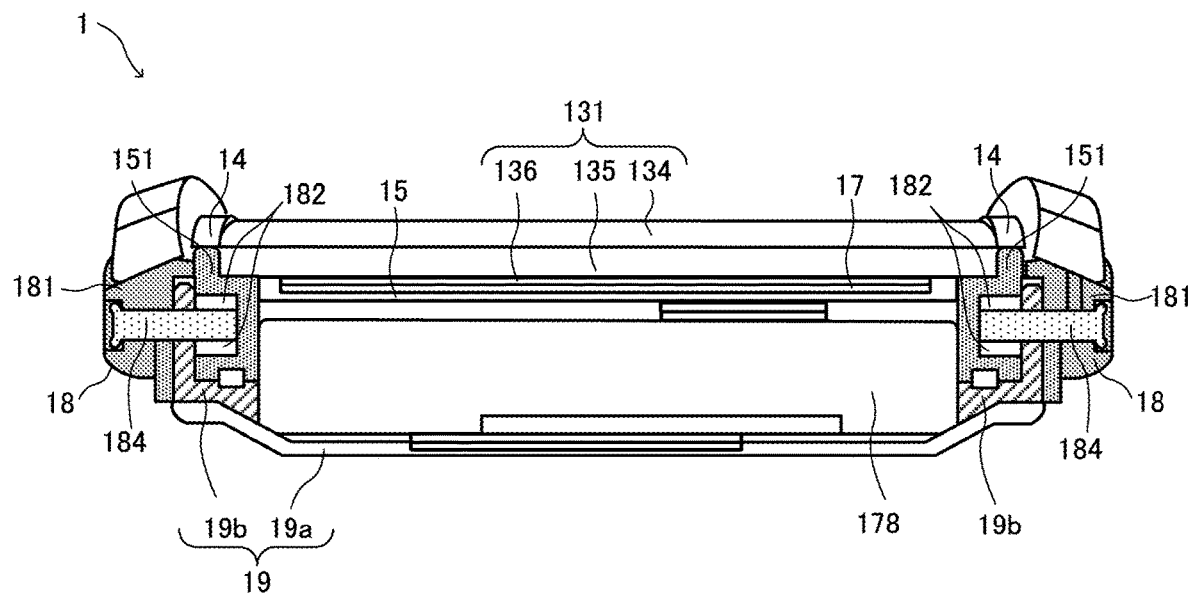
FIG. 4B is part of a cross sectional view along A-A line of FIG. 4A.

Next is an explanation of the internal configuration of the wearing type terminal 1. FIG. 4A is a top view of the wearing type terminal 1 as seen from the above in accordance with the present embodiment. FIG. 4B is part of a cross sectional view along A-A line of FIG. 4A. Also, FIG. 5 is an explanatory view for showing the internal structure of the wearing type terminal 1 as seen from the back side in accordance with the present embodiment.

In the internal space of the external case 10, the GPS antenna 18a and the wireless antenna 18b are arranged on the sides of the external case 10 as illustrated in FIG. 4B. The GPS antenna 18a and the wireless antenna 18b are provided with main bodies 181 located outside the external case 10 and projection members 184 inserted from the main bodies 181 inwardly through the external case 10 as illustrated in FIG. 4B. The projection members are arranged in order to come in contact with antenna springs 16 in the inside of the external case 10. The antenna spring 16 is a connection terminal made of a conductive material such as a stainless steel for electrically connecting the GPS antenna 18a and the wireless antenna 18b with receiver units incorporating IC chips for receiving GPS and BTLE signals such that one end of the antenna spring 16 contacts the projection member 184 and the other end contacts the receiver units. Accordingly, a GPS signal transmitted from a GPS satellite is received by a GPS receiver unit 119a through the GPS antenna 18a, and a radio frequency signal is received by a wireless communication unit 119b through the wireless antenna 18b.

Also, an 0 ring 182 is interposed between the external case 10 and the wireless antenna 18b and external case 10 in order to hold the outer circumference of the projection member 184 therein, fix the GPS antenna 18a to the external case 10 and seal the inside of the external case 10. The 0 ring 182 is made also of a conductive material such as a stainless steel.

Also, in the internal space of the external case 10 of the wearing type terminal 1 as illustrated in FIG. 4B, there are arranged the display unit 131, a display unit supporting plate 15, the antenna spring 16, a circuit board 17 and the back lid 19 in the order from the display unit 131 (the upper surface) side to the back lid 19 (the bottom surface) side.

The display unit 131 incorporates a touch panel which is an input device for inputting operation signals and consists of a display panel 136 for displaying graphics on the display unit supporting plate 15, a touch sensor 135 for receiving an operation signal corresponding to a coordinate position of the graphics displayed on the display panel 136, and a protection cover 134 for protecting the touch sensor 135 and the display panel 136.

The display panel 136 is formed of an organic EL (OLED (Organic Light-Emitting Diode)), an electronic paper, a film liquid crystal or the like, and electrically connected to the circuit board 17 through flexible printed circuit boards 176 and 177 to display various information such as information generated on the basis of signals included in radio waves received through the GPS antennas 18 and 18 in accordance with a display control signal output from a control unit 170 installed in the circuit board 17.

The touch sensor 135 is a sensor for detecting a position touched by a user, and, in the case of the present embodiment, of an electrostatic capacitance type making use of a transparent conductive film. Alternatively, the touch sensor 135 may be a sensor for detecting coordinates such as of a pressure-sensitive type, an electromagnetic induction type, a magnetostrictive type. The touch sensor 135 is also electrically connected to the circuit board 17, and outputs operation position information to the control unit 170 installed in the circuit board 17.

The protection cover 134 is preferably a glass plate made of a white sheet glass, a sapphire glass, an alkali glass such as a borosilicate glass, an alkali-free glass, an acryl (polycarbonate) glass, a chemically strengthened glass or the like. Then, the protection cover 134 is attached to the upper surface side of the external case 10 to close the opening on the upper surface side through a packing 14 and seal the inside of the external case 10.

The display unit supporting plate 15 is a plate-like member which supports and protects the display unit 131 to cover the entirety of the elements of the display unit 131 in a plan view. The display unit supporting plate 15 is attached to the bottom surface of the display unit 131 through a bonding member. Incidentally, this display unit supporting plate 15 is electrically connected to the circuit board 17 so that electric power is supplied from the circuit board 17 to the display unit 131 through the display unit supporting plate 15.

The circuit board 17 is made of a material including a resin or a dielectric, and incorporates the control unit 170 which is an MCU (memory control unit) consisting of various ICs and the like for controlling the display unit 131, processing satellite signals received by the GPS antennas 18 and 18. Various information items are displayed on the display unit 131 by controlling a main control implemented in this control unit 170.

Also, in the external case 10 as illustrated in FIG. 5, there are the flexible printed circuit board 176 for the liquid crystal panel of the display unit 131 and a flexible printed circuit board 175 for the touch panel. Each of the flexible printed circuit boards 175 and 176 is a board formed by sticking a conductive metal such as copper foil to an insulating thin flexible base film (polyimide or the like) and forming an electrical circuit thereon, and electrically connected to the circuit board 17 through a connector 171 for the liquid crystal panel and a connector 172 for the touch panel respectively at one end, and connected to the display panel 136, the touch sensor 135 and the like at the other end.

Also, on the circuit board 17 as illustrated in FIG. 5, there is an insertion hole 11*a* through which the terminal side connection terminal 11 is inserted to come in contact with the connection terminal 21 of the docking type device 2. The terminal side connection terminal 11 is located in this insertion hole 11*a* to supply electric power from the docking type device 2 or the power supply device 3 to the circuit board 17. Meanwhile, in the case of the present embodiment, the terminal side connection terminal 11 is located in such a position as not to overlap an area 174 in which are arranged the control unit 170, the GPS receiver unit 119*a*, the wireless communication unit 119*b* and the like in a plan view. Furthermore, the area 174 is located on an upper position of the circuit board 17 shown in FIG. 5, and there are installed the control unit 170, the GPS receiver unit 119*a*, the wireless communication unit 119*b*, an acceleration sensor 115 for detecting acceleration and the like in the area 174.

On the other hand, as illustrated in FIGS. 4A and 4B, there is a battery 178 located below the circuit board 17 for accumulating electric power. This battery 178 is electrically connected to the circuit board 17 to accumulate electric power supplied through the terminal side connection terminal 11 in the battery 178 and supply electric power to the respective devices. Incidentally, between the battery 178 and the flexible printed circuit boards 175 and 176, there is a plate-like protection member 173 made of a nonconductive material such as a plastic material.

(Circuit Configuration of Each Device)

Figure 6:
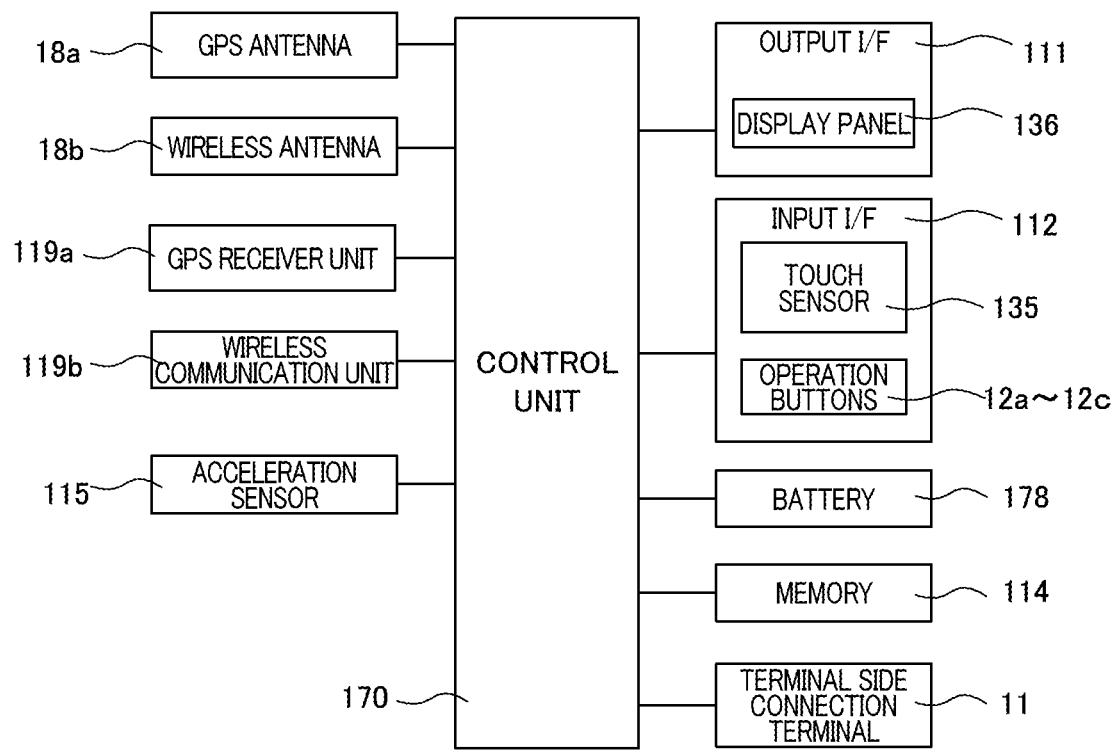
FIG. 6 is a block diagram for showing the circuit configuration of the wearing type terminal in accordance with the first embodiment.
Figure 7:
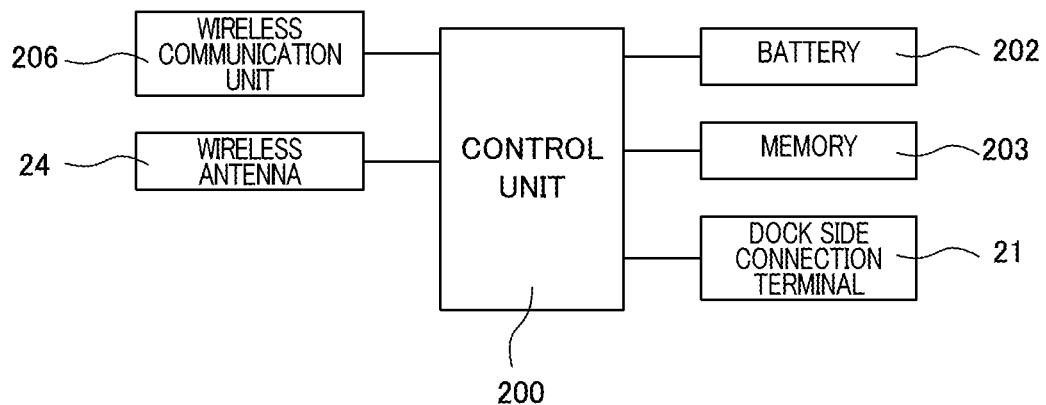
FIG. 7 is a block diagram for showing the circuit configuration of a docking type device in accordance with the first embodiment.

Next, the circuit configuration of each device will be explained. FIG. 6 is a block diagram for showing the circuit configuration of the wearing type terminal 1, and FIG. 7 is a block diagram for showing the circuit configuration of the docking type device 2.

(1) Circuit Configuration of Wearing Type Terminal 1

As illustrated in FIG. 6, the wearing type terminal 1 includes the control unit 170, an output interface 111, an input interface 112, the battery 178, a memory 114, the terminal side connection terminal 11, the acceleration sensor 115, the GPS antenna 18*a*, the wireless antenna 18*b*, the GPS receiver unit 119*a* and the wireless communication unit 119*b*.

The control unit 170 is an arithmetic operation module composed of hardware elements, for example, processor(s) such as a CPU and a DSP (Digital Signal Processor), a memory, and other necessary electronic circuits, software such as programs for implementing necessary functions of the hardware elements, or combination thereof.

Several function modules can be virtually implemented by loading and executing the programs so that a variety of processes are performed by the implemented function modules in response to the operation by the user. Meanwhile, in the case of the present embodiment, the control unit 170 acquires location information from the GPS on the basis of information acquired from a satellite, and is implemented with various programs running on information acquired from the acceleration sensor and information acquired from the wireless communication unit to display various types of information on the display unit 131.

The input interface 112 is a device for inputting user operations through the operation buttons 12*a* to 12*c*, the touch sensor 135 and the like. On the other hand, the output interface 111 is a device for outputting images through the display, and includes the display unit 131 such as an organic EL.

The battery 178 is a power accumulation device for accumulating electric power supplied through the connection terminal 21 of the docking type device 2 and the terminal side connection terminal 11 and supplies driving power to the display unit 131, the communication antenna 18 and the like. The memory 114 is a storage device for storing an OS (Operating System) and various application programs, and other data. In the case of the present embodiment, the memory 114 stores identification information for identifying the wearing type terminal 1, applications for displaying time, running or the like.

The acceleration sensor 115 is a sensor for measuring acceleration, and in the case of the present embodiment a small-sized acceleration sensor is used to which the MEMS (Micro Electro Mechanical System) is applied. This acceleration sensor 115 is capable of detecting acceleration in the X-axis direction corresponding to the lateral direction as seen from the front side of the wearing type terminal 1, the Y-axis direction corresponding to the vertical direction, and the Z-axis direction corresponding to the direction perpendicular to the display unit 131 of the wearing type terminal 1.

The wireless communication unit 119*b* is provided with the function to perform wireless communication on the basis of a data communication protocol such as BTLE, ANT or the like. It is possible by this data communication to perform data communication with outside and the sensors of the main body. For example, the wireless communication unit 119*b* performs data transmission and reception with an acceleration sensor, a temperature sensor and the like worn on a user to record body motions and health condition of the user and display positional information, external information and the like on the display unit 131. Incidentally, while BTLE is employed as a low power consumption communication protocol in the case of the present embodiment, ANT+ or the like protocol can be employed instead.

Also, in the case of the present embodiment, the wireless communication unit 119*b* includes a short-range communication interface for performing short range wireless communication on the basis of BTLE. In the case of the present embodiment, the wireless communication unit 119*b* is implemented by the use of a wireless communication device based on BTLE, ANT/ANT+ or the like as a low power consumption version of Bluetooth (registered trademark) to transmit and receive various data directly between devices through the wireless antenna 18*b* for transmitting and receiving electromagnetic waves in a predetermined frequency band within a short-range area, for example, transmitting log data stored in the wearing type terminal 1 to a personal computer or the like. Incidentally, this short-range wireless communication function may be implemented with a short-range communication interface of infrared communication, standard Bluetooth (registered trademark), UWB (Ultra Wide Band) communication or the like.

The GPS receiver unit 119*a* is a module for receiving signals from a GPS (Global Positioning System) satellite through the GPS antenna 18*a* to acquire satellite information such as satellite orbit information, GPS time information and positional information on the basis of GPS signals. This GPS receiver unit 119*a* receives GPS signals from a GPS satellite through the GPS antenna 18*a*, demodulates the signals, and then transmits the demodulated signals to the control unit 170, which acquires positioning information and time information in accordance with the demodulated signals.

On the other hand, the wireless communication unit 119*b* is a module for receiving BTLE signals through the wireless antenna 18*b* to transmit and receive data on the basis of a predetermined communication protocol.

(2) Circuit Configuration of Docking Type Device 2

As illustrated in FIG. 7, the docking type device 2 is provided with a control unit 200, a battery 202, a memory 203, the dock side connection terminal 21, a wireless communication unit 206, and the wireless antenna 24.

The control unit 200 is an arithmetic operation module composed of hardware elements, for example, processor(s) such as a CPU and a DSP (Digital Signal Processor), a memory, and other necessary electronic circuits, software such as programs for implementing necessary functions of the hardware elements, or combination thereof.

Several function modules can be virtually implemented by loading and executing the programs so that a variety of processes are performed by the implemented function modules in response to the operation by the user.

The battery 202 is a power accumulation device for accumulating electric power supplied from the power supply device 3 through the connection terminal 21 of the docking type device 2 and supplies driving power to the wireless antenna 24 and the like. The memory 203 is a storage device for storing firmware, programs of various applications and other data, for example, information of electronic money, identification information of the docking type device 2 and the like. Incidentally, the memory 203 may be used to store an OS (Operating System) or the like if necessary in the system.

The wireless communication unit 206 is provided with the function to perform wireless short-range communication on the basis of a protocol for data communication such as Bluetooth (registered trademark). Specifically, the wireless communication unit 206 is a device which performs reading and writing data from/to the memory 203 in a short-range area to enable data transmission and reception from/to a peripheral device such as a personal computer or a smartphone.

(Using Method)

Figure 8:
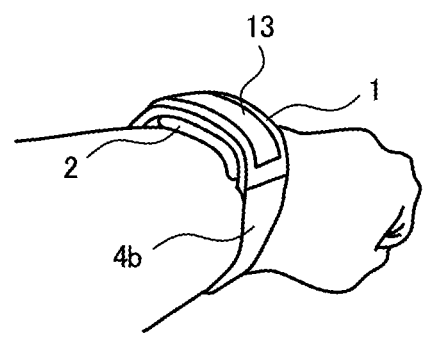
FIG. 8 is a perspective view for showing the information terminal device which is worn in accordance with the first embodiment.

The method of using the information terminal device 100 will be explained. FIG. 8 is a perspective view for showing the information terminal device which is worn in accordance with the first embodiment. As illustrated in FIG. 8, the information terminal device 100 is worn by winding the belt members 4*a* and 4*b* around an arm of a user. Then, the control unit 170 of the wearing type terminal 1 controls the display unit 131 to display time information by acquiring GPS signals with the GPS receiver unit 119. Also, the software for running is executed on the control unit 170 to display running information such as a running speed, a running distance, a running time, a running pace, a pitch (steps per minute), the number of steps and the like. At this time, the current location can be displayed in accordance with the GPS signals acquired through the GPS receiver unit 119. The current location can be displayed, for example, by displaying a mark on a map which may be simplified for the purpose of reducing the data size of the map or position indication on the basis of the difference of elevation.

Furthermore, for example, while the wearing type terminal 1 and the docking type device 2 are electrically connected through the dock side connection terminal 21, contactless wireless communication with outside can be performed by the use of the wireless communication unit 206 of the docking type device 2 to perform personal authentication or purchase an article with electronic money.

(Effect/Action)

In accordance with the first embodiment as described above, since the wearing type terminal having the display unit 131 is implemented with the function to display time information and the software for running, when only the wearing type terminal is worn, it is possible to use the wearing type terminal 1 as a watch and display the current location on a map during running. On the other hand, in the case where the docking type device 2 is implemented with a short-range communication function, and electronic money information is stored in the memory 203, it is possible to add an electronic money function to the information terminal device 100 by connecting the docking type device 2 with the wearing type terminal 1 so that running can be performed without carrying cash. In accordance with the present embodiment as described above, the convenience of users can be improved by combining devices having various functions, and attaching and detaching the devices in accordance with the use.

Also, in accordance with the present embodiment, the wireless antenna 24 of the docking type device 2 for use in short-range communication is arranged in order to overlap the back lid 19 of the external case 10 of the docking type device, and the GPS antennas 18 and 18 are arranged on the outer edges of the external case 10 in order not to overlap the wireless antenna 24, so that the GPS antennas 18 and 18 and the wireless antenna 24 can be prevented from causing radio wave interference therebetween, and therefore the signal reception performance can be prevented from being degraded.

Furthermore, in accordance with the present embodiment, the display unit 131 is curved in the direction connecting opposite sides to which the belt members 4*a* and 4*b* are connected, so that it is possible to improve the visibility of the display unit 131.

In the case of the present embodiment, the power supply device 3 is detachably connected to the bottom portion of the docking type device 2 to supply electric power through the dock side connection terminal 21 and the power supply device side connection terminal 31 so that it is possible to supply electric power to the wearing type terminal 1 and the docking type device 2 at the same time.

Still further, in accordance with the present embodiment, the power supply device 3 is provided with the USB terminal 33 for transmitting and receiving data from/to the wearing type terminal 1 or the docking type device 2 through the dock side connection terminal 21 and the power supply device side connection terminal 31, and capable of transmitting and receiving data from/to an external device through an external terminal which is provided outside the power supply device, and therefore it is possible to store various data from an external terminal such as a personal computer to the wearing type terminal 1 and the docking type device 2.

Second Embodiment

Figure 9:
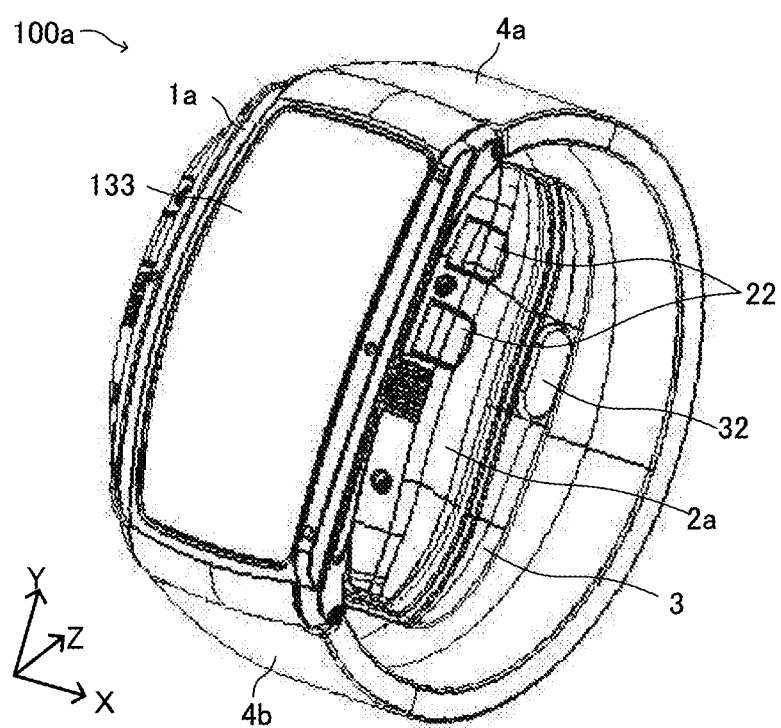
FIG. 9 is a perspective view for showing the overall configuration of an information terminal device in accordance with a second embodiment.
Figure 10:
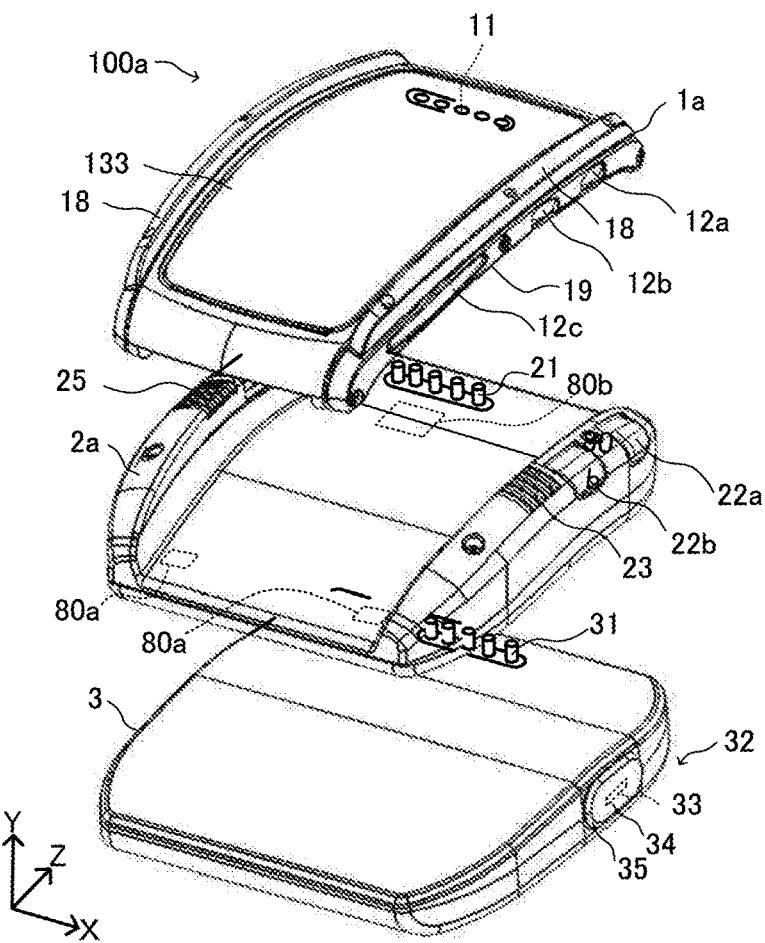
FIG. 10 is an exploded perspective view for showing the configuration of the information terminal device in accordance with the second embodiment.

Next, a second embodiment of the present invention will be explained. In the case of the present embodiment, a wearing type terminal 1*a* and a docking type device 2*a* having different configurations and functions than those of the first embodiment will be explained. FIG. 9 is a perspective view for showing the overall configuration of an information terminal device in accordance with the second embodiment, and FIG. 10 is an exploded perspective view for showing the configuration of the information terminal device in accordance with the second embodiment. Meanwhile, in the description of the following embodiments, like reference numbers indicate functionally similar elements as the above first embodiment unless otherwise specified, and therefore no redundant description is repeated.

The information terminal device 100a in accordance with the present embodiment consists of a wearing type terminal 1a, a docking type device 2a and a power supply device 3. Also in this embodiment, the wearing type terminal 1a is provided with an external case 10 having a display unit 133 on the upper surface side, and belt members 4a and 4b which can be connected to the both sides of the external case 10 respectively. The wearing type terminal 1a of the present embodiment differs in the profile of the display unit 133 than the wearing type terminal 1 of the first embodiment. The display unit 133 is curved in the direction connecting opposite sides to which the belt members 4a and 4b are connected (the Y-axis direction in FIG. 8). Specifically, the display unit 133 is formed in a generally rectangular shape with a long side in the direction connecting opposite sides to which the belt members 4a and 4b are connected such that an appropriately center portion thereof is curved in an arch shape to protrude outward.

The docking type device 2a is an information terminal device which is detachably coupled with the wearing type terminal 1a, and configured to output music and allow telephone conversations with a microphone 23 and a speaker 25 on the side of the case by electrically connecting with the wearing type terminal 1a as illustrated in FIG. 10. Also, the docking type device 2a is provided with operation buttons 22a and 22b so that, for example, a user can control start or end of telephone conversation and music playback by operating the operation buttons 22a and 22b. Furthermore, this docking type device 2a is provided with a built-in vibrator which notifies when a setting time comes (time report), a lap time of a stopwatch, an incoming report and other various alerts by vibration.

Meanwhile, in the case of the present embodiment, the wearing type terminal 1a and the docking type device 2a can be electrically connected through the dock side connection terminal 21, and the dock side connection terminal 21 and the terminal side connection terminal 11 are arranged in the same positions as those of the first embodiment. Namely, the docking type device 2a is formed with the dock side connection terminal 21, and detachably joined with a back lid 19 which is the bottom portion of the external case of the wearing type terminal 1a through the dock side connection terminal 21. Specifically, the back lid 19 which is the bottom portion of the wearing type terminal 1a is provided with a terminal side connection terminal 11 in a position corresponding to the dock side connection terminal 21 so that the docking type device 2a and the wearing type terminal 1a can electrically be connected to each other by connecting the dock side connection terminal 21 with the terminal side connection terminal 11. The wearing type terminal 1a and the docking type device 2a are then configured to transmit and receive data therebetween through this dock side connection terminal 21 for displaying the data on the display unit 133.

Also in the case of the present embodiment, the wearing type terminal 1a is provided with GPS antennas 18 and 18 which are arranged on the outer edges of the external case 10 respectively and arranged in order not to overlap a wireless antenna (second antenna) 24a provided in the docking type device 2a in a plan view.

In the case of the present embodiment, the wireless antenna 24 installed in the docking type device 2 is a short-range wireless communication antenna for performing wireless communication on the basis of a protocol for data communication such as Bluetooth (registered trademark), and configured to transmit and receive signals and data from/to an external device. It is therefore possible to connect an external device by the use of a high radio field intensity protocol.

This wireless antenna 24a is arranged in the same position as the wireless antenna 24 of the first embodiment. Specifically, this wireless antenna 24a is arranged in order to overlap the bottom portion of the external case 10 of the docking type device 2a in a plan view. The GPS antennas 18 and 18 installed in the wearing type terminal 1a are arranged in order not to interfere with the wireless antenna 24a.

(Circuit Configuration of Each Device)

Figure 11:
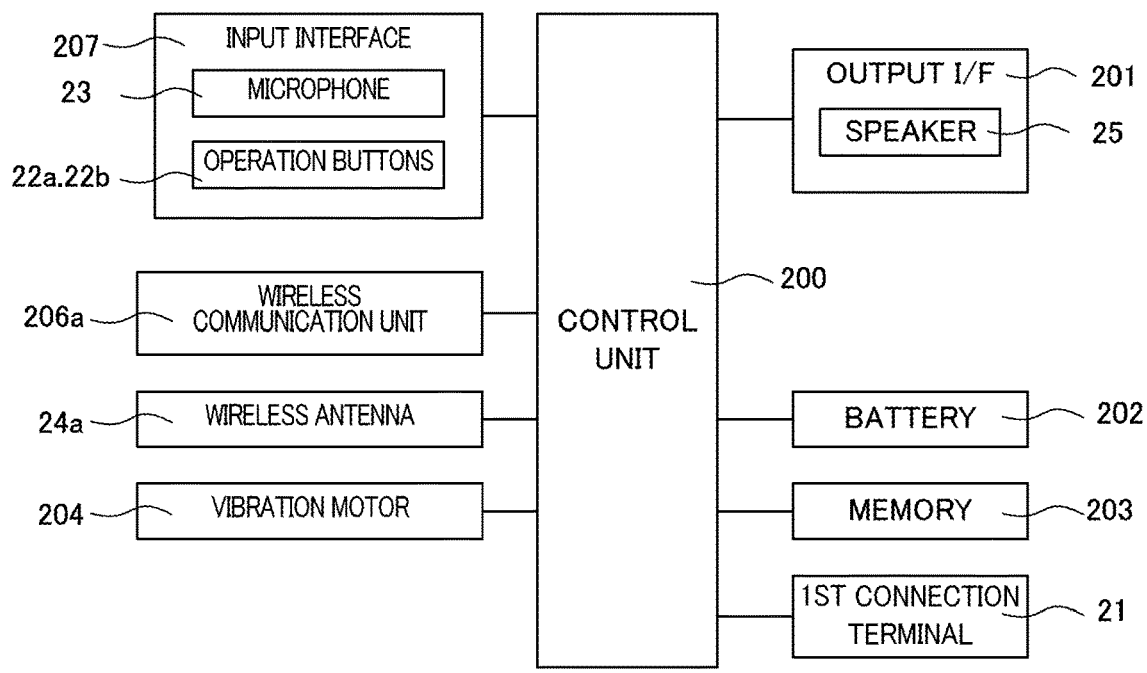
FIG. 11 is a block diagram for showing the circuit configuration of the docking type device in accordance with the second embodiment.

Next, the circuit configuration of the docking type device 2a will be explained. FIG. 11 is a block diagram for showing the circuit configuration of the docking type device 2a in accordance with the second embodiment. Incidentally, the wearing type terminal 1a has the same circuit configuration as the wearing type terminal 1 of the first embodiment, and therefore no redundant description is repeated. As illustrated in FIG. 11, the circuit configuration of the docking type device 2a includes a control unit 200, a battery 202, a memory 203, a dock side connection terminal 21, a wireless communication unit 206a, a wireless antenna 24a, a vibration motor 204 and an input interface 207.

The control unit 200 is an arithmetic operation module composed of hardware elements, for example, processor(s) such as a CPU and a DSP (Digital Signal Processor), a memory, and other necessary electronic circuits, software such as programs for implementing necessary functions of the hardware elements, or combination thereof. Several function modules can be virtually implemented by loading and executing the programs so that a variety of processes are performed by the implemented function modules in response to the operation by the user.

The input interface 207 is provided with devices for inputting user operations such as the operation buttons 22a and 22b, and the microphone 23 for acquiring sound. On the other hand, the output interface 201 is provided with the speaker 25 for outputting sound.

The battery 202 is a power accumulation device for accumulating electric power supplied from the power supply device 3 through the connection terminal 21 of the docking type device 2a and supplies driving power to the control unit 200, the wireless antenna 24a and the like. The memory 203 is a storage device for storing firmware, programs of various applications and other data, for example, information of electronic money, identification information of the docking type device 2a and the like. Incidentally, the memory 203 may be used to store an OS (Operating System) or the like if necessary in the system.

The wireless communication unit 206a is provided with the function to perform contactless communication on the basis of a protocol for data communication such as NFC to transmit and receive various data directly between devices through the wireless antenna 24a for transmitting and receiving electromagnetic waves in a predetermined frequency band within a short-range area. This wireless communication unit 206a can be used to receive image information from a terminal such as a smartphone possessed by a user, and transmit the image information to the wearing type terminal 1a through the dock side connection terminal 21. Incidentally, this short-range wireless communication function may be implemented with an interface of an infrared communication, a UWB (Ultra Wide Band) communication, a low power consumption wireless communication or the like.

Also, in the case of the present embodiment, the wireless communication unit 206a can make connection through the short-range communication of Bluetooth (registered trademark) to connect the docking type device 2 with a terminal device capable of performing wireless communication such as a personal computer, a smartphone or another electronic device. Furthermore, the wireless communication unit 206a is provided with a tethering function which makes it possible to connect with a communication network by using a terminal device connecting with the communication network as an external modem or a router.

The vibration motor 204 is a device for generating vibration to notify a user by the vibration, and consists for example of a rotary eccentric weight which rotates, when current is passed through the vibration motor 204, to generate vibration which is then transmitted to the arm of the user through the wearing type terminal 1a as a notification.

The information terminal device 100a consisting of the wearing type terminal 1a and the docking type device 2a is used by wearing the information terminal device 100a on an arm of a user in the same manner as in the first embodiment. Also in the case of the present embodiment, the control unit 170 of the wearing type terminal 1a controls the display unit 133 to display time information, and running information such as a running speed, a running distance, a running time, a running pace, a pitch (steps per minute), the number of steps and the like. Furthermore, the current location can be displayed in accordance with the GPS signals acquired through the GPS receiver unit 119.

Also, in the case of the present embodiment, for example, the vibration motor of the docking type device 2 can be vibrated under the control of software which is run by the control unit 170 of the wearing type terminal 1a, for example, to notify a user of measurement of a lap time by vibrating the vibration motor 204. Furthermore, in the case of the present embodiment, music data can be output through the speaker 25 of the docking type device 2a by performing wireless communication with a user terminal used by a user through the wireless communication unit 206a of the docking type device 2a, and also music data can be output through a headphone or the like by transmitting an operation signal for playing back the music data from the wearing type terminal 1a through the dock side connection terminal 21 and the terminal side connection terminal 11 to remotely operate an external music player. Also, for example, a Web page can be displayed on the display unit 133 by running browser software on a user terminal, processing the Web page by the browser software, receiving the Web page through the wireless communication unit 206a of Bluetooth (registered trademark) or the like and transmitting the Web page from the user terminal.

Furthermore, the positional information of own terminal and the positional information of another user can be displayed on a map by connecting with a communication network through the wireless communication unit 206a of the docking type device 2a, and receiving the positional information of the wearing type terminal possessed by this another user. Still further, by running an application of a social networking service, it is possible to display other users of the service near own position and communicate with the other users by using voice or text data.

(Effect/Action)

In accordance with the second embodiment as described above, there are the same effects and actions as in the above first embodiment. Furthermore, since the wireless communication unit 206a of the docking type device 2a has a short-range wireless communication function of Bluetooth (registered trademark), necessary data can be transmitted and received from/to the docking type device 2a and the wearing type terminal 1a by connecting the docking type device 2a with the wearing type terminal 1, and performing short-range wireless communication with an external user terminal used by the user. Also, a Web page can be displayed on the display unit 133 by running a browser software on the user terminal.

In accordance with the present embodiment as described above, the convenience of users can be improved by combining devices having various functions, and attaching and detaching the devices in accordance with the use. Also, in the case of the present embodiment, since the screen of the display unit 133 of the wearing type terminal 1a is curved, the viewing angle of the screen becomes wide by the curving amount to display images with a feeling of presence.

Third Embodiment

Next, a third embodiment of the present invention will be explained. The present embodiment is characterized in that Internet services can be received through the information terminal device 100 or 100a described above as the first or second embodiments. Namely, the present embodiment will be explained with a variety of services which can be received by cooperating with an application, which is running on an external user terminal, to access information on the Internet, participate an SNS (social networking service) and so forth through short range wireless communication of the wireless antenna 24 provided on the docking type device 2.

Figure 12:
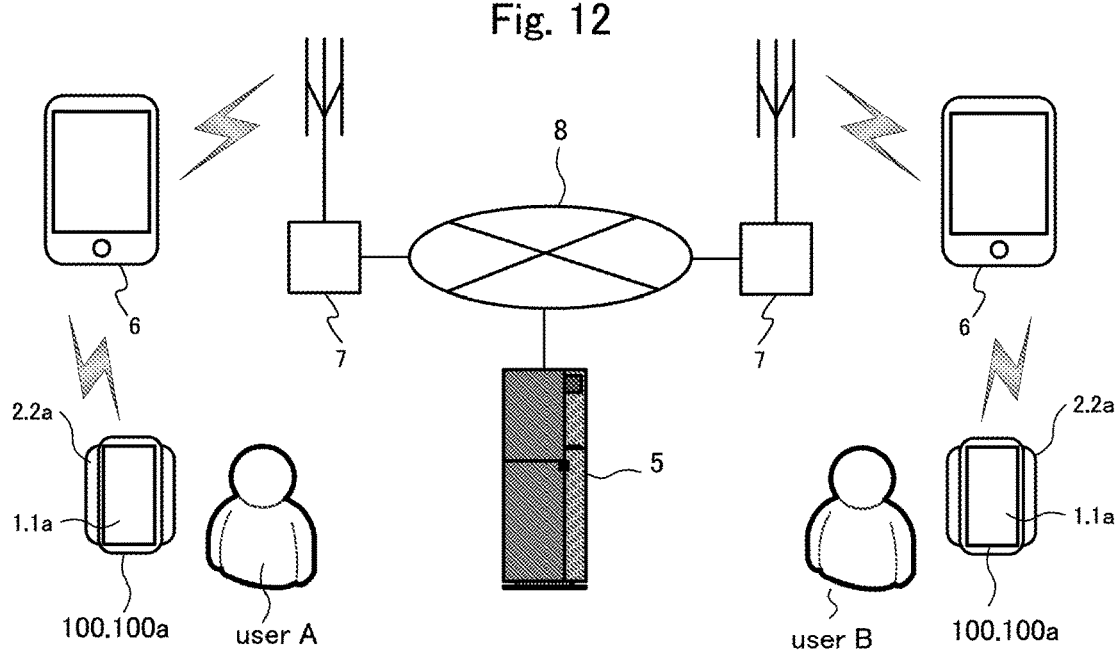
FIG. 12 is a view for schematically showing the configuration of an Internet service received by using an information terminal device in accordance with a third embodiment.

FIG. 12 is a view for schematically showing the configuration of an Internet service received by using the information terminal device 100 or 100a in accordance with the third embodiment. FIG. 13 and FIG. 14 are screen configuration views for schematically showing content displayed on the display screen of the respective devices in accordance with the third embodiment. Incidentally, in the description of the present embodiment, the information terminal devices 100 and 100a are referred to simply as the information terminal device 100.

In the case of the present embodiment, as illustrated in FIG. 12, the Internet service using the information terminal device 100 is implemented with a server device 5 and user terminals 6 used by user A and user B connected with a communication network 8 including wireless communication, and the information terminal devices 100 worn on user A and user B are connected with the user terminals 6 by using tethering.

The communication network 8 including wireless communication is a distributed communication network which is constructed by connecting a variety of communication lines (public lines such as a telephone line, an ISDN line, an ADSL line and an optical line, a 3G line, a 4G line, a dedicated communication line, and a wireless communication network) to each other by the use of the communication protocol TCP/IP. This communication network 8 may be a LAN such as an intranet (a network within a company), a home network, or the like based on 10BASE-T, 100BASE-TX or the like.

The server device 5 is implemented with a server computer or software capable of transmitting network content such as HTML (HyperText Markup Language) files, image files, music files and the like as a WWW (World Wide Web) document system, and serves to accumulate information such as HTML files and image files and deliver content (a Web page) in response to a request from an application such as a Web browser running on the user terminal 6. The server device 5 acquires positional information obtained from the information terminal device 100 through the user terminal 6, and delivers content (display data) for displaying the positional information of the users A and B.

The information terminal device 100 is worn on an arm of user A or user B, and at least the docking type device 2 or 2a are connected to the wearing type terminal 1 or 1a to enable tethering connection with the user terminal 6.

The user terminal 6 is a terminal, which is carried by a user, i.e., a cellular phone or a smartphone having an arithmetic processing capability by a CPU and a wireless communication capability to communicate with a relay point such as a usual base station and receive communication services such as telephone conversation, data communication and so forth while the user is moving. Also, the user terminal 6 is provided with the capability of performing wireless communication with a radio base station 7 and running an application. The communication system of this cellular phone may, for example, be an FDMA system, a TDMA system, a CDMA system, a W-CDMA system, a PHS (Personal Handyphone System) and the like. Furthermore, this user terminal 6 is implemented with a digital camera function, an application execution function, a GPS function and the like and serves also as a personal digital assistant (PDA).

Particularly, in the case of the present embodiment, the user terminal 6 is implemented with a short-range wireless communication function for performing tethering connection with the wireless antenna 24 and the wireless communication unit 206 of the docking type device 2, and receives GPS signals acquired by the GPS receiver unit 119a of the wearing type terminal 1 through the short-range wireless communication function.

In addition, the user terminal 6 is implemented with a wireless communication function for connecting the communication network 8 through the radio base station 7 to transmit GPS signals acquired by the GPS receiver unit 119a to the server device 5 on the communication network 8, receive content of the service including positional information of other users from the server device 5, and display the content on a screen 6a. Furthermore, the user terminal 6 is implemented with the function of converting the content acquired from the server device 5 to the content which can be displayed on the display unit 131 of the information terminal device 100, and transmitting the converted content to the information terminal device 100 by tethering connection. In this description, "the content which can be displayed on the display unit 131 of the information terminal device 100" means display information having a small data quantity showing only a summary of the service from among the content displayed on the user terminal 6.

Figure 13A:
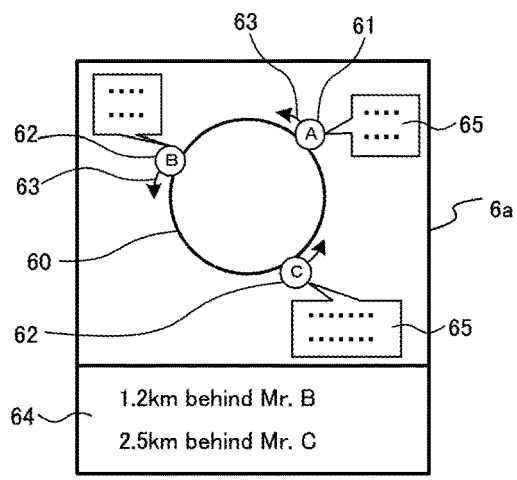
FIG. 13A and FIG. 13B are screen configuration views for showing content displayed on the display screens of respective devices in accordance with the third embodiment.
Figure 13B:
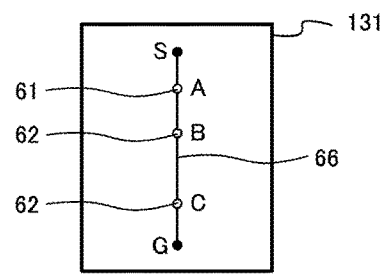
Figure 14A:
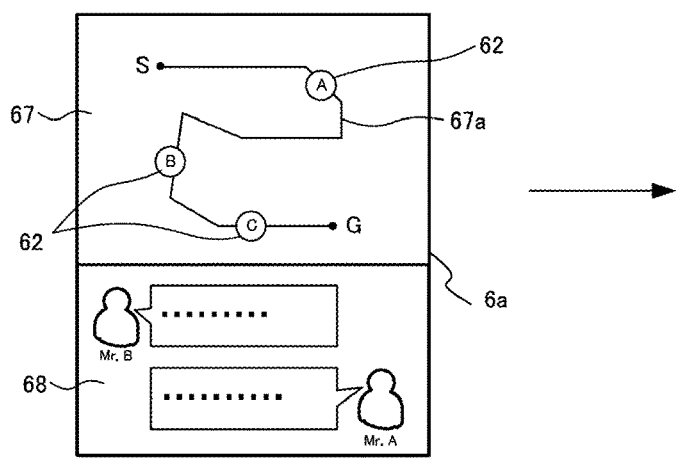
FIG. 14A and FIG. 14B are screen configuration views for showing content displayed on the display screens of respective devices in accordance with the third embodiment.
Figure 14B:
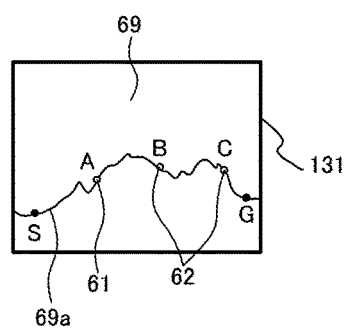

Next, the content to be displayed on the user terminal 6 and the information terminal device 100 will be specifically described. Incidentally, this example is explained in the case where user A and user B communicate with other users, while running, by accessing the Internet and participating an SNS with the information terminal device 100 and the user terminal 6. FIG. 13A and FIG. 14A are screen configuration views for showing content displayed on the display screen of the user terminal 6 used by user A, and FIG. 13B and FIG. 14B are screen configuration views for showing content displayed on the display unit 131 of the information terminal device 100.

(1) Screen Configuration 1

First is an explanation in the case where user A and B perform running or cycling around the imperial palace or in a track of an athletics stadium. In this case, a loop running course 60 as shown in FIG. 13A is selected by accessing the server device 5 and selecting the course for running. The communication function of the user terminal 6 is connected with the information terminal device 100 by tethering in advance to acquire GPS signals acquired through the GPS receiver unit 119a, and then transmits the GPS signals when accessing the server device 5.

The server device 5 acquires GPS signals from the user terminal 6 of each user at every predetermined time or on a real time base, and transmits content in which the position of each user is indicated on the loop running course 60 to the user terminal 6. When the user terminal 6 receives such content, the loop running course 60 is displayed on the display screen 6a, as illustrated in FIG. 13A, with an object 61 indicating own position (user A) and objects 62 indicating the positions of other users B and C participating an SNS service. Also, in this screen, arrow icons 63 may be displayed to indicate running directions.

Also, in the case of the present embodiment, the server device 5 measures the distances from the other users, and transmits information about the distances. Namely, the user terminal 6 displays information 64 which indicates the distance between own position and the position of each of the other users B and C at the bottom of the screen.

Furthermore, text is input by the use of an input device of the user terminal 6 and temporarily transmitted to the server device 5. The server device 5 acquires the text data, and then simultaneously transmits the text data to the user terminals 6 which are grouped. Each user terminal 6 thereby displays, on the screen, text input by own user and text input by other users in comment boxes 65.

On the other hand, the content displayed on the display unit 131 of the information terminal device 100 is content indicating only the position of each user on the running course as illustrated in FIG. 13B. Specifically, as illustrated in FIG. 13B, a linear running course 66 is displayed by connecting a start position and a goal position which correspond to the start position and the goal position of the loop running course 60 respectively, and the position of each user is displayed on the linear running course 66 as objects 61 and 62.

An application of the user terminal 6 is executed to obtain such content by converting the content acquired of the server device 5. The converted content is transmitted to the docking type device 2 by tethering connection between the user terminal 6 and the wireless antenna 24 (the wireless communication unit 206) of the docking type device 2. Then, the docking type device 2 transmit the content to the wearing type terminal 1 through the connection terminal to display the content showing only a summary on the display unit 131 of the information terminal device 100. While the user terminal 6 converts the content in this example, the server device 5 can generate the content for the information terminal device 100 by conversion in advance, and deliver the generated content.

(2) Screen Configuration 2

Next is an explanation of another screen configuration, for example, in the case where users run a marathon on a public road as a course. At first, a course is selected by accessing the server device 5 with the user terminal 6 to select a course map 67 as shown in FIG. 14A. Also in this case, the communication function of the user terminal 6 is connected with the information terminal device 100 by tethering in advance to acquire GPS signals, and then transmits the GPS signals when accessing the server device 5. The server device 5 acquires the GPS signals of user A and other users B and C at every predetermined time or on a real time base, generates content in which the position of each user is indicated on a running course 67a of the course map, and transmit the content to each user terminal 6. When the user terminal 6 receives such content, the course map 67 is displayed as illustrated in FIG. 14A with an object 61 indicating own position and objects 62 indicating the positions of other users B and C on the running course 67a.

Also, in this example, when text is input to the comment area 68 by the use of an input device of the user terminal 6, the text is simultaneously transmitted to each user terminal 6 through the server device 5, and the text input by each user in a group is displayed in a comment area at the bottom of the screen.

Next is an explanation of the content displayed on the display unit 131 of the information terminal device 100 in the above case. In the case where a course of running on a public road is selected as in the present embodiment, as illustrated in FIG. 14B, a height difference chart 69 can be displayed on the display unit 131 of the information terminal device 100 to indicate the height difference of the course. Also in this height difference chart 69, the running course 69a is displayed with an object 61 indicating own position and objects 62 indicating the positions of other users. The conversion of the content to be displayed on this display unit 131 may be performed at the user terminal 6 or at the server device 5.

In accordance with the third embodiment, the information terminal device 100 can be connected with the user terminal 6 such as a smartphone or a tablet PC by the use of a high radio field intensity protocol through the wireless communication capability of the docking type device 2. It is therefore possible to cooperate with an application executed by the user terminal 6 to access information on the Internet, participate an SNS (social networking service) and receive a variety of services. Incidentally, needless to say, the screen configuration of content as shown in FIG. 13 and FIG. 14 is only illustrative, but a variety of content can be displayed in accordance with a variety of services on the Internet.

Fourth Embodiment

Next, a fourth embodiment of the present invention will be explained. The present embodiment is characterized in that a motion capture system for detecting the body motions of a wearer is provided by the use of various sensors worn on the wearer and the information terminal device 100 or 100a described above as the first or second embodiments.

Figure 15A:
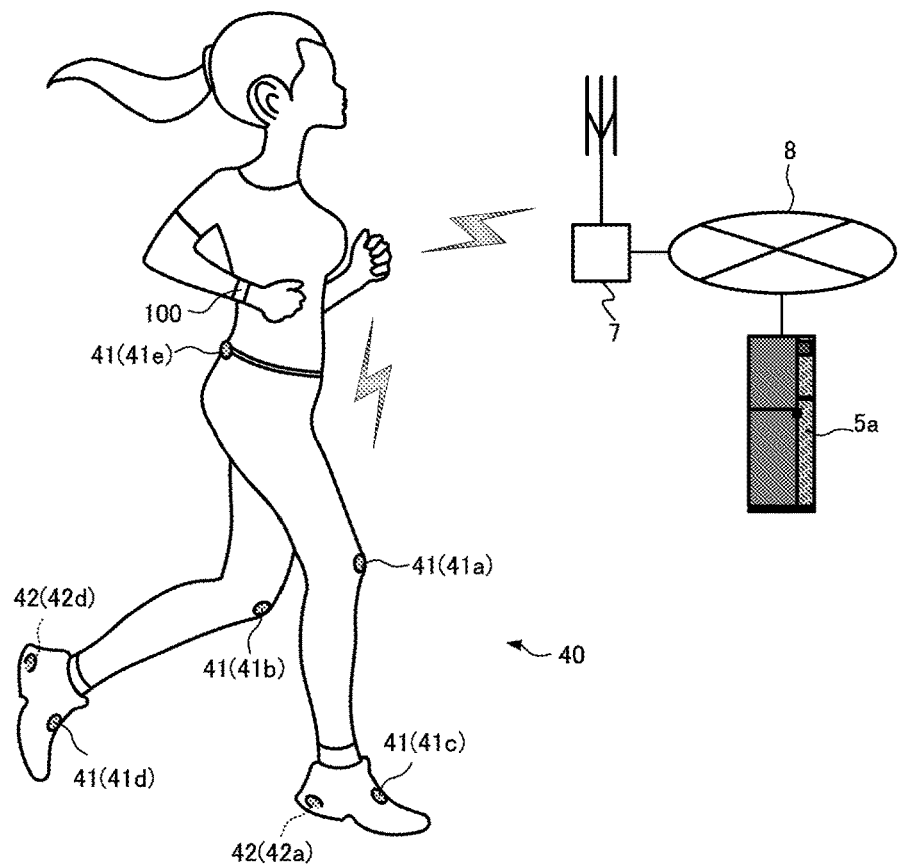
FIG. 15A is a view for schematically showing the configuration of the motion capture system in accordance with a fourth embodiment.
Figure 15B:
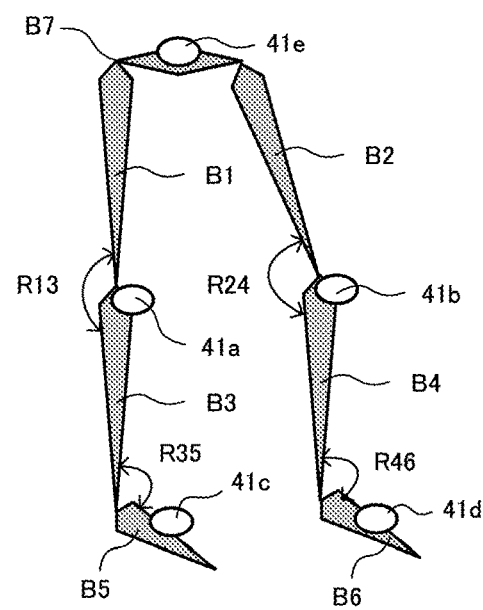
FIG. 15B shows one example of body motion reproduction data which is acquired in accordance with the present embodiment.
Figure 16:
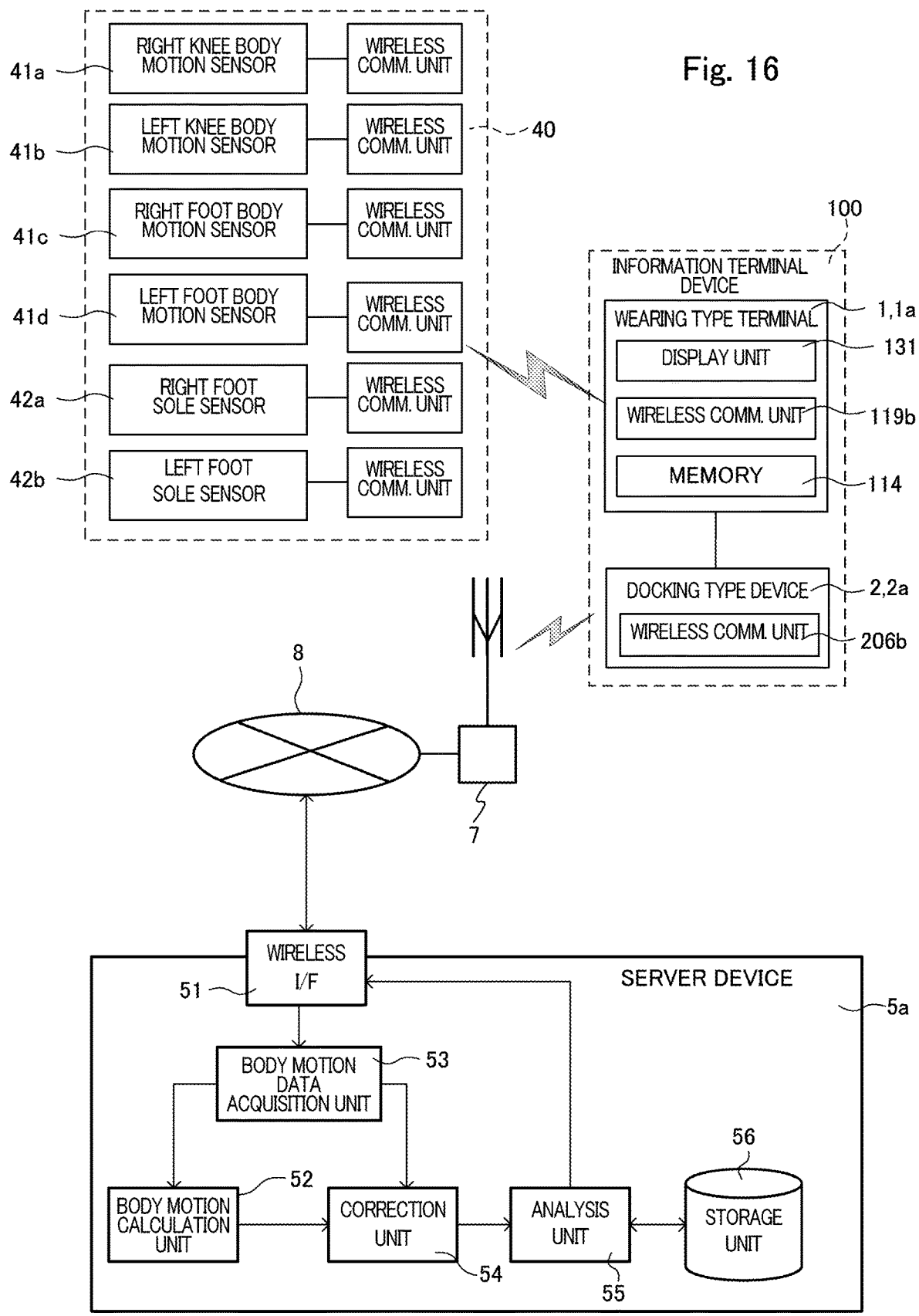
FIG. 16 is a block diagram for showing the internal structure of the respective devices in accordance with the fourth embodiment.

FIG. 15A is a view for schematically showing the configuration of the motion capture system implemented with the information terminal device 100 or 100a in accordance with the fourth embodiment, and FIG. 15B shows one example of body motion reproduction data which is acquired by the motion capture system in accordance with the present embodiment. Also, FIG. 16 is a block diagram for showing the internal structure of the respective devices in accordance with the fourth embodiment. Incidentally, in the following description (the present embodiment and the following modified examples), the information terminal devices 100 and 100a are referred to as simply the information terminal device 100.

As illustrated in FIG. 15A and FIG. 16, the motion capture system of the present embodiment is implemented with a communication network 8 including wireless communication, a server device 5a on the communication network 8, the information terminal device 100 worn on a predetermined wearer, and various sensors 40 which are worn on the predetermined wearer and connected to the information terminal device 100 by tethering connection.

The various sensors 40 are a group of sensors detachably attached to the wearer and include body motion sensors 41 and sole sensors 42. The body motion sensors 41 are a group of sensors which are worn on respective parts of the body of the wearer to detect the three-dimensional displacement and acceleration of each part. In the case of the present embodiment, the body motion sensors 41 are worn on predetermined joints of the wearer. Specifically, the body motion sensors 41 include a right knee body motion sensor 41a worn on the right knee of the wearer, a left knee body motion sensor 41b worn on the left knee of the wearer, a right foot body motion sensor 41c worn on the instep of the right foot of the wearer, a left foot body motion sensor 41d worn on the instep of the left foot of the wearer, and a waist body motion sensor 41e worn on the waist of the wearer. Each motion sensor 41 incorporates a three-axis acceleration meter for measuring the acceleration of an object, a three-axis gyroscope for measuring the angular speed of the object, a three-axis magnetic sensor for measuring the magnitude and direction of a magnetic field, so that motions about nine axes can be detected.

Each motion sensor 41 can be detachably worn on the clothing of a wearer or detachably attached as a belt or clothing. By this configuration, a wearer can attach each sensor to a belt or clothing in the feelings of daily life when attaching a small article to a belt or clothing, or wearing a belt or clothing, so that it is possible to perform continuous measurement without putting burdens on the wearer.

On the other hand, the sole sensors 42 are attached to the shoe soles of a wearer to detect the pressures exerted on the shoe soles. In the case of the present embodiment, the sole sensors 42 include a right foot sole sensor 42a attached to the sole for the right foot, and a left foot sole sensor 42b attached to the sole for the left foot. The sole sensor 42 is responsible for acquiring a force which is exerted when the wearer comes in contact with a contact surface such as a floor, and can be implemented with a tactile sensor and a force sensor. Alternatively, the sole sensor 42 may be implemented with a distribution tactile sensor which is flexible and lightweight not to become a hindrance to contacting motion and is made for example of a pressure sensitive rubber, a pressure sensitive fabric or the like. Examples of a tactile sensor may be formed of a pressure sensitive resistor, a capacitor, an imaging device, a light diffusion system, an inductance, an EIT system, a strain gauge, a MEMS sensor and the like, but the present invention is not limited thereto. The EIT system is a system for reconstructing pressure distribution by forming electrodes in the periphery of a material (pressure sensitive rubber, pressure sensitive fabric) whose resistance is changed in accordance with a pressure applied thereto, applying a voltage to two arbitrary points, measuring the voltages of the other electrodes, and performing an analysis of inversion problems to realize an elastic tactile sensor.

The sole sensor 42 can be detachably worn on a wearer as a footwear. Alternatively, the sole sensor 42 can be embedded in the bottom portion of a shoe or a sandal in an integral fashion, or can be formed as a separate member such as an insole for a footwear. Furthermore, the sole sensor 42 can be formed as a wearable member such as a sock.

Each of the sensors 40 (the body motion sensors 41 and the sole sensors 42) is provided with a wireless communication unit as illustrated in FIG. 16. This wireless communication unit incorporates an antenna and can perform a communication process with the wearing type terminal 1 or 1a (hereinafter the wearing type terminal 1 and the wearing type terminal 1a are referred to simply as the wearing type terminal 1) by the function to perform wireless communication on the basis of a data communication protocol such as BTLE. Meanwhile, while the wireless communication unit of each sensor 40 uses BTLE as a low power consumption communication protocol in the case of the present embodiment, ANT, ANT+ or the like protocol can be employed instead.

Alternatively, standard Bluetooth (registered trademark) can be employed instead.

In addition to the functions of the above embodiments, the information terminal device 100 has the function to collect detection results obtained by each sensor 40, and obtains the detection results by a communication process between each sensor 40 and the wireless communication unit 119b of the wearing type terminal 1 as described above.

The memory 114 of the information terminal device 100 serves as a body motion recording unit which can accumulate the detection results of the body motion sensors 41 and the sole sensors 42 as body motion data. Incidentally, the detection results as transmitted from each sensor 40 include sensor identification information which is added for identifying this each sensor 40 and accumulated in the memory 114 of the information terminal device 100 so that when acquiring the detection result through the wireless communication unit 119b, the control unit 170 can determine which sensor 40 outputs that detection result. Also, this identification information of each sensor includes wearing part identification information for identifying the part on which this each sensor is worn, and body motion reproduction data can be calculated on the basis of this wearing part identification information. Furthermore, the body motion data includes time information when the detection result is acquired from each sensor 40.

In addition, the information terminal device 100 has the function to transmit the acquired body motion data to the server device 5a of the communication network 8. Specifically, the body motion data recorded by the wearing type terminal 1 is transmitted to the docking type device 2 through the dock side connection terminal 21 and the terminal side connection terminal 11. The wireless communication unit 206 of the docking type device 2 or 2a (hereinafter the docking type device 2 and the docking type device 2a are referred to simply as the docking type device 2 respectively) then transmits the acquired body motion data to the server device 5a.

Furthermore, the display unit 131 of the information terminal device 100 serves as an output device which displays or outputs an analysis result of body motion reproduction data by acquiring the analysis result from the server device 5a and displaying the analysis result under the control of the control unit 170. Meanwhile, in the case of the present embodiment, the other function modules of the information terminal device 100 are the same as in either of the first embodiment through the third embodiment, and therefore no redundant description or illustration in FIG. 16 is repeated.

In the same manner as the server device 5, the server device 5a is implemented with a server computer or software capable of transmitting network content such as HTML (HyperText Markup Language) files, image files, music files and the like as a WWW (World Wide Web) document system, and serves to accumulate information such as HTML files and image files and deliver content (a Web page) in response to a request from an application such as a Web browser running on the user terminal 6. Furthermore, the server device 5a of the present embodiment has the function to analyze the body motions of a wearer on the basis of body motion data acquired from the information terminal device 100, and generate the body motion reproduction data as illustrated in FIG. 15B. Specifically, as illustrated in FIG. 16, the server device 5a is provided with a communication interface 51, a body motion data acquisition unit 53, a body motion calculation unit 52, a correction unit 54, an analysis unit 55 and a storage unit 56.

The communication interface 51 is a module for controlling transmission and reception of various information through the communication network 8 to transmit and receive data from/to the docking type device 2 of the information terminal device 100 by one of various protocols. In the case of the present embodiment, the communication interface 51 is used to acquire body motion data from the docking type device 2, and transmit the analysis result obtained by the analysis unit 55 to the information terminal device 100.

The body motion data acquisition unit 53 is a module for acquiring body motion data from the information terminal device 100 through the communication network 8. In the case of the present embodiment, the body motion data acquisition unit 53 acquires the detection result of each sensor 40 as body motion data by performing wireless communication with the wireless communication unit 206 of the docking type device 2. This body motion data is temporarily accumulated in a storage device, and then the detection results of the body motion sensors 41 are transmitted to the body motion calculation unit 52. Also, the detection results of the sole sensors 42 are transmitted to the correction unit 54.

The body motion calculation unit 52 is a module for calculating body motions of a wearer as body motion reproduction data on the basis of the detection results of the body motion sensors 41 accumulated in the memory 114 (body motion recording unit) and the relative positional relationship among the body motion sensors 41.

In this case, the detection results of the body motion sensors 41 are values which are measured with a so-called nine-axis sensor and, in the case of the present embodiment, include the direction and magnitude of acceleration (including gravitational acceleration) of an object, an angular velocity (magnitude, direction and center position) of the object, and the direction (orientation) and magnitude of a magnetic field. The relative positional relationship of the body motion sensors 41 is represented by the mutual distances thereamong and movable ranges which are determined by the skeleton of a wearer and the positions of the body motion sensors 41, which are worn on the wearer. For example, as illustrated in FIG. 15B, the lower half of a human body consists of a pelvis B7, a pair of thighbones B1 and B2 connected to the pelvis B7, tibias B3 and B4 connected to the thighbones B1 and B2 respectively, and tarsal bones B5 and B6 further connected to the tibias B3 and B4 respectively. Each bone is bendably or pivotally connected with a joint, but hardly changes its length. Also, the bending angles R13, R24, R35 and R46 of respective joints have limited movable ranges respectively. Accordingly, body motion reproduction data for reproducing the motion and posture of a wearer can be generated from the relative positional relationship among the body motion sensors and the detection results of the body motion sensors determined by the lengths of the bones and the movable ranges of the joints.

The correction unit 54 is a module for correcting the body motion reproduction data calculated by the body motion calculation unit 52 on the basis of the detection results of the sole sensors 42. In the correction process by the correction unit 54, the body motion sensors 41 as described above calculate the entire displacements and rotations by continuously accumulating the value measured by each sensor. However, since noise and error occurring in the detection results of the sensors are accumulated, there may be deviation from actual positions, displacements and postures. Because of this, in the case of the present embodiment, it is determined that a shoe sole comes in perfect contact with the ground the moment the detection result of the sole sensors 42 reaches a maximum value. The correction unit 54 corrects the height of the body motion sensor 41$c$ or 41$d$ worn on the foot indicating the maximum value to be zero, and corrects the positions and rotation angles of the other bones B1 to B4 and B7 with reference to the tarsal bone B5 or B6 corresponding to the height of zero.

The analysis unit 55 is a module for analyzing body motions of a wearer on the basis of the body motion reproduction data corrected by the correction unit 54. This analysis method may be performed to generate stereoscopic image data for three-dimensionally displaying a wearer on the basis of the body motion reproduction data after correction. And, improved data indicating displacements from normal body motions may be generated by extracting representative body motion data from the storage unit 56 which accumulates representative body motion data, comparing the body motion reproduction data of a wearer with the representative body motion data. Furthermore, the analysis can be performed on the basis of user information by registering user information such as gender, height, weight and age. The analysis unit 55 then transmits the analysis results such as the stereoscopic image data, the improved data and the like to the information terminal device 100.

The storage unit 56 is a storage unit for accumulating various data such as the identification information for identifying each information terminal device 100, the wearing part identification information of each sensor 40, the relative positional relationship of the body motion sensors 41 worn on the respective parts, the user information, the representative body motion data and the like.

(Motion Capture Method)

Figure 17:
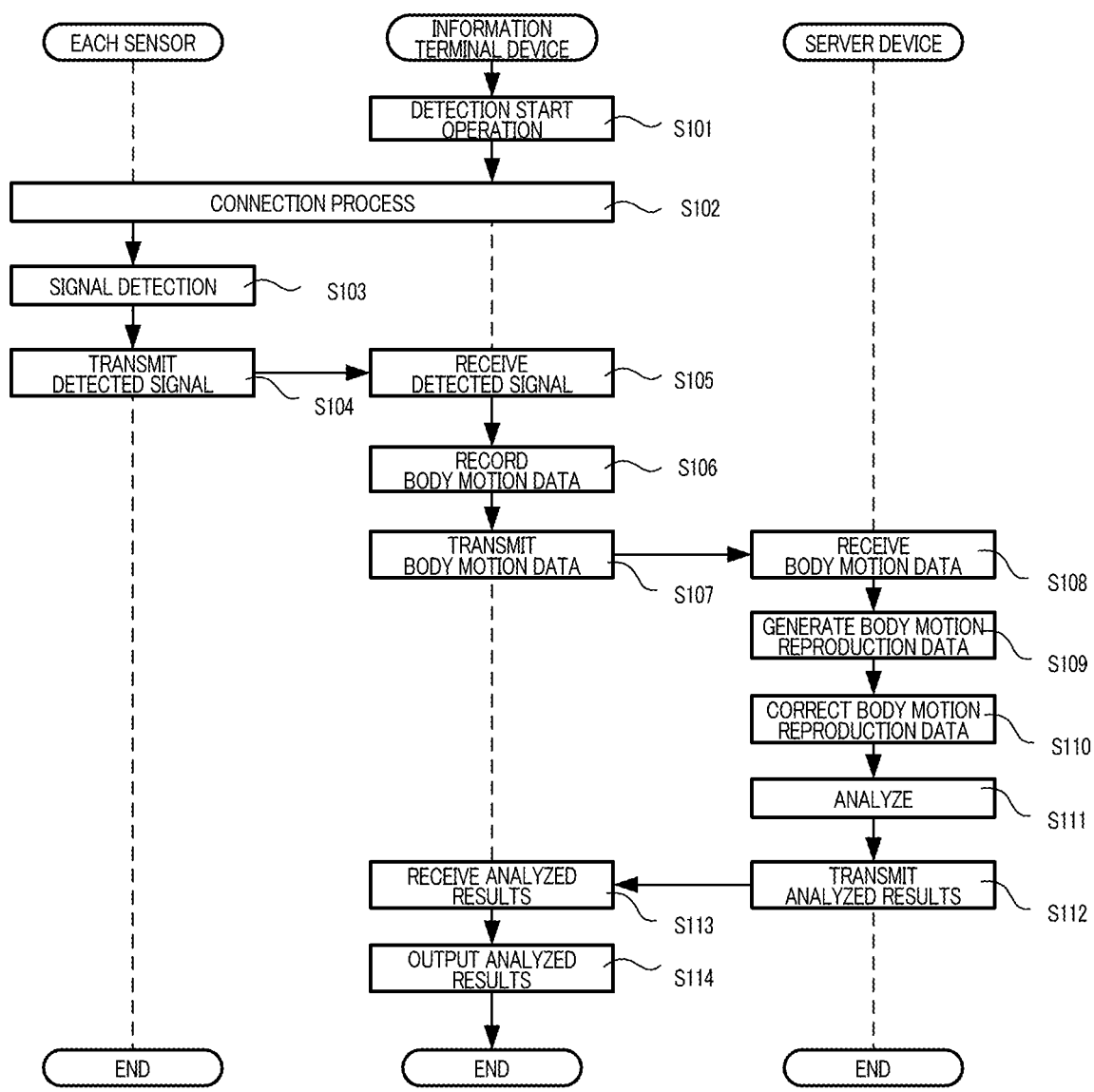
FIG. 17 is a sequence diagram for showing the motion capture method in accordance with the fourth embodiment.

The motion capture method in accordance with the present invention can be implemented by operating the motion capture system having the structure as described above. FIG. 17 is a sequence diagram for showing the motion capture method in accordance with the fourth embodiment.

First, a wearer wears the body motion sensors 41 on both knees and both feet, and wears the sole sensors 42 on the shoe soles. Also, the wearer wears the information terminal device 100 on an arm. The information terminal device 100 is then operated to acquire detection results from the sensors 40 (S101).

When acquiring an operation signal, the control unit 170 of the wearing type terminal 1 performs a connection process with each sensor 40 (S102). After performing the connection process, each sensor 40 detects the motion of the wearer. Specifically, three-dimensional displacements or accelerations at each part of the wearer are detected by the body motion sensor 41 worn on this each part, and the pressures exerted on the sole are detected by the sole sensors 42 placed in the sole of the wearer.

Then, the detection results which are acquired are transmitted to the wireless communication unit 119$b$ of the wearing type terminal 1 from the wireless communication unit of each sensor 40 by using weak electric waves (S104). When the wireless communication unit 119$b$ of the wearing type terminal 1 acquires the detection results (S105), the memory 114 of the wearing type terminal 1 serving as a body motion recording unit accumulates the detection results of the body motion sensors 41 and the sole sensors 42 as body motion data (S106).

The wearing type terminal 1 then transmits the body motion data stored in the wearing type terminal 1 to the docking type device 2 through the dock side connection terminal 21 and the terminal side connection terminal 11. The wireless communication unit 206 of the docking type device 2 then transmits the acquired body motion data to the server device 5$a$ (S107).

After the body motion data acquisition unit 53 of the server device 5$a$ acquires body motion data (S108), the detection results of the body motion sensors 41 are transmitted to the body motion calculation unit 52, and the detection results of the sole sensors 42 are transmitted to the correction unit 54. The body motion calculation unit 52 calculates body motions of the wearer as body motion reproduction data on the basis of the detection results of the body motion sensors 41 accumulated in the body motion recording unit and the relative positional relationship among the body motion sensors 41 (S109), and transmits the body motion reproduction data to the correction unit. On the other hand, the correction unit 54 corrects the body motion reproduction data calculated by the body motion calculation unit 52 on the basis of the detection results of the sole sensors 42 (S110). The corrected body motion reproduction data is then transmitted to the analysis unit 55.

The analysis unit 55 analyzes the body motions of the wearer on the basis of the body motion reproduction data which is corrected by the correction unit 54 (S111). The analyzed analysis result data is transmitted to the information terminal device 100 through the communication interface 51 (S112).

When receiving the analysis result data (S113), the docking type device 2 of the information terminal device 100 transmits this data to the wearing type terminal 1 through the dock side connection terminal 21 and the terminal side connection terminal 11. The control unit 170 of the wearing type terminal 1 has the display unit 131 display or output the acquired analysis results of the analysis unit 55 (S114).

(Effect/Action)

In accordance with the present embodiment as discussed above, it is possible to let a wearer recognize body motions of the wearer herself, and advise improvement of the body motions of the wearer, by attaching the body motion sensors 41 and the sole sensors 42 to the body of the wearer, calculating the body motions of the wearer as body motion reproduction data on the basis of the detection results of the sensors 40, analyzing the body motion reproduction data, and displaying the analysis results on the display unit 131.

At this time, since the correction unit 54 corrects the body motion reproduction data calculated by the body motion calculation unit 52 on the basis of the detection results of the sole sensors 42, even when a deviation occurs in the relative position of the body motion reproduction data to the ground due to noise and error occurring in the detection results of the body motion sensors 41 such as nine-axis sensors, it is possible to appropriately build, display and output the body motion reproduction data by making use of the timing detected by the sole sensors 42 when the sole comes in contact with a floor to correct the value of each body sensor 41 (for example, zero correction).

Also, in the case of the present embodiment, since the memory 114 of the information terminal device 100 serves as a body motion recording unit which accumulates the detection results of the body motion sensors and the sole sensors as body motion data, it is possible to make the device for accumulating body motion data in the form of a wearable watch type device having excellent portability and easily collect body motion data while performing exercise and sports.

Furthermore, in the case of the present embodiment, the wireless communication unit 119b of the wearing type terminal 1 uses a wireless communication system such as Bluetooth (registered trademark), BTLE or ANT. Meanwhile, since the number of devices which can be simultaneously connected is limited in such a wireless communication system (up to a maximum of 6 in the case of Bluetooth (registered trademark)), in the case of the present embodiment, the body motion reproduction data is calculated by the use of six sensors 40 in total, i.e., four body sensors 41 worn on both knees and both feet of the wearer and two sole sensors 42 attached to the soles of both shoes for the purpose of makes it possible to calculate and analyze the body motion reproduction data of the wearer with the minimal number of sensors. As a result, in accordance with the present embodiment, it is possible to calculate and analyze the body motion reproduction data of a wearer without changing the structure of the information terminal device 100 of the embodiments as described above.

Modified Example 1

Figure 18:
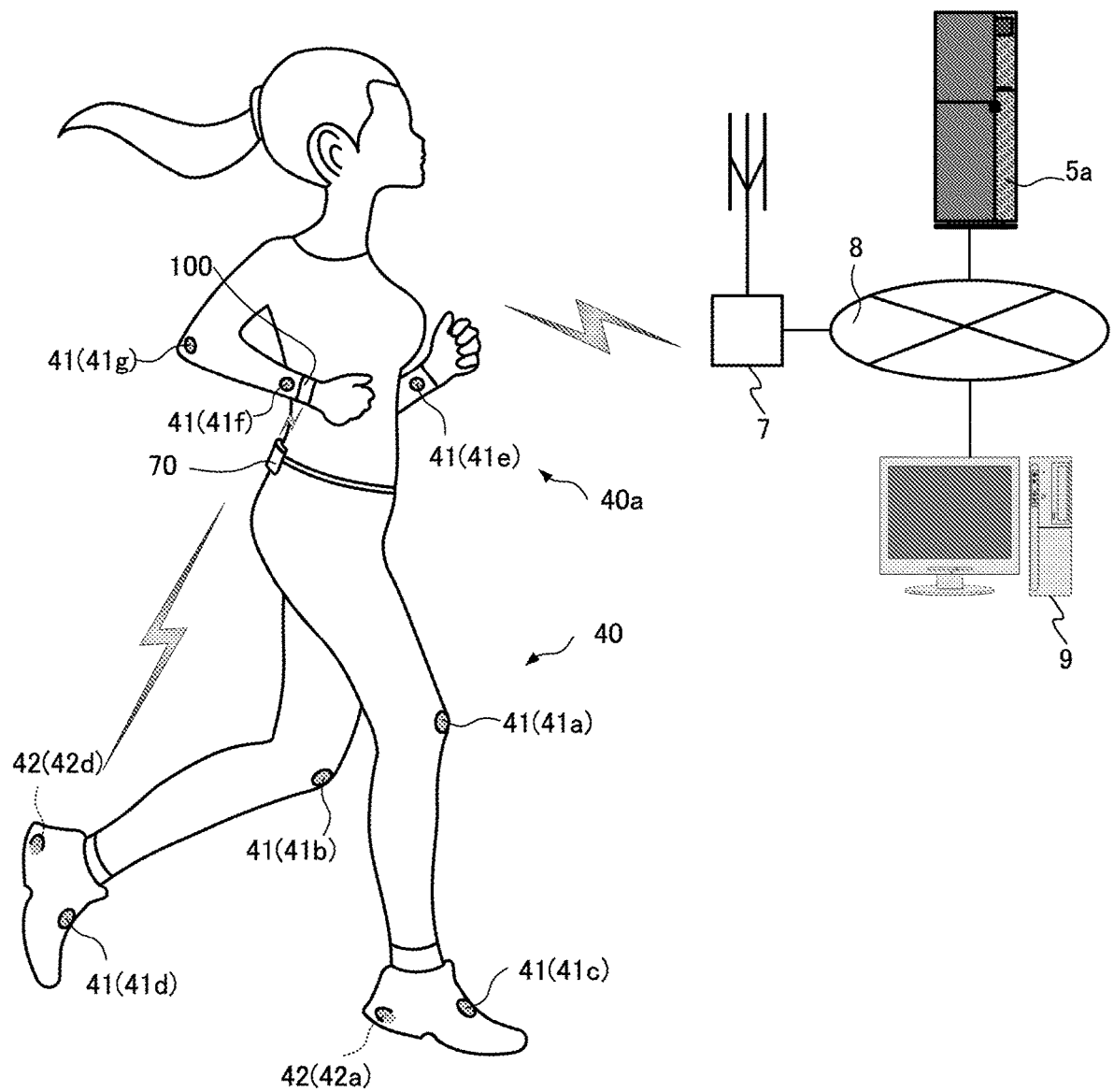
FIG. 18 is a view for schematically showing the configuration of the motion capture system in accordance with a modified example 1.
Figure 19:
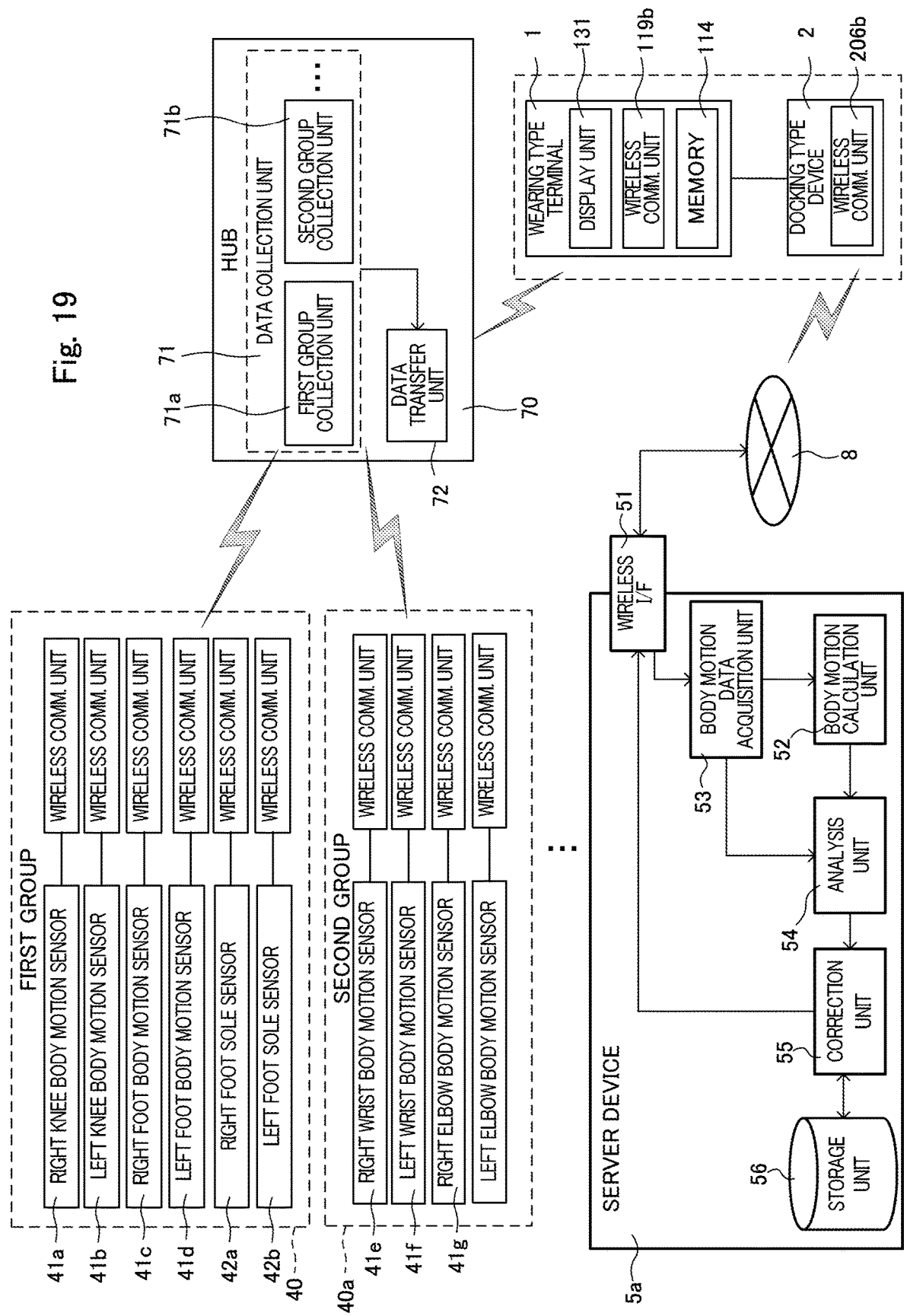
FIG. 19 is a block diagram for showing the internal structures of respective devices in accordance with the modified example 1.

Next is an explanation of a modified example 1 of the fourth embodiment as described above. While the body motion sensors 41 are worn on the six parts of both knees and both feet in total in the case of the fourth embodiment of the present invention as described above, further body motion sensors 41 are worn on other parts in the present modified example 1. FIG. 18 is a view for schematically showing the configuration of the motion capture system in accordance with the present modified example 1, and FIG. 19 is a block diagram for showing the internal structures of the devices in accordance with the present modified example 1. Meanwhile, in the description of the following modified example, like reference numbers indicate functionally similar elements as the above embodiments unless otherwise specified, and therefore no redundant description is repeated.

The motion capture system in accordance with the present modified example 1 is implemented with a plurality of body motion sensors 41 which are worn on the upper half of a wearer, and a hub 70 which performs wireless communication with the body motion sensors 41. Specifically, as illustrated in FIG. 18, the body motion sensors 41 are worn on wrists and elbows (a left wrist motion sensor 41e, a right wrist motion sensor 41f, and a right elbow motion sensor 41g) in addition to the body motion sensors 41 of the fourth embodiment. Incidentally, while only the right elbow motion sensor is illustrated in FIG. 18, it is assumed that the body motion sensor 41 is worn also on the left elbow.

The hub 70 is a router device which performs a communication process with each sensor 40 to collect detection results from the each sensor 40. This hub 70 can be detachably attached to clothing of a wearer or detachably attached as a belt or clothing. Alternatively, for example, the hub 70 can be provided as a member separately from clothing such as a pochette.

Such a hub 70 is provided with a data collection unit 71 and a data transfer unit 72 as illustrated in FIG. 19. The data collection unit 71 is a module for acquiring detection results of the body motion sensors 41 and the sole sensors 42, and provided with the function to perform wireless communication on the basis of a data communication protocol such as BTLE, ANT or the like. This data collection unit 71 recognizes a plurality of sensors 40 as a group, and acquires detection results of the sensors 40 within each group. Specifically, as illustrated in FIG. 19, the body motion sensors 41a to 41d worn on both knees and both feet and the foot sole sensors 42a and 42b are grouped as a first group 40, and the detection results therefrom are acquired by a first group collection unit 71a which communicates with these sensors. On the other hand, the body motion sensors 41e to 41g worn on both wrists and both elbows (including the body motion sensor worn on the left elbow) are grouped as a second group, and the detection results therefrom are acquired by a second group collection unit 71b which communicates with these sensors.

Meanwhile, in the case of the present modified example 1, it is assumed that each group collection unit 71a, 71b can associate up to a maximum of six sensors in one group. Because of this, since the group collection unit 71b of the modified example 1 currently associates the four body motion sensors 41 in one group, it is possible to additionally put further motion sensors on other parts. In the case where further body motion sensors 41 are worn on a body, these sensors are associated as a third group for which another group collection unit is provided in the group collection unit 71. Meanwhile, the number of connections in a group can be variously adjusted in accordance with the functions of the group collection units of the hub 70.

The data transfer unit 72 is a module for converting detection results acquired by the group collection unit 71 to data in an integrated format and transmitting the data to the information terminal device 100. In the case of the modified example 1, the detection results collected by the group collection units 71a and 71b are integrated in each group and transmitted to the information terminal device 100. The transmitted detection results additionally include identification information for identifying each sensor 40, wearing part identification information, time information and the like. Incidentally, the data transfer unit 72 performs wireless communication with the wireless communication unit 119b of the wearing type terminal 1 on the basis of a data communication protocol such as BTLE, ANT or the like.

The information terminal device 100 acquires the detection results which are acquired from the hub 70 and integrated for each group, and accumulates the detection results of the body motion sensors 41 and the sole sensors 42 in the memory 114 (body motion recording unit) as body motion data. The body motion data is then transmitted to the server device 5a through the docking type device 2, and the server device 5a calculates body motion reproduction data by the use of the acquired body motion data of each group, corrects the body motion reproduction data on the basis of the detection results of the foot sole sensors 42a and 42b, and analyzes the corrected body motion reproduction data. The groups are associated with each other, and the body motion calculation unit 52, the correction unit 54 and the analysis unit 55 performs the respective processes by the use of detection results acquired from the sensors 40 of all the groups.

The analysis results analyzed by the server device 5a are transmitted to the information terminal device 100, and displayed on the display unit 131 which is an output device of the wearing type terminal 1. Meanwhile, also in the case of the modified example 1, the other function modules of the information terminal device 100 are the same as in either of the first embodiment through the third embodiment, and therefore no redundant description or illustration in FIG. 19 is repeated. Incidentally, as illustrated in FIG. 18, a personal computer 9 is connected to the communication network 8, and the analysis results are transmitted to the personal computer 9 from the server device 5a and displayed on the display screen of the personal computer 9.

(Motion Capture Method)

Figure 20:
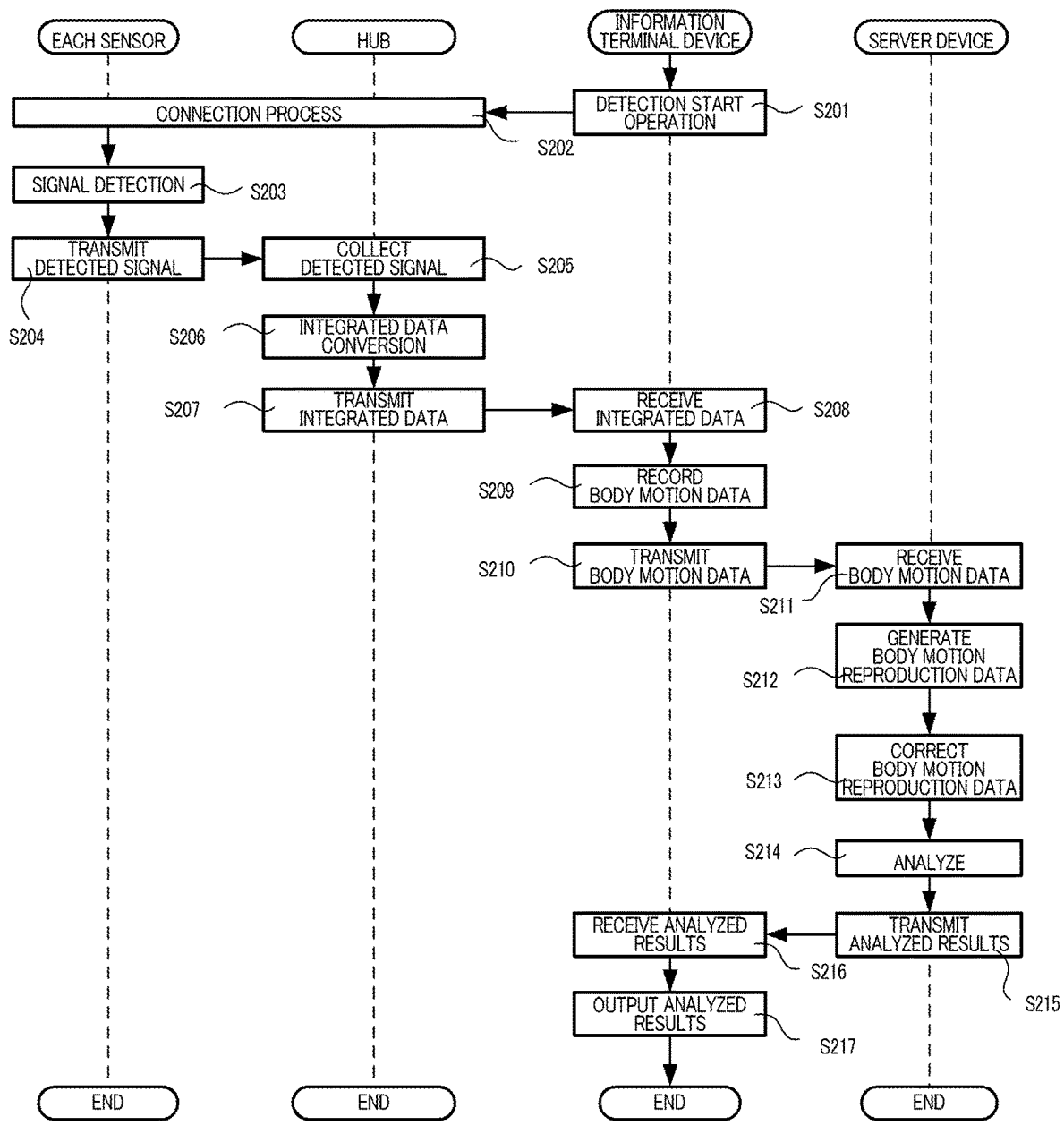
FIG. 20 is a sequence diagram for showing the motion capture method in accordance with the modified example 1.

The motion capture method in accordance with the present modified example 1 can be implemented by operating the motion capture system having the structure as described above. FIG. 20 is a sequence diagram for showing the motion capture method in accordance with the present modified example 1.

First, a wearer wears the body motion sensors 41 (41a to 41g) on both knees, both feet, both wrists and both elbows, and wears the sole sensors 42 on the shoe soles. The wearer also wears the information terminal device 100 and the hub 70 on predetermined parts.

Thereafter, the information terminal device 100 performs a detection start operation for the sensors 40 (S201). When acquiring a signal of this detection start operation, the control unit 170 of the wearing type terminal 1 controls the wearing type terminal 1 to transmit an operation signal to the hub 70, which then performs a connection process with each sensor 40 (S202). Incidentally, this operation of starting detection can be performed by directly operating the hub 70.

After performing the connection process between the hub 70 and each sensor 40, the each sensor 40 detects the motion of the wearer. Specifically, three-dimensional displacements and accelerations at each part of the wearer are detected by the body motion sensor 41 worn on this each part, and the pressures exerted on the sole are detected by the sole sensors 42 placed in the sole of the wearer.

Then, the detection results which are acquired are transmitted from the wireless communication unit of each sensor 40 to the data collection unit 71 of the hub 70 (S204). In this case, each sensor 40 belonging to the first group 40 performs a communication process with the first group collection unit 71a, and each sensor 40 belonging to the second group 40a performs a communication process with the second group collection unit 71b.

When acquiring the detection results of the body motion sensor 41 and the sole sensors (S2105), each of the group collection units 71a and 71b of the hub 70 converts the acquired detection result to data in an integrated format (S206), and transmits the integrated data to the information terminal device 100 (S207).

When the wireless communication unit 119b of the wearing type terminal 1 acquires the detection results in the integrated format for each group (S208), the memory 114 of the wearing type terminal 1 accumulates the detection results of the body motion sensors 41 and the sole sensors 42 as body motion data (S209). The wearing type terminal 1 then transmits the body motion data stored in the wearing type terminal 1 to the docking type device 2 through the dock side connection terminal 21 and the terminal side connection terminal 11. The wireless communication unit 206 of the docking type device 2 then transmits the acquired body motion data to the server device 5a (S210).

After the body motion data acquisition unit 53 of the server device 5a acquires body motion data (S211), the detection results of the body motion sensors 41 are transmitted to the body motion calculation unit 52, and the detection results of the sole sensors 42 are transmitted to the correction unit 54. The body motion calculation unit 52 calculates body motions of the wearer as body motion reproduction data on the basis of the detection results of the body motion sensors 41 accumulated in the memory 114 and the relative positional relationship among the body motion sensors 41 (S212), and transmits the body motion reproduction data to the correction unit 54. On the other hand, the correction unit 54 corrects the body motion reproduction data calculated by the body motion calculation unit 52 on the basis of the detection results of the sole sensors 42 (S213). The corrected body motion reproduction data is then transmitted to the analysis unit 55.

The analysis unit 55 analyzes the body motions of the wearer on the basis of the body motion reproduction data which is corrected by the correction unit 54 (S214). The analysis result data is transmitted to the information terminal device 100 through the communication interface 51 (S215). When receiving the analysis result data (S216), the docking type device 2 of the information terminal device 100 transmits this data to the wearing type terminal 1 through the dock side connection terminal 21 and the terminal side connection terminal 11. The control unit 170 of the wearing type terminal 1 has the display unit 131 display or output the acquired analysis results of the analysis unit 55 (S217).

(Effect/Action) In accordance with the present modified example as discussed above, since the body motion sensors 41 and the sole sensors 42 worn on a wearer are additionally provided, it is possible to calculate finer body motion reproduction data and analyze the body motions of the wearer. Particularly, in the case of the modified example 1, since detection results can collectively be transferred to another terminal by grouping a number of body motion sensors 41a to 41g, collecting data for each group, and converting the data in an integrated format, even in the case where a number of body motion sensors 41 and the sole sensors 42 are worn, it is possible to handle such many sensors and a large amount of data by making use of the data collection unit 71 and the data transfer unit 72 as the hub 70 and temporarily collecting and integrating data in the data transfer unit 72 even if the number of connections with communication devices and the data transfer amount are limited.

Modified Example 2

Figure 21:
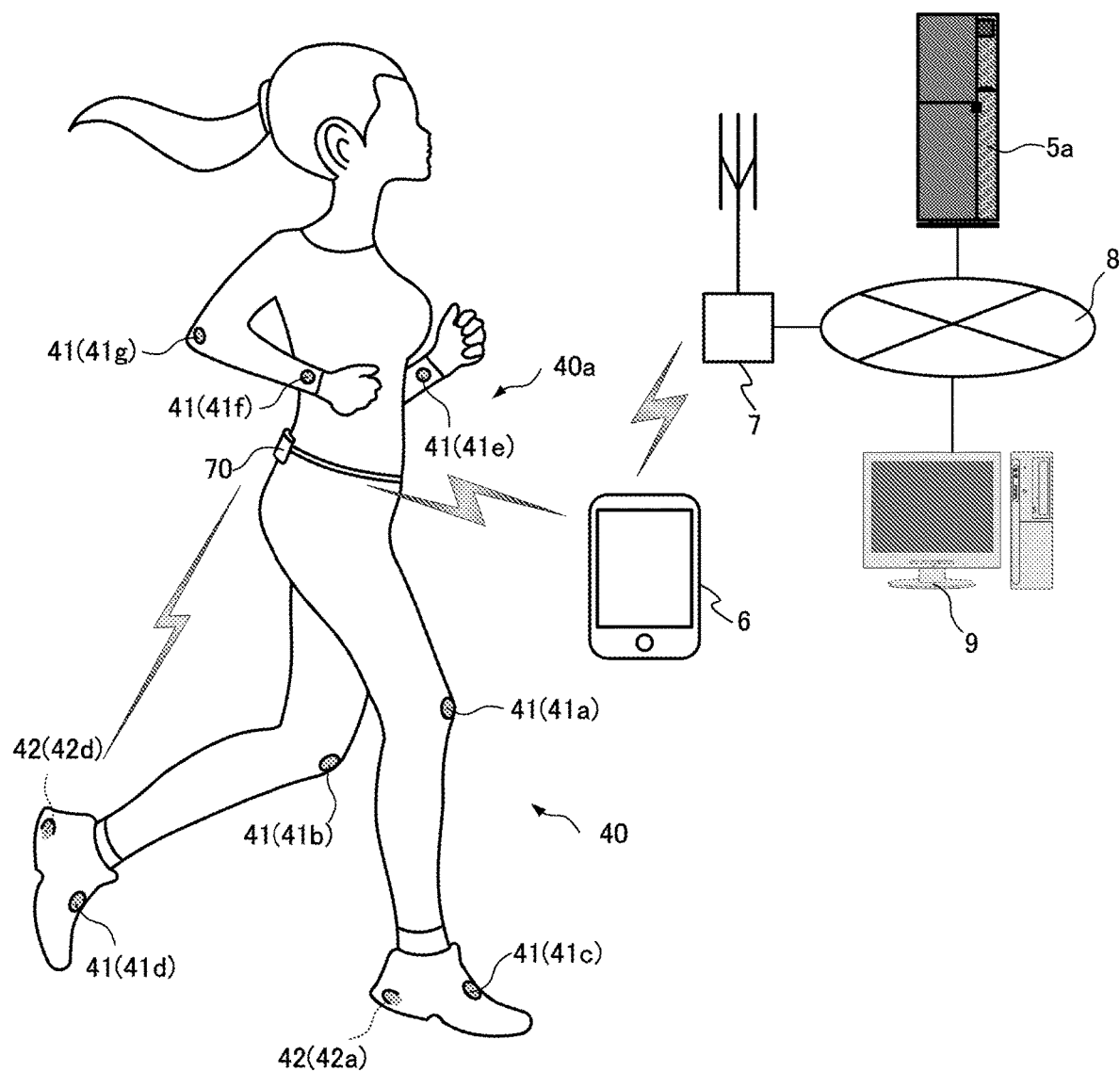
FIG. 21 is a view for schematically showing the configuration of an advice service in accordance with a modified example 2.
Figure 22:
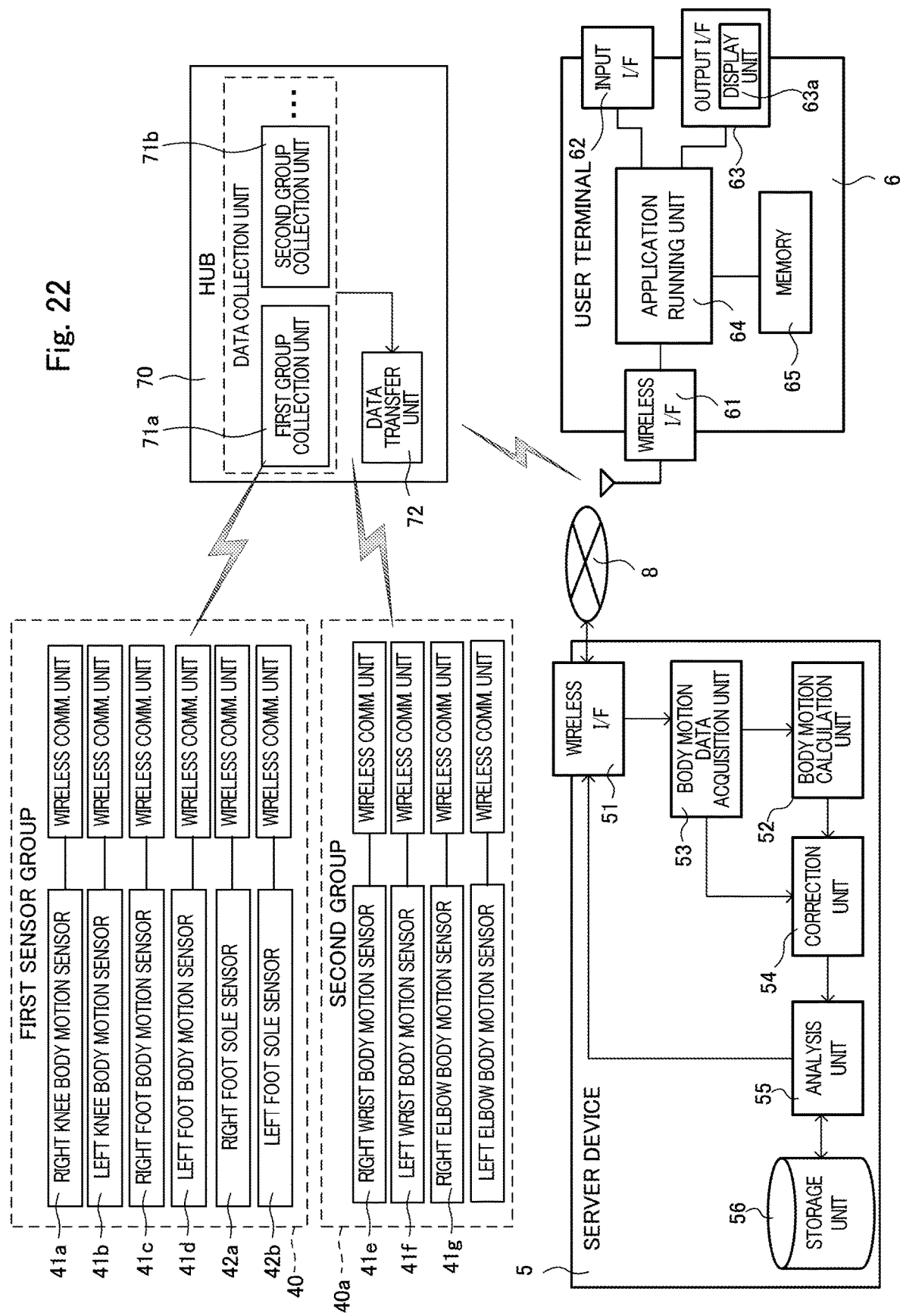
FIG. 22 is a block diagram for showing the internal structure of respective devices in accordance with the modified example 2.

Next is an explanation of a modified example of the above modified example 1. While the communication with the server device 5a is performed by the use of the information terminal device 100 worn on an arm of a wearer in the case of the modified example 1 as described above, the present modified example 2 will be explained in the case where the communication with the server device 5a is performed by the use of a user terminal 6 such as a smartphone carried by a wearer. FIG. 21 is a view for schematically showing the configuration of an advice service in accordance with the present modified example 2, and FIG. 22 is a block diagram for showing the internal structure of each device in accordance with the present modified example 2. Meanwhile, in the description of the following modified example, like reference numbers indicate functionally similar elements as the above embodiments and the modified examples unless otherwise specified, and therefore no redundant description is repeated.

The motion capture system of the modified example 2 is implemented, on the communication network 8, with the hub 70 worn on a wearer and a user terminal 6 performing wireless communication with the hub 70 worn on the wearer. The data collection unit 71 of the hub 70 groups a plurality of sensors 40 and acquires detection results from the sensors 40 in each group in the same manner as in the modified example 1 described above. On the other hand, the data transfer unit 72 of the hub 70 converts the detection result acquired by the data collection unit 71 in an integrated format, and transmits the converted data to the user terminal 6.

The user terminal 6 is a terminal carried by a user such as a cellular phone or a smartphone having an arithmetic processing capability by a CPU and a wireless communication capability to communicate with a relay point such as a usual base station and receive communication services such as telephone conversation, data communication and so forth while the user is moving. Furthermore, this user terminal 6 is implemented with a digital camera function, an application execution function, a GPS function and the like and serves also as a personal digital assistant (PDA). Also, also in the case of the modified example 2, the user terminal 6 is implemented with a short-range wireless communication function for performing tethering connection with the data transfer unit 72 of the hub 70 to communicate with the communication network 8 through the radio base station 7.

The internal structure of the user terminal 6 consists as illustrated in FIG. 22 of a wireless interface 61, a memory 65, an application running unit 64, an output interface 63, and an input interface 62.

The wireless interface 61 is provided with the function to perform wireless communication on the basis of a mobile communication protocol for telephone conversation, and wireless communication on the basis of a data communication protocol such as a wireless LAN. The wireless interface 61 is provided also with a wireless communication capability on the basis of a data communication protocol such as standard Bluetooth (registered trademark), BTLE, ANT or ANT+ to perform wireless short-range communication with the hub 70 and acquire detection results converted in a data format as body motion data. Also, the wireless interface 61 receives analysis result data from the server device 5a. Incidentally, the communication between the user terminal 6 and the hub 70 may automatically be performed on a real time base or at every predetermined time, or may be started in response to a user operation.

The input interface 62 is a device such as an operation button, a touch panel and the like for inputting user operations. On the other hand, the output interface 63 is a device such as a display, a speaker and the like for outputting images and sound. Particularly, this output interface 63 includes a display unit 13a such as a liquid crystal display. This display unit 13a serves as an output device for displaying or outputting analysis results of the analysis unit 55.

The memory 65 is a storage device for storing an OS (Operating System) and various application programs and other data, and identification information for identifying the hub 70 is accumulated in this memory 65 as information for performing wireless communication with the hub 70.

The application running unit 64 is a module for running a general OS, browser software and other applications, and usually implemented with a CPU and the like. This application running unit 64 transmits body motion data acquired from the data transfer unit 72 in an integrated format to the server device 5a, and receives analysis result data from the server device 5a.

(Motion Capture Method)

Figure 23:
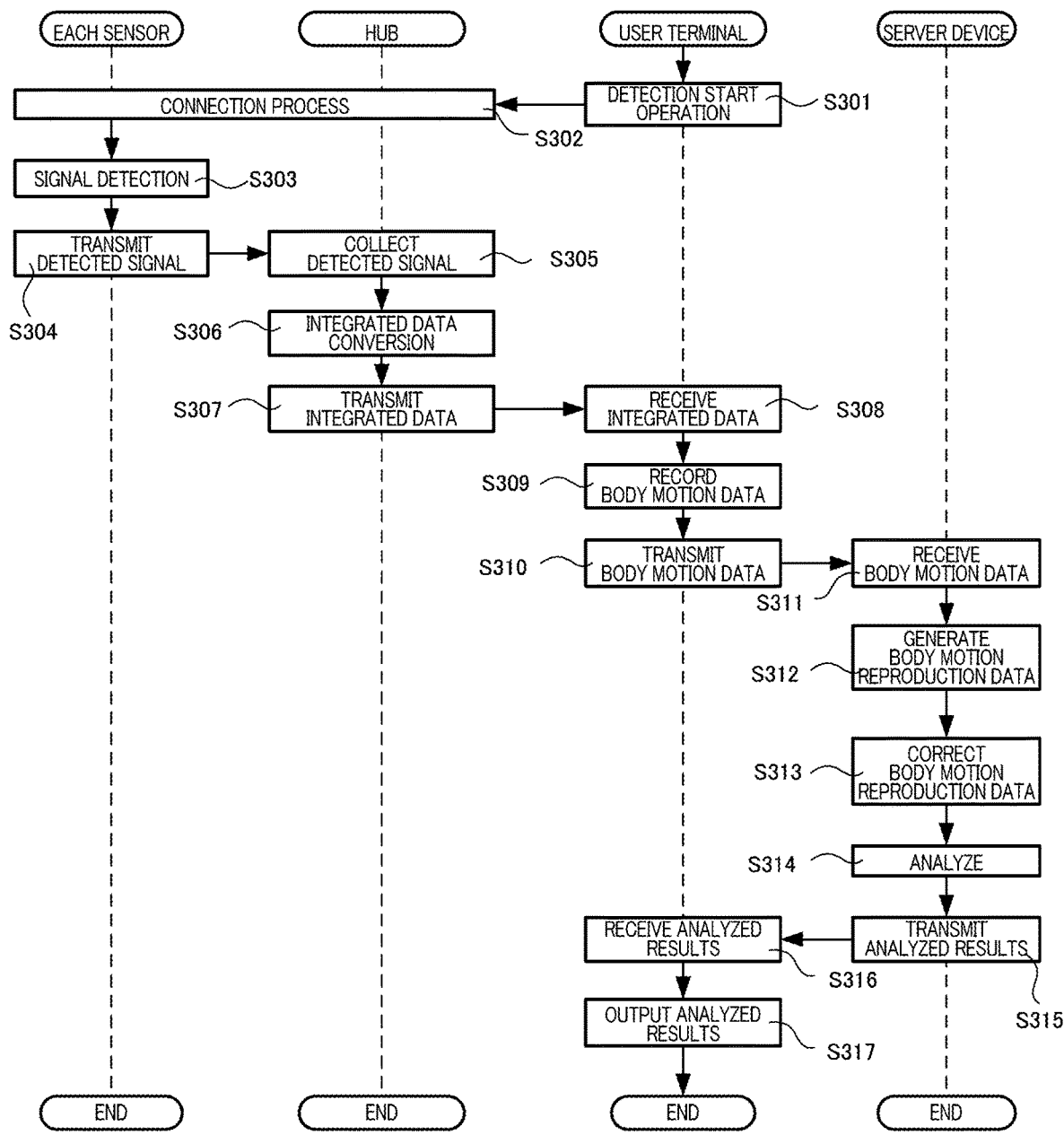
FIG. 23 is a sequence diagram for showing the motion capture method in accordance with the modified example 2.

The motion capture method in accordance with the present modified example 2 can be implemented by operating the motion capture system having the structure as described above. FIG. 23 is a sequence diagram for showing the motion capture method in accordance with the present modified example 2.

First, a wearer wears the body motion sensors 41 (41a to 41g) on both knees, both feet, both wrists and both elbows, and wears the sole sensors 42 and the hub 70. Next, the wearer operates the user terminal 6 in order that detection results from the sensors 40 is acquired by the hub 70 (S301). Incidentally, this operation of starting detection can be performed by directly operating the hub 70. Also, in the case of the modified example 2, the user terminal 6 can be worn in a pocket of closing, a waist pouch or the like, or can be put in a bag rather than wearing.

The hub 70 transmits an operation signal, and then performs a connection process with each sensor 40 (S302). After performing the connection process, each sensor 40 detect motions of the wearer (S303). Specifically, three-dimensional displacements or accelerations at each part of the wearer are detected by the body motion sensor 41 worn on this each part, and the pressures exerted on the sole are detected by the sole sensors 42 placed in the sole of the wearer.

Thereafter, the acquired detection results are transmitted from the wireless communication unit of each sensor 40 to the data collection unit 71 of the hub 70 (S304). In this case, each sensor 40 belonging to the first group 40 performs a communication process with the first group collection unit 71a, and each sensor 40 belonging to the second group 40a performs a communication process with the second group collection unit 71b.

When acquiring the detection results of the body motion sensor 41 and the sole sensors 42 (S305), each of the group collection units 71a and 71b of the hub 70 converts the acquired detection result to data in an integrated format (S306), and transmits the integrated data to the user terminal 6 (S307).

When the wireless interface 61 of the user terminal 6 acquires the detection results in the integrated format for each group (S308), the memory 65 of the user terminal 6 serving as the body motion recording unit accumulates the detection results of the body motion sensors 41 and the sole sensors 42 as body motion data (S309). The user terminal 6 then transmits the recorded body motion data to the server device 5a (S310).

After the body motion data acquisition unit 53 of the server device 5a acquires body motion data (S311), the detection results of the body motion sensors 41 are transmitted to the body motion calculation unit 52, and the detection results of the sole sensors 42 are transmitted to the correction unit 54. The body motion calculation unit 52 calculates body motions of the wearer as body motion reproduction data on the basis of the detection results of the body motion sensors 41 accumulated in the memory 65 and the relative positional relationship among the body motion sensors 41 (S312), and transmits the body motion reproduction data to the correction unit 54. On the other hand, the correction unit 54 corrects the body motion reproduction data calculated by the body motion calculation unit 52 on the basis of the detection results of the sole sensors 42 (S313). The corrected body motion reproduction data is then transmitted to the analysis unit 55.

The analysis unit 55 analyzes the body motions of the wearer on the basis of the body motion reproduction data which is corrected by the correction unit 54 (S314). The analysis result data is transmitted to the user terminal 6 through the communication interface 51 (S315). When receiving the analysis result data (S316), the application running unit 64 displays or outputs the acquired analysis results of the analysis unit 55 on the display panel 63a (S317).

Incidentally, while the separate devices such as the hub 70 and the user terminal 6 are used to collect the detection results acquired from each sensor 40 and then record the detection results in the memory 65 of the user terminal 6 in the case of the modified example 2, the present invention is not limited thereto. For example, the function of the hub 70 can be implemented within an information mobile terminal which is used as a device within which the hub 70 and the user terminal 6 are integrated. Furthermore, the calculation of body motion reproduction data, the correction process and the analysis process, which are performed by the server device 5*a* in the above example, can be implemented within the user terminal 6 in a stand-alone configuration.

(Effect/Action)

Since the user terminal 6 carried by a wearer is used to acquire detection results from the hub 70 and accumulate the detection results as body motion data in accordance with the modified example 2 as described above, it is possible to use a smartphone which is carried by the user as a motion capture system which detects body motions of the wearer and reduce the initial adoption expenses.

Modification Examples

Incidentally, the embodiments 1 through 4 and the modified examples as described above are examples of the present invention. Because of this, the present invention is not limited to the above embodiments and the modified examples, and various modifications and combinations of the respective components are possible in accordance with the design and so forth without departing from the technical spirit of the invention.

For example, it is possible to connect the wearing type terminal 1 of the first embodiment with the docking type device 2*a* of the second embodiment through the dock side connection terminal 21, and connect the wearing type terminal 1*a* of the second embodiment with the docking type device 2 of the first embodiment through the dock side connection terminal 21. Also, for example, it can be arbitrarily determined which functions are assigned to which of the wearing type terminals 1 and 1*a* and the docking type devices 2 and 2*a* explained as the first embodiment and the second embodiment. For example, the wireless communication unit 206*a* based on Bluetooth (registered trademark) or the like can be implemented within the docking type device 2 of the first embodiment, and the vibration motor 204 can be implemented within the wearing type terminal 1. Alternatively, the wearing type terminal 1 or the docking type device 2 can be implemented with a browser function to receive Web data directly through the communication network and display the data on the display units 131 and 133.

Furthermore, for example, the docking type devices 2 and 2*a* can be implemented with a camera capable of imaging and a pulse meter capable of measuring the pulse of a user. In this case, a camera is implemented in a position where its lense is oriented outward when the docking type device 2 or 2*a* is connected to the wearing type terminal 1 and worn on an arm of a user. Also, a pulse meter is implemented in the bottom of the docking type device 2 which comes in contact with user's skin. It is therefore possible to display images and videos captured by the camera by connecting the wearing type terminal 1 or 1*a* with the docking type device 2 through the connection terminals 11 and 21, and display the result measured by the pulse meter on the display units 131 and 133.

Also, it is possible to implement a system for preventing theft of the terminal device, and theft of a bicycle, a motorbike, an automobile and the like mounted on the terminal device by the use of the communication capability of the wearing type terminal 1 and the docking type device 2 as described in the above embodiments, the sensors provided on the terminal device, and the sensor or the like connected to the terminal device through wireless communication. In this case, theft can be detected by mounting the wearing type terminal 1, the docking type device 2 or other sensors on a monitoring object such as a bicycle, an automobile or the like, and remotely monitoring a detecting signal from the sensors through the communication interface of the wearing type terminal 1 or the docking type device 2 to detect vibration or motion caused during theft. Also, it is possible to prevent theft beforehand by outputting a buzzing sound, an alarm, a warning sound, illumination, a rumbling sound such as vibration or the like in accordance with detected values from the sensors provided on the wearing type terminal 1 and the docking type device 2 which are mounted.

Furthermore, while the body motion reproduction data is analyzed by the server device provided on the communication network in accordance with the embodiment and the modified examples, the present invention is not limited thereto. For example, the information terminal device 100, the user terminal 6, the hub 70 or the like can perform the execution and processes. In this case, the information terminal device 100, the user terminal 6 or the hub 70 is provided with the function modules having the same functions as the body motion data acquisition unit 53, the body motion calculation unit 52, the correction unit 54 and the analysis unit 55, and the data stored in the storage unit 56 can be accumulated in a memory or the like.

Fifth Embodiment

Next, a fifth embodiment of the present invention will be explained. The present embodiment is characterized in that a motion capture system for detecting the body motions of a wearer is provided by the use of various sensors worn on the wearer and the information terminal device 100*b* described above as the first or second embodiments. Particularly, the present embodiment provides a system which makes it possible to perform measurement and coaching for multiple-stage competition such as triathlon involving cycling and running by the use of a single information terminal device 100*b*.

(Structure of Each Device)

Figure 24A:
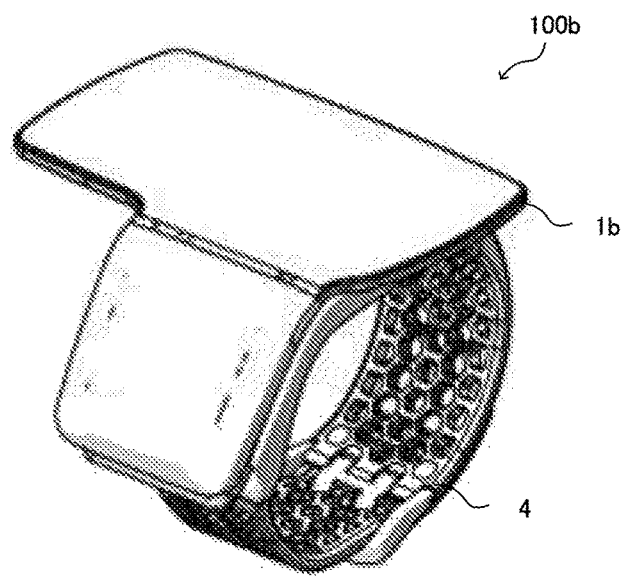
FIGS. 24A and 24B are explanatory views for showing a motion capture system in accordance with a fifth embodiment.
Figure 24B:
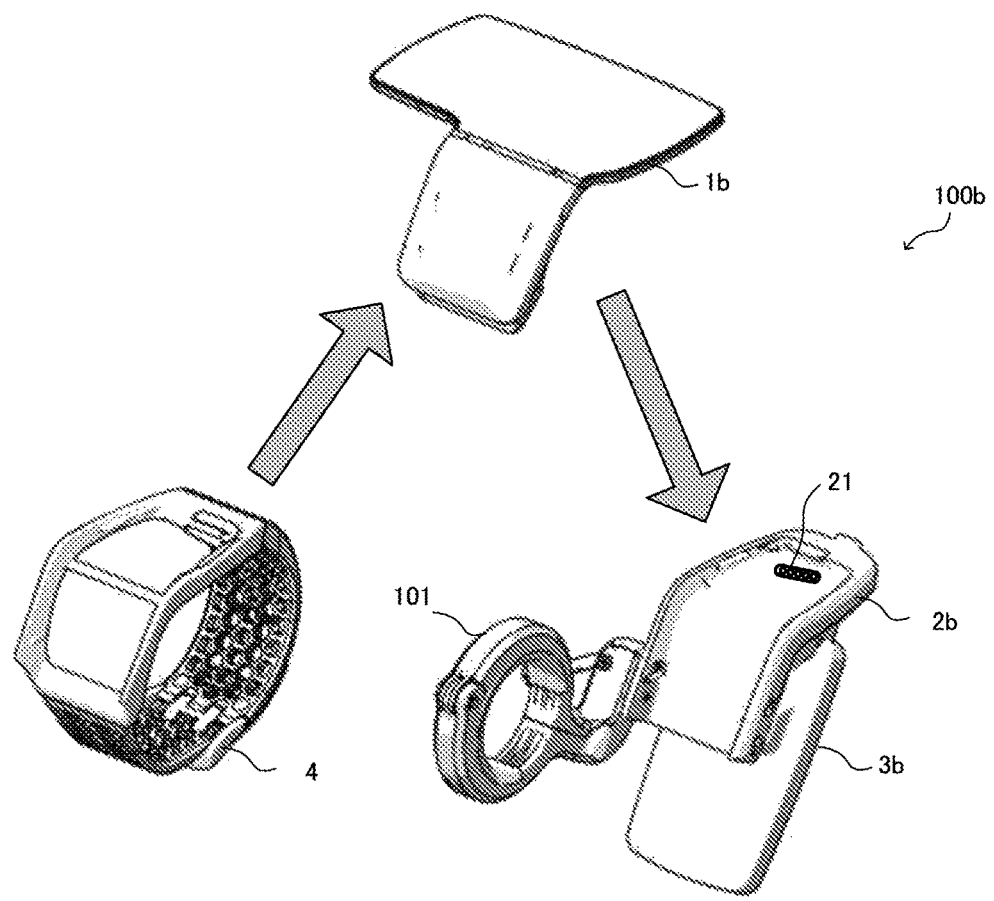
Figure 26A:
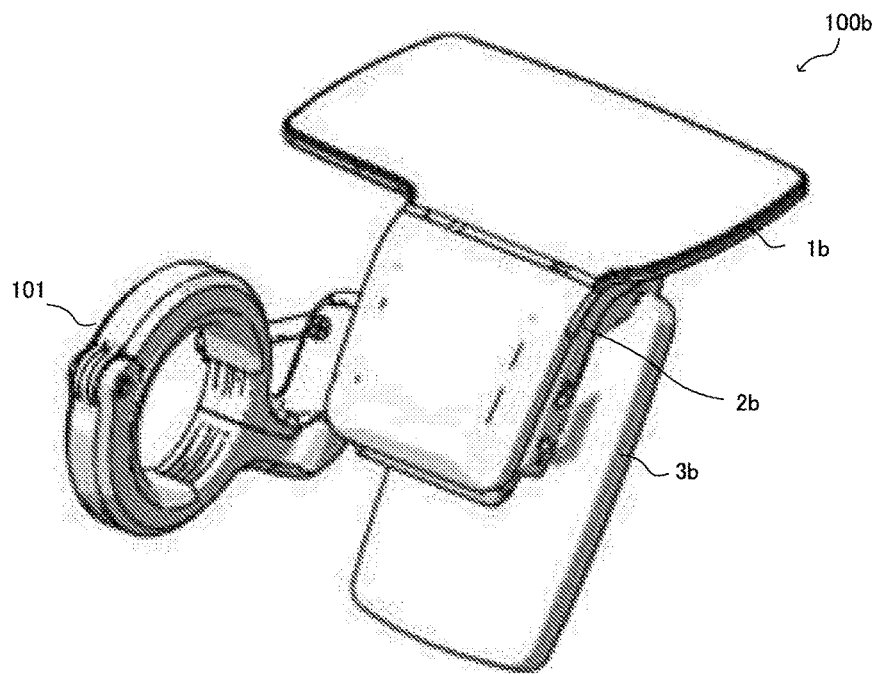
FIG. 26A is a perspective view for showing the information terminal device mounted on a mount device in accordance with the fifth embodiment.
Figure 26B:
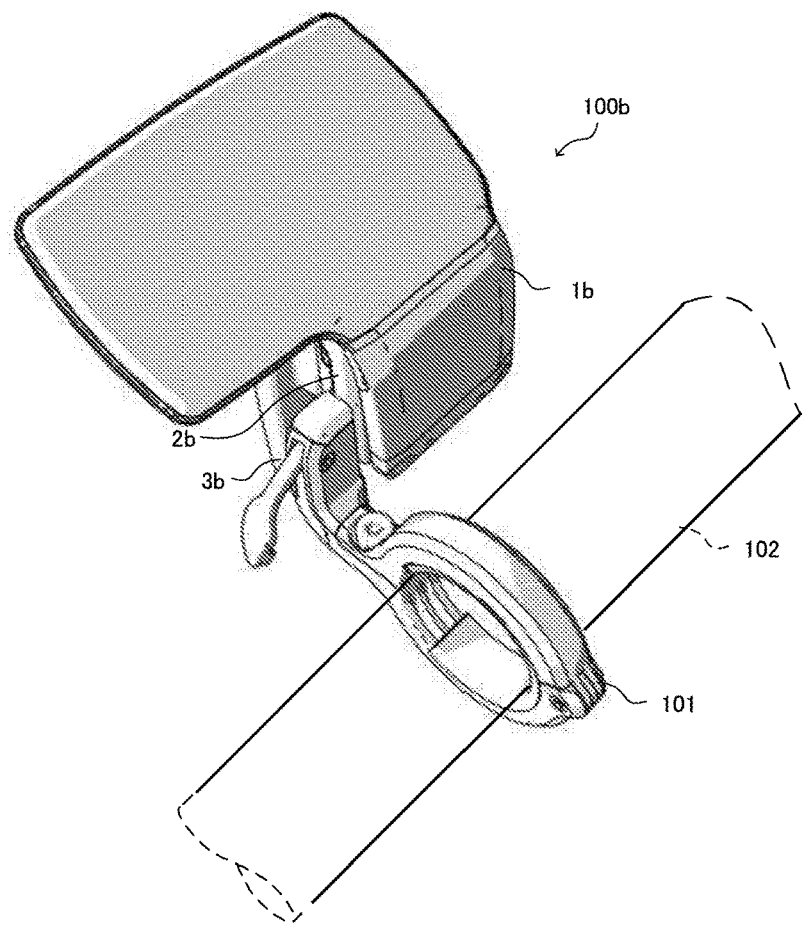
FIG. 26B is an explanatory view for showing the usage thereof.

The information terminal device 100*b* in accordance with the present embodiment is a wrist watch type wearable terminal which can be worn by a user with a belt member 4, as illustrated in FIGS. 24A and 24B, and consists of a wearing type terminal 1*b* which can be worn on the arm of the user, a docking type device 2*b* and a power supply device 3*b* which is detachably connected with the docking type device 2*b*. Incidentally, the wearing type terminal 1*b*, the docking type device 2*b* and the belt member 4 are also detachably attached to each other and can be separated and joined if necessary. Also, there are many types of the wearing type terminal 1*b* and docking type device 2*b* which have different additional functions and different designs in accordance with using purposes respectively, and can be arbitrarily selected and freely combined for the purposes. For example, as illustrated in FIG. 24B and FIG. 26, the docking type device 2*b* to be joined to the wearing type terminal 1*b* can be connected to a mount device 101 for mounting the docking type device 2b on the handlebar of a bicycle, and the power supply device 3b which is a battery as an extension.

Specifically speaking, in the case of the present embodiment, the information terminal device 100b can be worn on an arm of a user with the belt member 4 as the wearing type terminal in the form of a wristband, and mounted on the handlebar 102 of a bicycle with a clamp of the mount device 101, and it is possible to continuously utilize a single (a type of) information terminal device for both cycling and running, and continuously and seamlessly utilize the sensors worn on a human body for both cycling and running without removing the sensors.

Figure 25A:
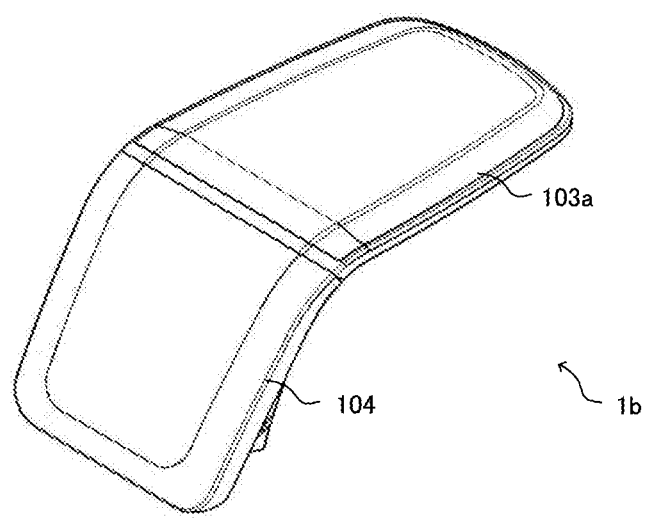
FIG. 25A is a perspective view for showing the overall configuration of an information terminal device (implemented with a small display) in accordance with the fifth embodiment.
Figure 25B:
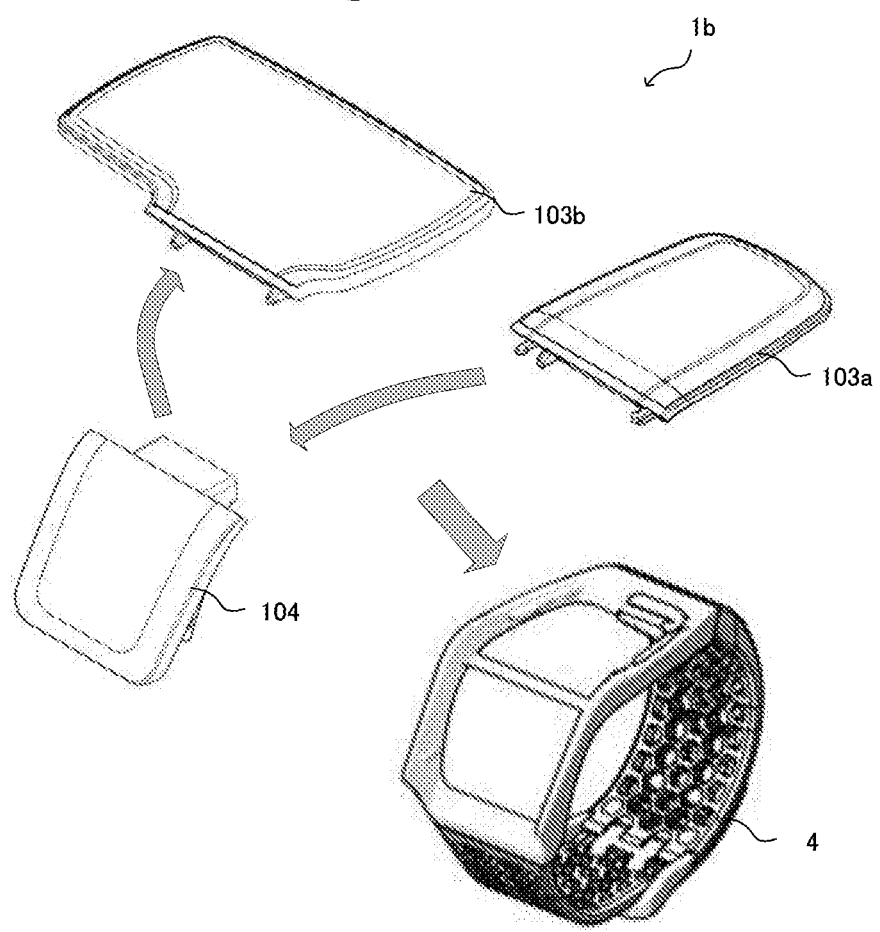
FIG. 25B is an explanatory view for showing the usage thereof.

Furthermore, in the case of the wearing type terminal 1b itself as illustrated in FIG. 25, a display unit 103 can be separated from an operation unit 104 provided with an operation button, a touch panel and the like so that the display unit can be switched between a larger one (large display 103b) and a smaller one (small display 103a) in accordance with the event of a competition and the measurement purpose. By this configuration, it is possible to appropriately give priority to either a sufficient information display capacity corresponding to the area of the display or power saving performance by miniaturizing the device size. Incidentally, as illustrated in FIG. 25B, in either case where the large display 103b or the small display 103a is selected and connected to the operation unit 104, the wearing type terminal 1b can be mounted on the same belt member 4.

Each of the large display 103b and the small display 103a is provided with a liquid crystal display on top thereof, an engagement structure and an electrically connecting connector for connecting the display to the operation unit 104 with a side surface. The bottom portions of the large display 103b, the small display 103a and the operation unit 104 are provided with an engagement structure for mounting on the belt member 4. The belt member 4 is a member for putting the wearing type terminal 1b on an arm, and can be one of a variety of belt members in accordance with the use, i.e., a metal belt, a rubber belt, a leather belt and a nylon belt.

The large display 103b or the small display 103a is connected to the operation unit 104 in an inclined fashion. After connection, the wearing type terminal 1b is curved in a dog leg form as seen from the side to conform to the roundness of an arm of a wearer. The large display 103b or the small display 103a is a display on which a message, an input string and the like are displayed to a user, and provided with a touch panel integrally formed on the upper surface side thereof. This touch panel detects a position touched of the display, for example, in units of dots forming the display by a detection system of a pressure-sensitive type, an optical type, an electrostatic type, an electromagnetic induction type or the like type to output a signal indicative of the detected position (hereinafter referred to as "touch position"). The touch position is represented by an XY coordinate system which is set as a coordinate system of the detection plane of the touch panel. A user can perform various input operations by a touch operation on the display with a supplied touch pen PN, a finger or the like.

This touch panel, which is waterproofing, can detect a touched position of the display and outputs the detection signal as a touch position even on the surface of the water by a special electrostatic capacitance detection system. The touch position is represented by an XY coordinate system which is set as a coordinate system of the detection plane of the touch panel. A user can perform various input operations by a touch operation on the display even in an environment where water exists. Incidentally, the watch body can be operated also with mechanical buttons which are provided on the watch body.

Meanwhile, the small display 103a has an approximately trapezoidal shape to fit into the width of the belt member 4. On the other hand, the large display 103b has a shape which is extending in the side direction from the width of the belt member 4. The extending portion is protruding in the arm direction toward the opposite side to the hand of the wearer.

The operation unit 104 is provided with a GPS antenna and a wireless antenna which are located in an external case. The GPS antenna is an antenna (first antenna) for wireless communication made of a conductive material such as a stainless steel for acquiring satellite information such as satellite orbit information, GPS time information, positional information and the like which are included in a navigation message of a satellite signal in a 1.5 GHz band extracted through a SAW filter which is not shown in the figure. Also, the wireless antenna incorporated in the operation unit 104 is an antenna for BTLE (Bluetooth (registered trademark) Low Energy), which are very low power consumption short range communication standards, and used for communicating with various sensors and other small devices worn on a body. This wireless antenna is made also of a conductive material such as a stainless steel.

Also, in the case of the present embodiment, the operation unit 104 is equipped with operation buttons for manually manipulating on the side surface thereof, and a touch panel, an LED for indicating a state or the like on the top surface of the operation unit 104. Furthermore, in the case of the present embodiment, the operation unit 104 is waterproofing, and has the function to acquire and display speed information and positional information by processing radio waves (wireless signals) from a GPS satellite. Still further, an acceleration sensor or the like can be incorporated in the operation unit 104 to provide the functionality as an activity meter on the basis of the measurement of acceleration of body motions.

On the other hand, the docking type device 2b is an information terminal device which can be detachably connected to the wearing type terminal 1b, and is a case body having a curved indent section which conforms to the profile of the wearing type terminal 1b. In the case of the present embodiment, the docking type device 2b is made of a synthetic resin such as a cured plastic and provided with an information terminal device such as a CPU inside thereof. Then, in the case of the present embodiment, this docking type device 2b is formed with a dock side connection terminal (first connection terminal) 21 on the upper surface thereof, and detachably joined with the bottom portion of the external case of the wearing type terminal 1b through the dock side connection terminal 21. Specifically, the bottom portion of the wearing type terminal 1b is provided with a terminal side connection terminal in a position corresponding to the dock side connection terminal 21 so that the docking type device 2b and the wearing type terminal 1b can electrically be connected to each other by connecting the dock side connection terminal 21 with the terminal side connection terminal. The wearing type terminal 1b and the docking type device 2b are configured to supply electric power from the docking type device 2b to the wearing type terminal 1b through the dock side connection terminal 21, and transmit and receive data therebetween for displaying the data on the large display 103b or the small display 103a.

Also, this docking type device 2b is equipped with a battery which is detachable, has an RFID communication capability for contactlessly reading and writing data through wireless radio waves, and is capable of wirelessly communicating with an external reader writer with a wireless communication antenna provided on the docking type device 2b. This wireless antenna is an antenna for contactless wireless communication (NFC (Near Field Communication)) to transmit and receive data by the use of weak radio waves radiated from the external reader writer. Furthermore, in the case of the present embodiment, the docking type device 2b is provided with a USB terminal to be electrically connected to an external device such as a personal computer. The USB terminal is provided on the outside of the docking type device 2b, can be connected to an external device through a USB cable, and installed in a connector which is located at one side of the docking type device 2b for protecting the USB terminal 33.

The power supply device 3b is a device detachably connected with the bottom portion of the docking type device 2b for supplying and charging electric power to the wearing type terminal 1b and the docking type device 2b. In the case of the present embodiment, the power supply device 3b may be an indoor installation type device to be installed in user's home or the like, or a portable device to be installed in an automobile or a bicycle. In the case where the power supply device 3 is an indoor installation type device, electric power is supplied through a wall outlet and a power cable. On the other hand, in the case where the power supply device 3 is a portable device, a battery may be provided which can accumulate power supply through an external AC adapter.

Meanwhile, this battery may incorporate a transformer, a rectifier, a regulating circuit for converting an alternating current to a direct current. Incidentally, the configuration of the power supply device 3b can be modified in accordance to the use. For example, in the case where the power supply device 3 is installed on a table or the like, an installation base is provided on the bottom surface thereof. Also, in the case where the power supply device 3b is installed on a bicycle, an attachment member is attached for housing or fixing the power supply device 3 to a handlebar.

(Procedure of Motion Capture Method)

Figure 27A:
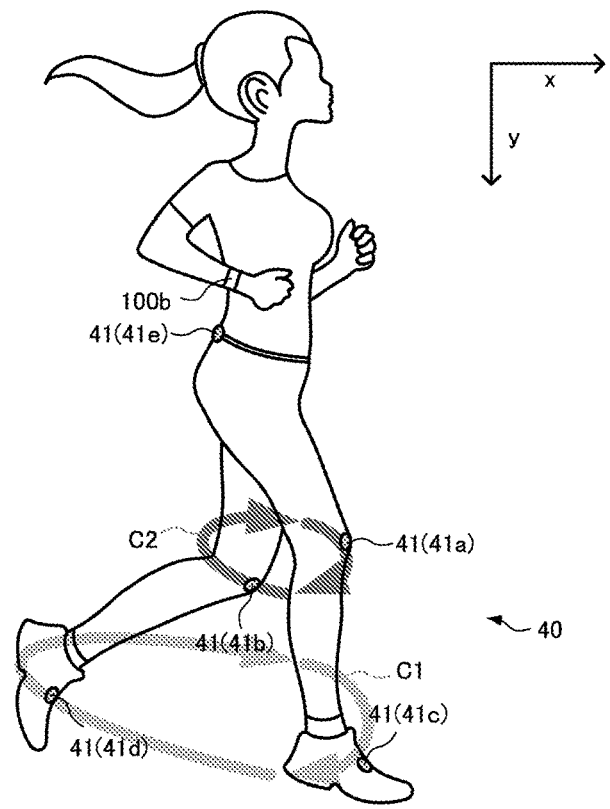
FIGS. 27A and 27B are explanatory views for showing a motion capture method in accordance with the fifth embodiment.
Figure 27B:
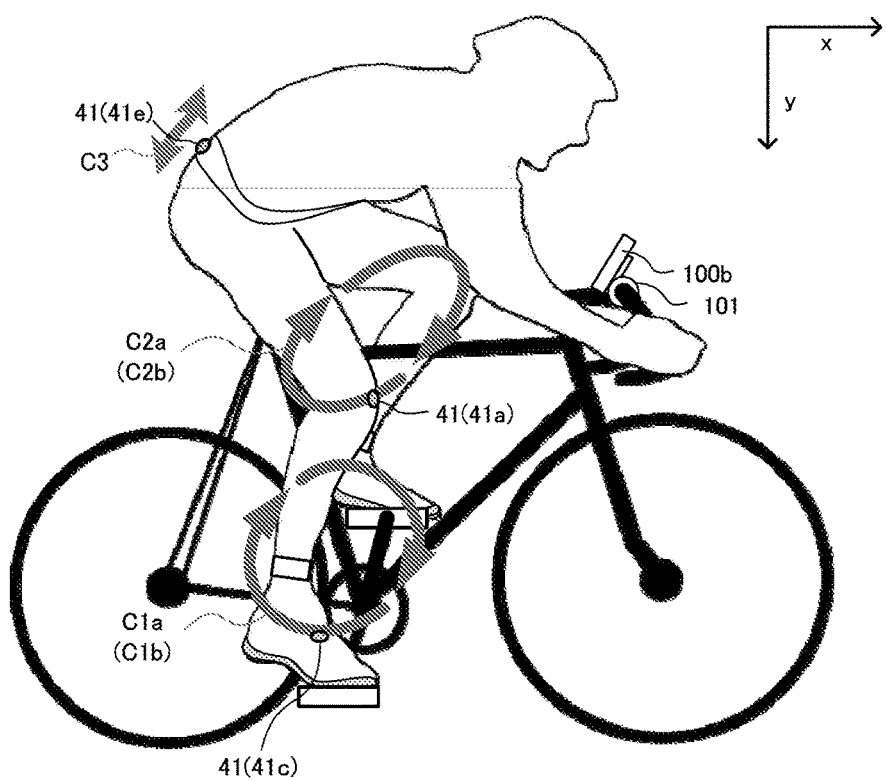
Figure 28:
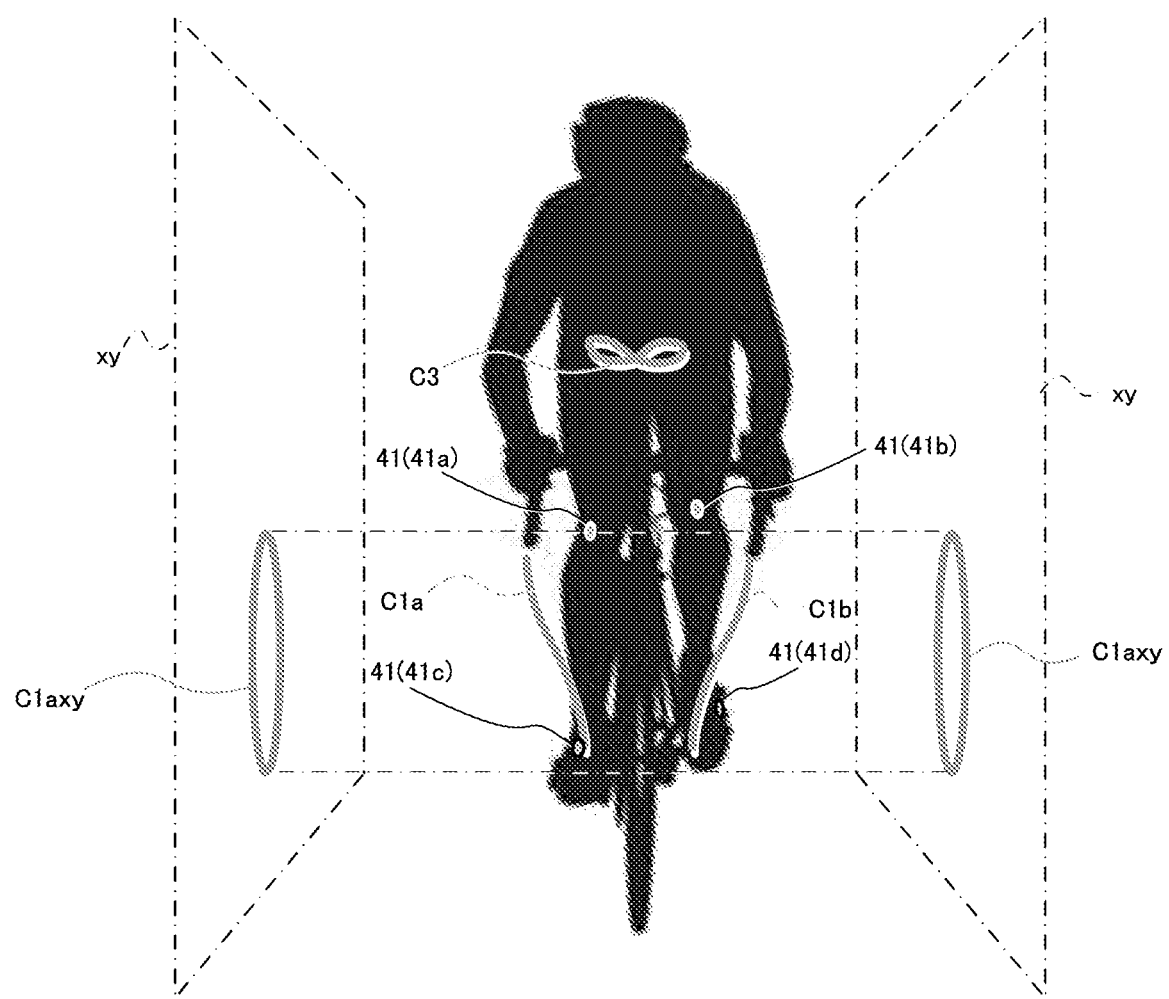
FIG. 28 is an explanatory view for showing the process of extracting cyclic patterns in the motion capture system during a bicycle race in accordance with the fifth embodiment.
Figure 29:
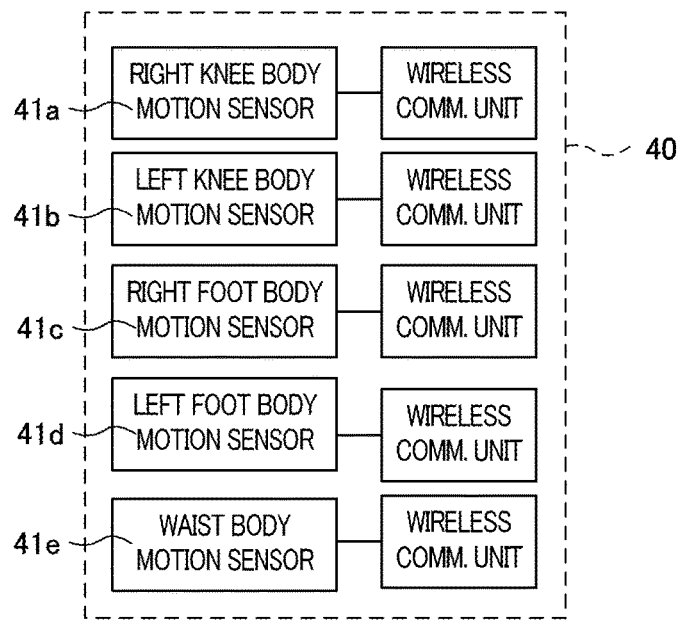
FIG. 29 is a block diagram for showing the internal structure of the respective devices in accordance with the fifth embodiment.
Figure 29:
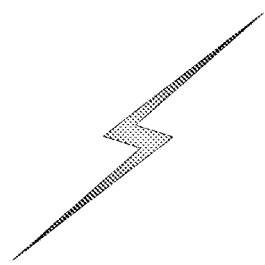
Figure 29:
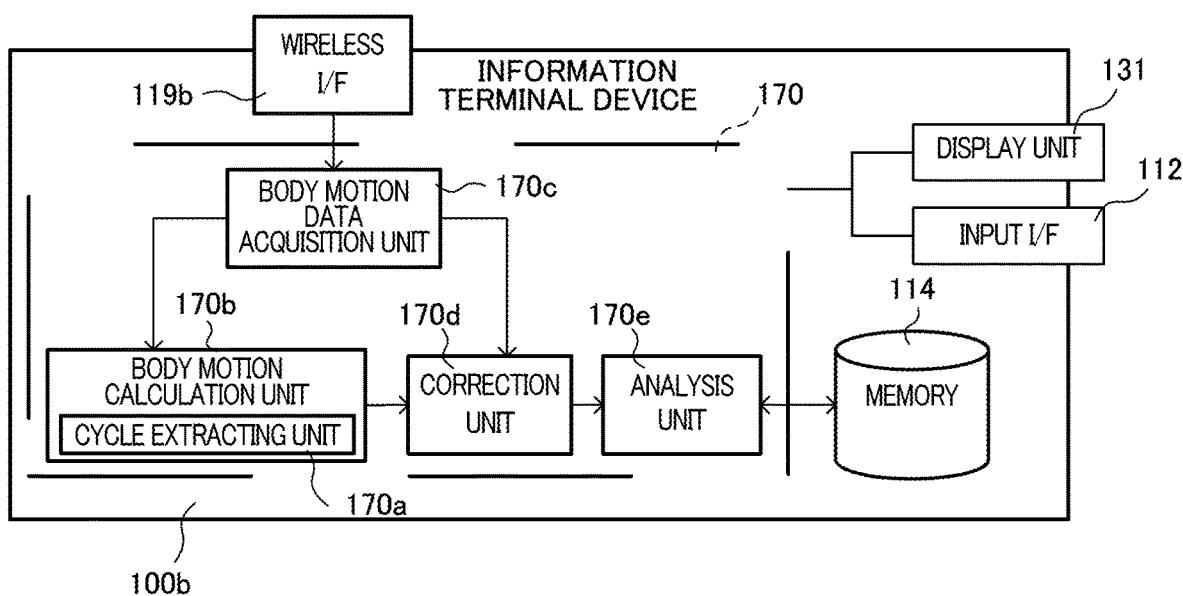

FIG. 27 and FIG. 28 are explanatory views for schematically showing a motion capture system by the use of the information terminal device 100b in accordance with the present embodiment. On the other hand, FIG. 29 is a block diagram for showing the internal structure of the respective devices in accordance with the present embodiment.

As illustrated in FIG. 27 and FIG. 28, the motion capture system in accordance with the present embodiment consists of the information terminal device 100b worn on a wearer, and various types of sensors 40 worn on each part of the wearer and connected to the information terminal device 100b through wireless connection. Meanwhile, in the case of the present embodiment, a system can basically be implemented within an area where short range wireless communication is available between the information terminal device 100b and the various types of sensors 40. The system is not connected to a server or the like on the communication network during actual measurement, and can be operated offline in a so-called stand-alone configuration.

The various types of sensors 40 are a group of sensors which are detachably worn on a wearer and, in the case of the present embodiment, includes a plurality of sensors such as the body motion sensors 41. Incidentally, this example does not use the sole sensors 42 as in the above embodiments. However, the sole sensors 42 can be used if necessary.

The body motion sensors 41a to 41e are a group of sensors which are worn on respective parts of the body of the wearer to detect the three-dimensional displacement, angular speed and acceleration of each part. In the case of the present embodiment, the body motion sensors 41 are worn on predetermined joints of the wearer. Specifically, the body motion sensors 41 include a right knee body motion sensor 41a worn on the right knee of the wearer, a left knee body motion sensor 41b worn on the left knee of the wearer, a right foot body motion sensor 41c worn on the instep of the right foot of the wearer, a left foot body motion sensor 41d worn on the instep of the left foot of the wearer, and a waist body motion sensor 41e worn on the waist of the wearer. Each motion sensor 41 incorporates a three-axis acceleration meter for measuring the acceleration of an object, a three-axis gyroscope for measuring the angular speed of the object, a three-axis magnetic sensor for measuring the magnitude and direction of a magnetic field, so that motions about nine axes can be detected.

Each motion sensor 41 can be detachably worn on the clothing of a wearer with a clip or the like, or detachably attached as a belt or clothing. By this configuration, a wearer can attach each sensor to a belt or clothing for measurement in the feelings of daily life as if attaching a small article to a belt or clothing, or wearing a belt or clothing, so that it is possible to perform continuous measurement without putting burdens on the wearer.

Each of the sensors 40 (the body motion sensors 41a to 41e) is provided with a wireless communication unit as illustrated in FIG. 29. This wireless communication unit incorporates an antenna and can perform a communication process with the information terminal device 100b by the function to perform short-range wireless communication on the basis of a data communication protocol such as BTLE (Bluetooth (registered trademark) Low Energy, Bluetooth (registered trademark) 4.0). Incidentally, while the wireless communication unit of each sensor 40 uses BTLE as a low power consumption communication protocol in the case of the present embodiment, ANT, ANT+ or the like protocol can be employed instead. Alternatively, standard Bluetooth (registered trademark) can be employed instead.

The information terminal device 100b can be used as a wearing type terminal, and has, in addition to the functions of the above embodiments, the function to collect detection results obtained by each sensor 40, and obtains the detection results by a communication process between each sensor 40 and the wireless communication unit 119b. The memory 114 of the information terminal device 100b serves as a body motion recording unit which can accumulate the detection results of the body motion sensors 41 as body motion data. Incidentally, the detection results as transmitted from each sensor 40 include sensor identification information which is added for identifying this each sensor 40 and accumulated in the memory 114 of the information terminal device 100 so that when acquiring the detection result through the wireless communication unit 119b, the control unit 170 can determine which sensor 40 outputs that detection result. Also, this identification information of each sensor includes wearing part identification information for identifying the part on which this each sensor is worn, and body motion reproduction data can be calculated on the basis of this wearing part identification information. Furthermore, the body motion data includes time information when the detection result is acquired from each sensor 40.

In addition, the information terminal device 100 has the function to transmit the acquired body motion data to the server device 5a of the communication network 8 as described in the above embodiments. Specifically, the body motion data recorded by the wearing type terminal 1 is transmitted to the docking type device 2b through the dock side connection terminal 21 and the terminal side connection terminal 11. The wireless communication unit 206 of the docking type device 2b then transmits the acquired body motion data to the server device 5a.

The communication interface 119b is a module for controlling transmission and reception of various information through the communication network 8 and controlling wireless short-range communication such as wifi or Bluetooth (registered trademark) to communicate with the sensors and the docking type device 2 of the information terminal device 100b by the use of one of various protocols and perform data transmission and reception with the server device 5a and the like through 3G communication. In the case of the present embodiment, the communication interface 119b is used to acquire body motion data from the docking type device 2, and transmit the analysis result obtained by the analysis unit 55 to the server device 5a or the like.

Furthermore, the display unit 131 of the information terminal device 100b serves as an output device which displays or outputs an analysis result of body motion reproduction data by acquiring the analysis result from the server device 5a and displaying the analysis result under the control of the control unit 170. Meanwhile, in the case of the present embodiment, the other function modules of the information terminal device 100b are the same as in either of the first embodiment through the fourth embodiment, and therefore no redundant description or illustration in FIG. 26 is repeated.

Furthermore, the information terminal device 100b of the present embodiment has the function to analyze the body motions of a wearer on the basis of body motion data acquired from the sensors, and generate the body motion reproduction data. Specifically, as illustrated in FIG. 29, the information terminal device 100b is provided with the control unit 170 which is an arithmetic processing unit such as a CPU for performing arithmetic operations required for controlling the respective elements. Incidentally, the respective functions of the information terminal device 100b are virtually implemented within the control unit 170 by running a predetermined program with this control unit 170. Specifically, the control unit 170 virtually implements a body motion data acquisition unit 170c, a body motion calculation unit 170b, a cycle extracting unit 170a, a correction unit 170d and an analysis unit 170e.

The body motion data acquisition unit 170c is a module for acquiring body motion data from the sensors 40 through the wireless interface 119b. In the case of the present embodiment, the body motion data acquisition unit 53 acquires the detection results of the sensors 41a to 41e as body motion data by performing wireless communication with the sensors 41a to 41e. This body motion data is temporarily accumulated in the memory 114, and then the detection results of the body motion sensors 41 are transmitted to the body motion calculation unit 52. Also, the detection results of the waist body motion sensor 41e are transmitted to the correction unit 170d.

The body motion calculation unit 170b is a module for calculating body motions of a wearer as body motion reproduction data on the basis of the detection results of the body motion sensors 41a to 41e accumulated in the memory 114 (body motion recording unit) and the relative positional relationship among the body motion sensors 41a to 41e. In this case, the detection results of the body motion sensors 41 are values which are measured with a so-called nine-axis sensor and, in the case of the present embodiment, include the direction and magnitude of acceleration (including gravitational acceleration) of an object, an angular velocity (magnitude, direction and center position) of the object, and the direction (orientation) and magnitude of a magnetic field. The relative positional relationship of the body motion sensors 41a to 41e is represented by the mutual distances thereamong and movable ranges which are determined by the skeleton of a wearer and the positions of the body motion sensors 41a to 41e, which are worn on the wearer. For example, as illustrated in FIG. 15B, the lower half of a human body consists of a pelvis B7, a pair of thighbones B1 and B2 connected to the pelvis B7, tibias B3 and B4 connected to the thighbones B1 and B2 respectively, and tarsal bones B5 and B6 further connected to the tibias B3 and B4 respectively. Each bone is bendably or pivotally connected with a joint, but hardly changes its length. Also, the bending angles R13, R24, R35 and R46 of respective joints have limited movable ranges respectively. Accordingly, body motion reproduction data for reproducing the motion and posture of a wearer can be generated from the relative positional relationship among the body motion sensors 41a to 41e and the detection results of the body motion sensors determined by the lengths of the bones and the movable ranges of the joints.

Furthermore, in the case of the present embodiment, this body motion calculation unit is provided with the cycle extracting unit 170a. The cycle extracting unit 170a extracts cyclic variation from body motions on the basis of the body motion reproduction data accumulated on the memory 114. Such cyclic variation includes not only simple circular motions but also three-dimensional complicated orbital motions C1 to C3 in which are combined wavelike motions and motions in the shape of a figure eight as illustrated in FIG. 27A and FIG. 27B. In the case of the present embodiment, the extracted orbital motions include an orbital motion C2a of the right knee body motion sensor 41a worn on the right knee of the wearer, an orbital motion C2b of the left knee body motion sensor 41b worn on the left knee of the wearer, an orbital motion C1a of the right foot body motion sensor 41c worn on the instep of the right foot of the wearer, an orbital motion C1b of the left foot body motion sensor 41d worn on the instep of the left foot of the wearer, an orbital motion (swinging motion) C3 of the waist body motion sensor 41e worn on the waist of the wearer. Each of the orbital motions C1a, C1b, C1c and C1d comprises a main orbital motion component in a plane xy defined by the vertical direction y and the direction x in which a wearer runs during running or a bicycle race. The orbital motion C3 is an orbital motion which tends to comprise a main orbital motion component in a plane crossing the plane xy. Incidentally, the analysis unit 170e has the function to analyze the pattern of an orbital motion to automatically determine the event of the competition which is currently taking place by extracting the characteristics of the orbital motion, and switch the settings of processes to the settings which are suitable for the event.

The cyclic variation can be extracted, for example, by monitoring a body motion sensor, such as the waist body motion sensor 41e, attached to a part of a body corresponding to a swinging point defined on the center line of a wearer's body to detect the three-dimensional displacement or acceleration of the waist body motion sensor 41e (swinging point) and measure the orbital motion C3 of the swinging point. While this orbital motion C3 is an orbital motion comprising a main orbital motion component in a plane crossing the plane xy, the swinging point such as a waist defined on the center line of a human body swings substantially with regularity even during exercising such as running or cycling so that it is possible to correct error in the detection results of the other sensors in relation to the timing of this swinging motion. Incidentally, the body motion data from which cyclic variation is extracted is not limited to the body motion data obtained by the waist body motion sensor 41e but also the body motion data obtained by any one of the body motion sensors 41a to 41e or a combination thereof. Alternatively, the cyclic variation in the pressure acquired by the sole sensors as described in the above embodiments can be used.

Meanwhile, in the case of the present embodiment, the body motion calculation unit 170b calculates body motions of a wearer as body motion reproduction data on the basis of the detection results of the body motion sensors 41a to 41e and the variation in the relative positional relationship among the body motion sensors 41a to 41e. In this case, for example as illustrated in FIG. 25, the body motion calculation unit 170b calculates reference orbital locuses $C1a_{xy}$ and $C1b_{xy}$ projected on a vertical plane (xy plane in FIG. 28) in parallel with the gravity direction (direction y in FIG. 27B) and the direction x in which a wearer runs (direction x in FIG. 27B) and calculates three-dimensional free orbital locuses C1 of the body motion sensors 41a to 41e on the basis of the detection results of the waist body motion sensor 41e. The body motion calculation unit 170b then estimates the relative displacements among the body motion sensors on both the left and right sides of a wearer (the sensors 41a and 41c on the right side and the sensors 41b and 41d on the left side) and the waist body motion sensor 41e on the basis of the differences between the calculated reference orbital locuses $C1_{xy}$ ($C1a_{xy}$ and $C1b_{xy}$) and the calculated free orbital locuses C1 (C1a and C1b) respectively. Then, the body motion reproduction data is calculated on the basis of the calculated reference orbital locuses $C1_{xy}$, the calculated free orbital locuses C1 and the estimated relative displacements. The differences between the calculated reference orbital locuses $C1_{xy}$ and the calculated free orbital locuses C1 can be used as data for estimating the degree of the collapse of the ideal form so that coaching and the like can be performed.

The correction unit 170d is a module for correcting the body motion reproduction data calculated by the body motion calculation unit 170b on the basis of the detection results of the cycle extracting unit 170a. In the correction process by the correction unit 170d, the body motion sensors 41 as described above calculate the entire displacements and rotations by continuously accumulating the value measured by each sensor. However, since noise and error occurring in the detection results of the sensors are accumulated, there may be deviation from actual positions, displacements and postures. Because of this, in the case of the present embodiment, it is determined that the moment the detection result of the cycle extracting unit 170a is returned in the correction unit 170d to a certain reference point obtained on the basis of the cyclic pattern (for example, the moment the waist body motion sensor 41e passes through the center axis of a body), the cyclic motion reaches the end point of the current cycle, i.e., the start point of the next cycle. On the assumption that the orbital motions of the other body motion sensors reach the end points and the start points at that moment, the positions and the rotation angles are corrected.

the analysis unit 170e is a module for analyzing body motions of a wearer on the basis of the body motion reproduction data corrected by the correction unit 170d. This analysis method may be performed to generate stereoscopic image data for three-dimensionally displaying a wearer on the basis of the body motion reproduction data after correction. And, improved data indicating displacements from normal body motions may be generated by extracting representative body motion data from the memory 114 which accumulates representative body motion data, comparing the body motion reproduction data of a wearer with the representative body motion data. Furthermore, the analysis can be performed on the basis of user information by registering user information such as gender, height, weight and age. The analysis unit 170e then transmits the analysis results such as the stereoscopic image data, the improved data and the like to the information terminal device 100b.

The memory 114 is a storage unit for accumulating various data such as the identification information for identifying each information terminal device 100b, the wearing part identification information of each sensor 40, the relative positional relationship of the body motion sensors 41 worn on the respective parts, the user information, the representative body motion data and the like.

(Motion Capture Method)

Figure 30:
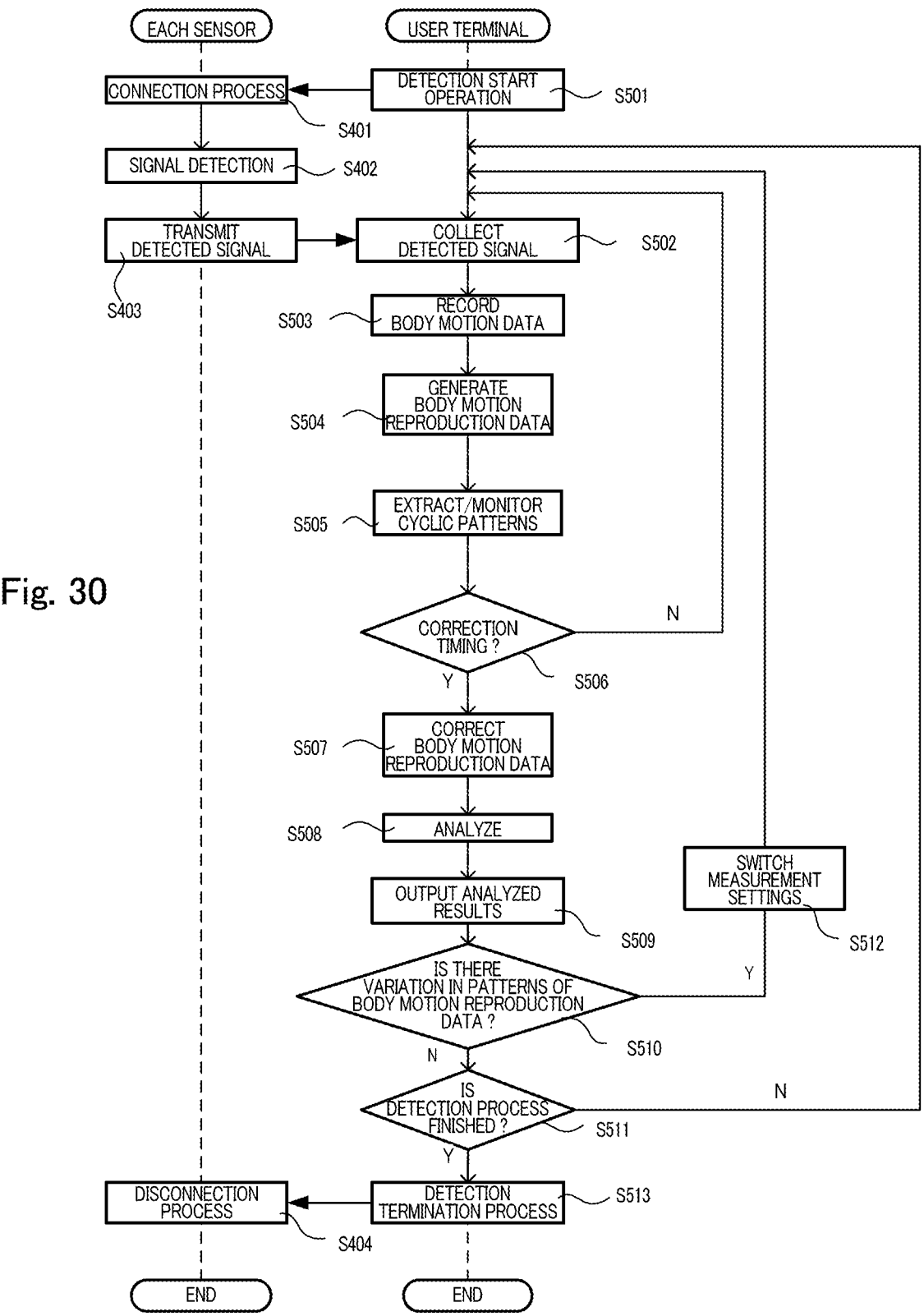
FIG. 30 is a sequence diagram for showing the motion capture method in accordance with the fifth embodiment.

The motion capture method in accordance with the present invention can be implemented by operating the motion capture system having the structure as described above. FIG. 30 is a sequence diagram for showing the motion capture method in accordance with the present embodiment. Incidentally, this example is explained in the case where a bicycle competition is switched to a running competition without interruption such as in triathlon.

First, a wearer wears the body motion sensors 41a to 41d on both knees and both feet, and wears the waist body motion sensor 41e on the shoe soles. Also, the wearer wears the information terminal device 100b. In this case, the bicycle competition can be performed by fixing the wearing type terminal 1b to a handlebar of a bicycle through the mount device 102 and the docking type device 2b and performing motion capture while charging the wearing type terminal 1b from the docking type device 2 and the power supply device 3b. Thereafter, the wearing type terminal 1b is detached from the docking type device 2b and worn on an arm of a wearer with the belt member 4.

When fixing or attachment of the information terminal device 100b is completed, the information terminal device 100b is then operated in order to acquire the detection results from the sensors 40 (S501). In this case, while a competition item can be select by user operation, it is also possible to switch the process settings to the settings suitable for the competition item by extracting the characteristics of the orbital motion as described above and determining the preset event of the competition from the extracted pattern. By this function, it is possible to seamlessly continue measurement without a need for particular operation even when the competition item is switched in the middle.

The control unit 170 of the wearing type terminal 1b acquires an operation signal in response to the operation for starting detection, and then performs a connection process with the sensors 40 (S401). After performing the connection process, each sensor 40 detects the motion of the wearer. Specifically, three-dimensional displacements or accelerations at each part of the wearer are detected by the body motion sensor 41 worn on this each part (S402). Then, the detection results which are acquired are transmitted to the wireless communication unit 119b of the wearing type terminal 100b from the wireless communication unit of each sensor 40 by using weak electric waves (S403). When the wireless communication unit 119b of the wearing type terminal 100b acquires the detection results (S502), the memory 114 serving as a body motion recording unit accumulates the detection results of the body motion sensors 41a to 41e and the sole sensors 42 as body motion data (S503).

Thereafter, after the body motion data acquisition unit 170c acquires the body motion data, the body motion data acquisition unit 170c transmits the detection results of the body motion sensor 41 to the body motion calculation unit 52, and transmits the detection results of the cycle extracting unit 170a to the correction unit 54. The body motion calculation unit 52 calculates body motions of the wearer as body motion reproduction data on the basis of the detection results of the body motion sensors 41 accumulated in the body motion recording unit and the relative positional relationship among the body motion sensors 41 (S504), and transmits the body motion reproduction data to the correction unit 170d. On the other hand, when a predetermined cycle arrives on the basis of the detection results of the cycle extracting unit 170a ("Y" in S506), the correction unit 54 corrects the body motion reproduction data calculated by the body motion calculation unit 52 (S507). The corrected body motion reproduction data is then transmitted to the analysis unit 55.

The analysis unit 55 analyzes the body motions of the wearer on the basis of the body motion reproduction data which is corrected by the correction unit 54 (S508). The analysis result data is displayed in the display unit 131 or output through a speaker by sound (S509). Incidentally, when variation is detected in the patterns of the extracted orbital motion and body motion reproduction data ("Y" in S510), the event of the competition which is currently taking place is automatically determined with reference to the patterns to switch over to measurement settings suitable for the competition event (S512).

The above process is continuously performed during competition ("N" in S511), and, the communication with the sensors are terminated (S513 and S404) as soon as the detection process is finished ("Y" in S511).

(Effect/Action)

In accordance with the present embodiment as discussed above, it is possible to let a wearer recognize body motions of the wearer herself, and advise improvement of the body motions of the wearer, by attaching the body motion sensors 41a to 41e to the body of the wearer, calculating the body motions of the wearer as body motion reproduction data on the basis of the detection results of the sensors 40, analyzing the body motion reproduction data, and displaying the analysis results on the display unit 131.

At this time, since the correction unit 54 corrects the body motion reproduction data calculated by the body motion calculation unit 52 on the basis of the detection results of the cycle extracting unit 170a, even when a deviation occurs in the relative position of the body motion reproduction data to the ground due to noise and error occurring in the detection results of the body motion sensors 41 such as nine-axis sensors, it is possible to appropriately build, display and output the body motion reproduction data by making use of the patterns and timings of orbital motions detected by the cycle extracting unit 170a to correct the value of each body sensor 41 (for example, zero correction).

Also, in the case of the present embodiment, since the memory 114 of the information terminal device 100b serves as a body motion recording unit which accumulates the detection results of the body motion sensors 41a to 41e as body motion data, it is possible to make the device for accumulating body motion data in the form of a wearable watch type device having excellent portability and easily collect body motion data while performing exercise and sports.

Furthermore, in the case of the present embodiment, the wireless communication unit 119b of the wearing type terminal 1b uses a wireless communication system such as Bluetooth (registered trademark), BTLE or ANT. Meanwhile, since the number of devices which can be simultaneously connected is limited in such a wireless communication system (up to a maximum of 6 in the case of Bluetooth (registered trademark)), in the case of the present embodiment, the body motion reproduction data is calculated by the use of six sensors 40 in total, i.e., five body sensors 41a to 41e worn on both knees and both feet of the wearer and further worn on the waist for the purpose of makes it possible to calculate and analyze the body motion reproduction data of the wearer with the minimal number of sensors. As a result, in accordance with the present embodiment, it is possible to calculate and analyze the body motion reproduction data of a wearer without changing the structure of the information terminal device 100b of the embodiments as described above.

DESCRIPTION OF REFERENCE SIGNS

C1 . . . free orbital locus
C1xy . . . reference orbital locus
C1 to C2 . . . free orbital locus
C3 . . . swing motion
1 (1a, 1b) . . . wearing type terminal
2 (2a, 2b) . . . docking type device
3, 3b . . . power supply device
4 (4a, 4b) . . . belt member
5 . . . server device
6 . . . user terminal
7 . . . radio base station
8 . . . communication network
9 . . . personal computer
10 . . . external case
11 . . . terminal side connection terminal
11a . . . insertion hole
12a to 12c . . . operation button
14 . . . packing
15 . . . display unit supporting plate
16 . . . antenna spring
17 . . . circuit board
18 . . . GPS antenna
19 . . . back lid
21 . . . dock side connection terminal
22a, 22b . . . operation button
23 . . . microphone
24, 24a . . . wireless antenna
25 . . . speaker
31 . . . power supply device side connection terminal
32 . . . connector
33 . . . USB terminal
34 . . . lid member
35 . . . cylindrical member
40 . . . sensor
41 (41a to 41g) . . . body motion sensor
42 (42a, 42b) . . . sole sensor
51 . . . communication interface
52, 170 b . . . body motion calculation unit
53, 170 c . . . body motion data acquisition unit
54, 170 d . . . correction unit
55, 170 e . . . analysis unit
56 . . . storage unit 61 . . . wireless interface
62 . . . input interface
63 . . . output interface
63a . . . display panel
64 . . . application running unit
65 . . . memory
70 . . . hub
71 . . . data collection unit
71a . . . first group collection unit
71b . . . second group collection unit
72 . . . data transfer unit
100, 100 a, 100b . . . information terminal device
101 . . . mount device
102 . . . handlebar (bicycle)
103a . . . small display
103b . . . large display
104 . . . operation unit
111 . . . output interface
112 . . . input interface
114 . . . memory
115 . . . acceleration sensor
116 . . . wireless antenna
117 . . . wireless communication unit
119 . . . GPS receiver unit
131, 133 . . . display unit
131a to 131c . . . display screen
132a, 132b . . . crease
134 . . . protection cover
135 . . . touch sensor
136 . . . display panel
170 . . . control unit
170a . . . cycle extracting unit
171 . . . connector for liquid crystal panel.
172 . . . connector for TPC
173 . . . protection member
174 . . . area
175, 176, 177 . . . flexible printed circuit board
178 . . . battery
181 . . . main body
184 . . . projection member
200 . . . control unit
201 . . . output interface
202 . . . battery
203 . . . memory
204 . . . vibration motor
206, 206a . . . wireless communication unit
207 . . . input interface

What is claimed is:

1. A motion capture apparatus, comprising:
an information terminal device which is wearable by a wearer or can be mounted on a bicycle; and
sensors which are connected to the information terminal device through wireless communication, wherein
the sensors include body motion sensors which are worn on parts of a body of the wearer to detect three-dimensional displacement and acceleration of the parts of the body,
the information terminal device includes a body motion data acquisition unit, a body motion calculation unit, a cycle extracting unit, a correction unit and an analysis unit,
the body motion data acquisition unit acquires body motion data from the sensors through the wireless communication,
the body motion data includes:
sensor identification information for identifying the sensors and identifying the parts on which the sensors are worn; and
time information when a detection result is acquired from the sensors,
the body motion calculation unit identifies the parts on which the sensors are worn by determining the sensors from which the detection result is outputted,
the body motion calculation unit calculates body motion calculation data of a motion and posture of the wearer on the basis of the detection result of the body motion sensors and relative positional relationship among the body motion sensors determined by a skeleton of the wearer and positions of the body motion sensors, the relative positional relationship including mutual distances,
the cycle extracting unit extracts a three-dimensional circular motion from the body motion calculation data,
the correction unit corrects the body motion calculation data calculated by the body motion calculation unit on the assumption that the three-dimensional circular motion reaches an end point of the current cycle and a start point of the next cycle at a certain reference point of the three-dimensional circular motion on the basis of the detection result of the cycle extracting unit,
the analysis unit analyzes body motions on the basis of the body motion calculation data corrected by the correction unit and displays or outputs an analysis result,
at least one of the body motion sensors is attached to the parts of the body corresponding to a swinging point defined on the center line of the body of the wearer to detect a three-dimensional displacement or acceleration of the swinging point,
the body motion calculation unit calculates reference orbital locuses projected on a vertical plane in parallel with a gravity direction and the direction in which the wearer runs on the basis of the detection result of the cycle extracting unit,
the body motion calculation unit calculates three-dimensional free orbital locuses of the body motion sensors on the basis of the detection results of body motion sensors,
the body motion calculation unit estimates relative displacements among the body motion sensors on both the left and right sides of the wearer on the basis of the differences between the calculated reference orbital locuses and the calculated free orbital locuses,
the body motion calculation unit calculates the body motion calculation data on the basis of the calculated reference orbital locuses, the calculated free orbital locuses and the estimated relative displacements,
the correction unit corrects error in the detection results of the other body motion sensors in relation to the timing of swinging motion of the swinging point in a plane crossing the vertical plane,
the analysis unit compares the body motion calculation data corrected by the correction unit with a representative body motion data, and
the analysis unit displays or outputs an improved data indicating displacements from normal body motions as the analysis result.

2. The motion capture apparatus according as recited in claim 1, wherein
the sensors includes a sole sensor, and
the correction unit corrects the body motion calculation data on the basis of the detection results of the sole sensor.

3. The motion capture apparatus as recited in claim 1, wherein the information terminal device comprises: a wrist watch type wearable terminal which can be worn by a user with a belt member; a docking type device; and a power supply device which is detachably connected with the docking type device.

4. The motion capture apparatus as recited in claim 1, wherein the correction unit corrects error in the detection results of the body motion sensors in relation to the timing of the sole sensor.

5. The motion capture apparatus as recited in claim 1, wherein the correction unit corrects height of the body motion sensors and corrects positions and rotation angles of the detection results of from the body motion sensors.

* * * * *